(12) United States Patent
Zang et al.

(10) Patent No.: US 11,613,537 B2
(45) Date of Patent: Mar. 28, 2023

(54) SENSOR COMPOUNDS AND ASSOCIATED METHODS AND DEVICES

(71) Applicant: University of Utah Research Foundation, Salt Lake City, UT (US)

(72) Inventors: Ling Zang, Salt Lake City, UT (US); Paul Slattum, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 382 days.

(21) Appl. No.: 16/835,735

(22) Filed: Mar. 31, 2020

(65) Prior Publication Data

US 2020/0354356 A1 Nov. 12, 2020

Related U.S. Application Data

(62) Division of application No. 15/743,259, filed as application No. PCT/US2016/041759 on Jul. 11, 2016, now Pat. No. 11,261,181.

(Continued)

(51) Int. Cl.
*G01N 21/00* (2006.01)
*C07D 471/04* (2006.01)
(Continued)

(52) U.S. Cl.
CPC ......... *C07D 471/04* (2013.01); *C07D 221/18* (2013.01); *C07D 491/052* (2013.01);
(Continued)

(58) Field of Classification Search
CPC .................................................... C07D 471/04
(Continued)

(56) References Cited

U.S. PATENT DOCUMENTS 8,674,104 B2 * 3/2014 Koenemann ........ H01L 51/0053
546/37
2004/0038408 A1 2/2004 Abbott et al.
(Continued)

FOREIGN PATENT DOCUMENTS

CN 102762566 A 10/2012
CN 103193775 A 7/2013
(Continued)

OTHER PUBLICATIONS

Acikbas et al. Thin film characterization and vapor sensing properties of a novel perylenediimide material (Sensors and Actuators B 200 (2014) 61-68) (Year: 2014).*
(Continued)

*Primary Examiner* — Christine T Mui
*Assistant Examiner* — Emily R. Berkeley
(74) *Attorney, Agent, or Firm* — Thorpe North & Western LLP

(57) ABSTRACT

Methods of detecting a non-explosive analyte can include exposing a sensor compound to a non-explosive analyte and displaying a change in the sensor compound upon exposure of the sensor compound to the non-explosive analyte. A variety of sensor compounds for detecting a target analyte, including both explosive and non-explosive analytes, is also described. Sensor devices for detecting a target analyte can include a substrate and a sensor compound positioned on the substrate in a plurality of detection zones.

24 Claims, 22 Drawing Sheets

Related U.S. Application Data

(60) Provisional application No. 62/190,609, filed on Jul. 9, 2015.

(51) Int. Cl.
    *G01N 21/64*     (2006.01)
    *C07D 221/18*     (2006.01)
    *C07D 491/052*     (2006.01)
    *G01N 27/12*     (2006.01)
    *B82Y 30/00*     (2011.01)

(52) U.S. Cl.
CPC ......... *G01N 21/643* (2013.01); *G01N 27/126* (2013.01); *B82Y 30/00* (2013.01); *G01N 2021/6432* (2013.01)

(58) Field of Classification Search
USPC ........................................................ 324/693
See application file for complete search history.

(56) References Cited

U.S. PATENT DOCUMENTS

| | | |
|---|---|---|
| 2007/0004046 A1 | 1/2007 | Abbott |
| 2008/0035914 A1 | 2/2008 | Konemann et al. |
| 2008/0054258 A1 | 3/2008 | Koenemann et al. |
| 2008/0242870 A1 | 10/2008 | Meador et al. |
| 2010/0055801 A1 | 3/2010 | Yi et al. |
| 2010/0093096 A1 | 4/2010 | Acharya et al. |
| 2010/0144043 A1 | 6/2010 | Zang et al. |
| 2010/0197039 A1 | 8/2010 | Zang et al. |
| 2011/0136333 A1 | 6/2011 | Facchetti et al. |
| 2011/0257400 A1 | 10/2011 | Carson et al. |
| 2012/0055236 A1 | 3/2012 | Takulapalli |
| 2013/0065319 A1 | 3/2013 | Zang et al. |
| 2013/0183766 A1 | 7/2013 | Zang et al. |
| 2013/0302902 A1 | 11/2013 | Zang et al. |
| 2014/0004455 A1* | 1/2014 | Sekido .................. G03G 15/751 546/66 |

FOREIGN PATENT DOCUMENTS

| | | |
|---|---|---|
| CN | 103497189 A | 1/2014 |
| CN | 103709161 A | 4/2014 |
| CN | 103975237 A | 8/2014 |
| CN | 104130257 A | 11/2014 |
| WO | WO 2011/079296 A2 | 6/2011 |
| WO | WO 2012/134436 | 10/2012 |
| WO | WO 2013/066458 A2 | 5/2013 |
| WO | WO 2013/095730 A2 | 6/2013 |

OTHER PUBLICATIONS

Shin et al. Efficient Fluorescence "Turn-On" Sensing of Dissolved Oxygen by Electrochemical Switching (Anal. Chem. 2012, 84, 9163-9168) (Year: 2012).*

Ahmed et al. Synthesis and study of electrochemical and optical properties of substituted perylenemonoimides in solutions and on solid surfaces (J. Mater. Chem. A, 2015, 3, 13332) (Year: 2015).*

Aigner et al. "Novel near infra-red fluorescent pH sensors based on 1-aminoperylene bisimides covalently grafted onto poly(acryloylmorpholine)" Chem. Commun., 2013, 49, 2139 (Year: 2013).*

Zang et al. "A Single-Molecule Probe Based on Intramolecular Electron Transfer" J. Am. Chem. Soc. 2002, 124, 10640-10641 (Year: 2002).*

Segura et al. "Synthesis and Electronic Properties of Anthraquinone-,Tetracyanoanthraquinodimethane-, and Perylenetetracarboxylic Diimide-Functionalized Poly(3,4-ethylenedioxythiophenes)" Chem. Mater. 2006, 18, 2834-2847 (Year: 2006).*

Robb et al. "One-Step Synthesis of Unsymmetrical N-Alkyl-N'-aryl Perylene Diimides" J. Org. Chem. 2014, 79, 6360-6365 (Year: 2014).*

Ernst et al.; "Excitation characteristics of different energy transfer in nanotube-perylene complexes." Appl. Phys. Lett. 102; Published online Jun. 12, 2013; pp. 233105-1-233105-5.

Huang et al.; "Self-Assembled Organic Functional Nanotubes and Nanorods and Their Sensory Properties." J. Phys. Chem. C 2009, 113, pp. 3929-3933.

Jiang et al.; "Self-Assembly of Amphiphilic Perylene—Cyclodextrin Conjugate and Vapor Sensing for Organic Amines." J.Org, Chem. 2010, 75; pp. 7258-7264.

Kumar et al.; "The molecular recognition controlled stereomutation cycle in a dynamic helical assembly." Organic & Biomolecular Chemistry; Org. Biomol. Chem., 2015, 13, pp. 9938-9942.

Kunz et al.; "Embedding of a ruthenium (II) water oxidation catalyst into nanofibers via self-assembly." Chem, Commun, 2015, 51; pp. 290-293.

Liu et al.; "Nanocoiled Assembly of Asymmetric Perylene Diimides: Formulation of Structural Factors." J. Phys. Chem. C., 2015, 119; ACS publications; pp. 6446-6452.

Peng et al.; "Self-assembly and phase separation of amphiphilic dyads based on 4,7-bis(2-thienyl) benzothiodiazole and perylene diimide." RSC Adv., 2014, 4; pp. 13078-13084.

Ramesh.; "Stable organic thin film transducers for biochemical and label-free sensing under physiological conditions." J. Mater. Chem., 2012, 22; pp. 16506-16513.

Yao et al.; "Morphologies and optical properties of nanostructures self-assembled from asymmetrical, amphiphilic perylene derivatives." J Mater Sci (2011) 46; pp. 188-195.

Yu et al.; "Selectively detecting trace picric acid by reduced perylene bisimide with POSS substituents and their nanoaggregates." RSC Advances; RSC Adv., 2015, 5; pp. 29262-29265.

Zhang et al.; "Fluorescent and photoconductive nanoribbons as a dual-mode sensor for selective discrimination of alkyl amines versus aromatic amines." Chem. Commun., 2015. 51, pp. 15004-15007.

Zhang et al.; "Vesicular perylene dye nanocapsules as supramolecular fluorescent pH sensor systems." Nature Chemistry; vol. 1; Nov. 2009; pp. 623-629.

Zhou et al.; "Cyclen-functionalized perylenebisimides as sensitive and selective fluorescent sensors for $Pb^{2+}$ in aqueous solution." Chem, Commun., 2011, 47 pp. 6668-6670.

Acikbas et al.; "Fabrication of Langmuir-Blodgett thin film for organic vapor detection using a novel N,N'-dicyclohexyl-3, 4:9, 10-perylenebis (dicarboximide)." Sensors and Actuators B: Chemical; Elsevier; Sep. 2014; vol. 200; pp. 61-68.

Aigner et al.; "Enhancing Photoinduced Electron Transfer Efficiency of Fluorescent pH-Probes with Halogenated Phenols;" Analytical Chemistry; (Sep. 16, 2014); pp. 9293-9300; vol. 86 No. 18; <doi: 10.1021/ac502513g>.

Aparicio et al.; "Plasma Deposition of Perylene—Adamantane Nanocomposite Thin Films for $NO^2$ Room-Temperature Optical Sensing"; The Journal of Physical Chemistry C; (Mar. 16, 2012); pp. 8731-8740; vol. 116, No. 15; American Chemical Society; <doi: 10.1021/jp209272s>.

Biadasz et al.; "Langmuir films of dichroic dyes with fluorescent properties"; Dyes and Pigments; (2003); pp. 209-217; vol. 56, Issue 3; <doi: 10.1016/S0143-7208(02)00156-0>.

Biedermann et al.; "Associative Chemosensing by Fluorescent Macrocycle—Dye Complexes—A Versatile Enzyme Assay Platform Beyond Indicator Displacement;" Journal of the Chemical Society, Chemical Communications; (Jan. 15, 2015); pp. 4977-4980; vol. 51, No. 24; <doi: 10.1039/c4cc10227d>.

Boobalan et al.; "Fabrication of highly fluorescent perylene bisimide nanofibers through interfacial self-assembly"; Journal of Colloid and Interface Science; (2013); pp. 377-383; vol. 393; Elsevier; <doi: 10.1016/j.jcis.2012.10.053>.

Che et al.; "Expedient Vapor Probing of Organic Amines Using Fluorescent Nanofibers Fabricated from an n-Type Organic Semiconductor"; Nano Letters; (2008); pp. 2219-2223; vol. 8, No. 8; American Chemical Society; <doi: 10.1021/nl080761g>.

(56) References Cited

OTHER PUBLICATIONS

Che et al.; "Ultrathin n-Type Organic Nanoribbons with High Photoconductivity and Application in Optoelectronic Vapor Sensing of Explosives"; Journal of American Chemical Society; (2010); pp. 5743-5750; vol. 132; American Chemical Society; <doi: 10.1021/ja909797q>.

Chen et al.; "Multicomponent Covalent Dye Assembly for Tight Binding and Sensitive Sensing of L-DOPA;" Journal of the Chemical Society, Chemical Communication; (Jul. 17, 2015); pp. 13630-13633; vol. 51, No. 71; <doi: 10.1039/c5cc03495g>.

Cui et al.; "Tailoring the structures and compositions of one-dimensitonal organic nanomaterials towards chemical sensing applications"; Chemical Science; (2014); pp. 52-57; vol. 5; The Royal Society of Chemistry; <doi: 10.1039/c3sc51798e>.

Eakins et al.; "Functional Organic Semiconductors Assembled via Natural Aggregating Peptides;" Advanced Functional Materials; (Aug. 4, 2015); pp. 5640-5649; vol. 25, No. 35; <doi: 10.1002/adfm.201502255>.

Fin et al.; "Naphthalene- and Perylenediimides with Hydroquinones, Catechols, Boronic Esters and Imines in the Core;" Organic & Biomolecular Chemistry; (Aug. 30, 2011); pp. 8246-8252; vol. 9, No. 24; <doi: 10.1039/c1ob05702b>.

Goulet et al.; "Distinguishing Individual Vibrational Fingerprints: Single-Molecule Surface-Enhanced Resonance Raman Scattering from One-to-One Binary Mixtures in Langmuir-Blodgett Monolayers;" Analytical Chemistry; (Apr. 1, 2007); pp. 2728-2734; vol. 79, No. 7; <doi: 10.1021/ac062059f>.

Huang et al.; "Effect of core-substituted groups on sensing properties based on single micro/nanorod of perylenediimide derivatives"; Sensors and Actuators B: Chemical; (Jul. 25, 2013); pp. 411-416; vol. 188; Elsevier; <doi:10.1016/j.snb.2013.07.021>.

Huang et al.; "Morphology Control of Nanofibril Donor—Acceptor Heterojunction To Achieve High Photoconductivity: Exploration of New Molecular Design Rule"; Journal of the American Chemical Society; (2013); pp. 16490-16496; vol. 135; American Chemical Society; <doi: 10.1021/ja407024u.

Li et al., "Optoelectronics of Organic Nanofibers Formed by Co-assembly of Porphyrin and Perylenediimide"; Small Journal.com; (Jul. 23, 2014); 6 pages; vol. 10, Issue 14; <doi: 10.1002/smll.201302964>.

Mohr; "Tailoring the Sensitivity and Spectral Properties of a Chromoreactand for the Detection of Amines and Alcohols;" Analytica Chimica Acta; (Jan. 1, 2004); pp. 233-237; vol. 508, No. 2; <doi: 10.1016/j.aca.2003.12.005>.

Sengupta et al.; "Synthesis of Regioisomerically Pure 1,7-Dibromoperylene-3,4,9,10-tetracarboxylic Acid Derivatives"; The Journal of Organic Chemistry; (2014); pp. 6655-6662; vol. 79, Issue 14; American Chemical Society; <doi: 10.1021/jo501180a>.

Shin et al.; "Efficient Fluorescence "Turn-On" Sensing of Dissolved Oxygen by Electrochemical Switching." Analytical Chemistry; ACS Publishing; Sep. 25, 2012; vol. 84; pp. 9163-9168.

Supplementary European Search Report dated Jan. 10, 2019, in EP Application No. 16822086.1, filed Jul. 11, 2016; 4 pages.

Wang et al.; "Facile synthesis and controllable bromination of asymmetrical intermediates of perylene monoanhydride/monoimide diester"; Dyes and Pigments; (Sep. 2013); pp. 450-458; vol. 98, Issue 3; Elsevier; <doi: 10.1016/jdyepig.2013.04.006>.

Che et al.; "Ultra long Nanobelts Self-Assembled from an Asymmetric Perylene Tetracarboxylic Diimide." J. Am. Chem. Soc.; May 17, 2007; 129, 23; pp. 7234-7235.

Flaminigi et al.; "On/Off Switching of Perylene Tetracarboxylic Bisimide Luminescence by Means of Substitution at the N-Position by Electron-Rich Mono-, Di-, and Trimethoxybenzenes," Chem. Eur. J. 2010, 16, 13406-13416.

* cited by examiner

SENSOR COMPOUNDS AND ASSOCIATED METHODS AND DEVICES

RELATED APPLICATIONS

This application is a divisional application of U.S. application Ser. No. 15/743,259, filed Jan. 9, 2018, which is a 371 national stage application of PCT International Application No. PCT/US16/41759 filed Jul. 11, 2016, which claims priority to U.S. Provisional Application No. 62/190,609, filed Jul. 9, 2015, which are each incorporated herein by reference.

GOVERNMENT INTEREST

This invention was made with government support under 2009-ST-108-LR0005 awarded by the U.S. Department of Homeland Security. The government has certain rights in the invention.

BACKGROUND

Development of sensors or probes that can be used to detect fluid analytes is an active research field in chemistry and materials science. Detection of some fluid analytes is not only critical to air pollution monitoring and control, but also may provide expedient ways for quality control of food and even medical diagnosis of certain types of disease. However, detection of some fluid analytes can be challenging, largely due to the limited availability of sensory materials that facilitate detection with both high sensitivity and selectivity.

One dimensional (1D) nanostructures represent attractive building blocks for some sensors and probes for fluid detection. Most of these nanodevices are fabricated from inorganic nanowires and carbon nanotubes. Some 1D organic nanomaterials have also been demonstrated, most of which are p-type semiconductor materials due to the limited availability of air-stable n-type organic materials.

SUMMARY

The current disclosure is directed to sensor compounds and associated methods and devices. In one example, a method of detecting a non-explosive analyte is disclosed. The method can include exposing a sensor compound to a non-explosive analyte and displaying a change in the sensor compound upon exposure of the sensor compound to the non-explosive analyte. The sensor compound can be selected from a group of compounds. In one example, the compound can have a structure according to Formula I:

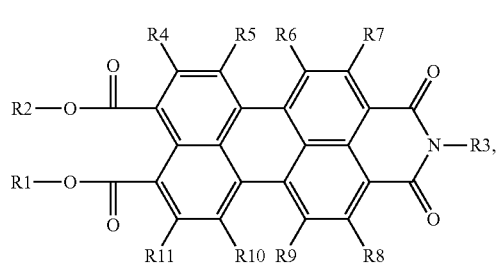

where R1, R2, and R3 are independently chosen from $C_1$-$C_{20}$ substituted or unsubstituted linear aliphatic groups, branched aliphatic groups, cyclic groups, and aryl groups, and where R4-R11 are independently chosen from hydrogen, halides, carboxyl groups, hydroxyl groups, nitrile groups, $C_1$-$C_8$ alkyl groups, and combinations thereof.

In another example, the sensor compound can have a structure according to Formula II:

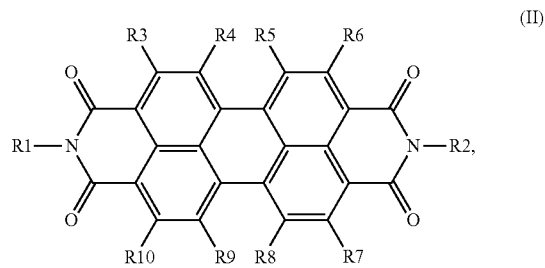

where R1 and R2 are independently chosen from $C_1$-$C_{20}$ substituted or unsubstituted linear aliphatic groups, branched aliphatic groups, cyclic groups, and aryl groups, and where R3-R10 are independently chosen from hydrogen, halides, carboxyl groups, hydroxyl groups, nitrile groups, $C_1$-$C_8$ alkyl groups, and combinations thereof.

In yet another example, the sensor compound can have a structure according to Formula III:

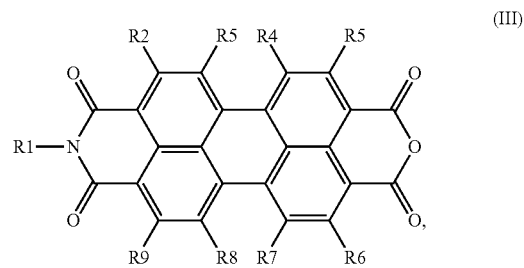

where R1 is chosen from $C_1$-$C_{20}$ substituted or unsubstituted linear aliphatic groups, branched aliphatic groups, cyclic groups, and aryl groups, and where R2-R9 are independently chosen from hydrogen, halides, carboxyl groups, hydroxyl groups, nitrile groups, $C_1$-$C_8$ alkyl groups, and combinations thereof. In some examples, combinations of the above recited compounds can be used in the method.

The current disclosure also provides sensor compounds for detecting a target analyte. The sensor compounds can include compounds having a structure according to Formula I:

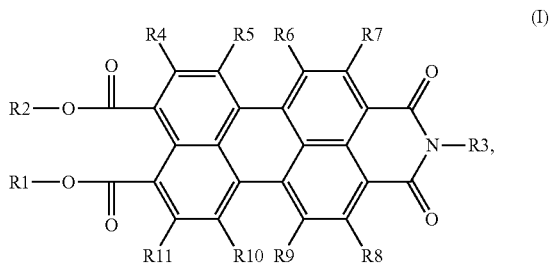

where R1, R2, and R3 are independently chosen from $C_1$-$C_{20}$ substituted or unsubstituted linear aliphatic groups, branched aliphatic groups, cyclic groups, and aryl groups, and where R4-R11 are independently chosen from hydrogen, halides, carboxyl groups, hydroxyl groups, nitrile groups, $C_1$-$C_8$ alkyl groups, and combinations thereof.

In some examples, the sensor compound can have a structure according to Formula II:

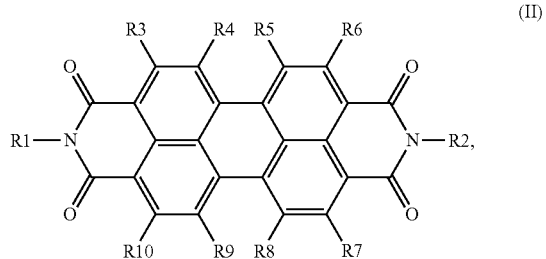

where R1 is chosen from $C_2$-$C_{20}$ substituted or unsubstituted linear aliphatic groups, branched aliphatic groups, cyclic groups, and aryl groups, where R2 includes a $C_2$-$C_{10}$ substituted or unsubstituted linear aliphatic group, an alkylbenzene group, a heterocycle, an aryl compound having an oxygen-containing side group, an aryl compound having a nitrogen-containing side group, an aryl compound having a sulfur-containing side group, or a combination thereof, and where R3-R10 are independently chosen from hydrogen, halides, carboxyl groups, hydroxyl groups, nitrile groups, $C_1$-$C_8$ alkyl groups, and combinations thereof.

The current disclosure also describes a sensor device for detecting a target analyte. The sensor device can include a substrate and a nanofiber sensor material positioned on the substrate in a plurality of detection zones. The nanofiber sensor material can include a sensor compound as described above. Further, the sensor compound can have a nanofiber structure.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1A:
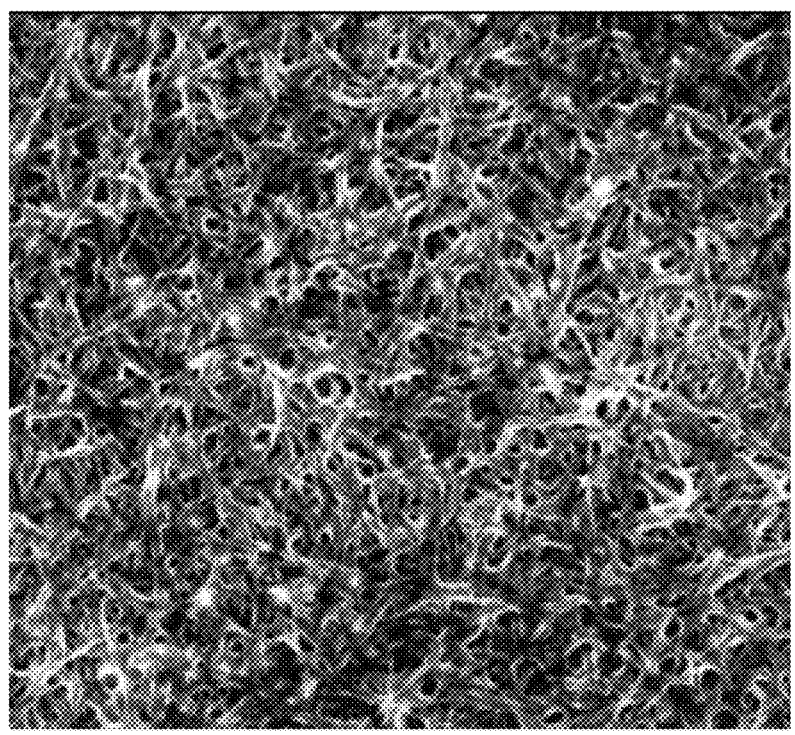
FIG. 1A illustrates a scanning electron microscope (SEM) image of a sensor compound, in accordance with some examples of the current disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a nanofiber" includes reference to one or more of such materials and reference to "subjecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, "substituted" refers to the substitution of a carbon and/or hydrogen atom in a linear aliphatic, branched aliphatic, or aryl group for a non-carbon or non-hydrogen group, respectively. The specific substituents can be different or the same at each substituted position. There is not intended to be any specific limitation to the particular substituted that can be used in the sensor compounds described here. As one non-limiting example, one or more carbon atoms can be replaced with one or more suitable alternative atoms, such as a nitrogen, oxygen, sulfur, boron, phosphorous, other suitable atoms, or a combination thereof. Similarly, one or more hydrogen groups can be substituted with one or more suitable atoms or functional groups, such as a halide, an oxygen, a nitrogen or amino, a methyl, a hydroxyl, a carboxyl, and the like. Thus, "unsubstituted" refers to a linear aliphatic, branched aliphatic, or aryl group where none of the carbons and hydrogens have been substituted.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

With these definitions in mind, the current disclosure is directed to sensor compounds and associated methods and devices. The sensor compounds can be used to detect a variety of target analytes. In one particular example, the sensor compounds can be used to detect a non-explosive analyte. As used herein, "explosive analyte" refers to a compound that is typically considered or associated with a high explosive (e.g. nitramine explosives, nitrate based explosives, peroxide based explosives, etc). A "high explosive," as used herein, generally refers to a compound that has a burn rate of at least 2 kilometers per second (km/s). In one specific example, an "explosive analyte" can be or include nitromethane, dinitrotoluene (DNT), trinitrotoluene (TNT), ammonium nitrate fuel oil (ANFO), ammonium nitrate, pentaerythritol tetranitrate (PETN), Research Department Explosive (RDX), triacetone triperoxide (TATP), nitroglycerin, ethylene glycol dinitrate, nitromethane, picric acid, derivatives thereof, or combinations thereof. Thus, a "non-explosive analyte" refers to a compound that is not an "explosive analyte."

Non-explosive analytes can include various categories of analytes. For example, a non-explosive analyte can include toxic industrial chemicals, volatile organic compounds (VOCs), amine-containing compounds, chemical warfare agents, food safety chemicals, fuels, propellants, alcohols (e.g. ethanol), ketones (e.g. acetone), sulfides, thiols, the like, or combinations thereof. More specifically, toxic industrial chemicals can include chemicals such as chlorine gas, ammonia, hydrogen peroxide, sulfur dioxide, hydrochloric acid, triethyl phosphate, phosphine, hydrogen cyanide, arsine, formaldehyde, the like, and combinations thereof. VOCs can include chemicals such as benzaldehyde, hexane, acetone, ethanol, diesel fuel, nitrobenzene, formaldehyde, the like, and combinations thereof. Amine-containing compounds can include chemicals such as N-methyl phenethylamine, methylamine, ammonia, aniline, triethylamine, diethylamine, the like, and combinations thereof. Chemical warfare agents can include, but are not limited to, chemicals such as triethylphosphate, 2-choroethyl ethyl sulfide, dimethyl methylphosphonate (DMMP), triphosgene, nerve agents (e.g. Tabun, Sarin, Soman Cyclosarin, and methylphosphonothioic acid, etc), blister agents (e.g. sulfur mustards such as bis(2-chloroethyl) sulfide, nitrogen mustards, lewisite, phosgene oximine, etc.), choking agents (e.g. phosgene, diphosgene, triphosgene, chlorine, chloropicrin, etc), the like, and combinations thereof. Food safety chemicals can include trichloroanisole, melamine, trimethylamine, the like, and combinations thereof. It is noted that these lists of non-explosive analytes are not intended to be limiting, but are merely provided as examples of compounds that can be detected via the current method. More generally, the sensor compounds described here can be used to detect a variety of fluids, generally in the vapor state. Non-limiting examples of classes of compounds which may be detected include an amine, a phosphine, a peroxide, an aliphatic hydrocarbon, an aromatic hydrocarbon, a phenolic compound, an alcohol, a thiol, an acid, other compound acting as a reductant, or a combination thereof.

More specifically, a target analyte, such as a non-explosive analyte, can be detected by exposing a sensor compound described herein to the target analyte. This can cause or facilitate a change in the sensor compound upon exposure of the sensor compound to the non-explosive analyte. The change can then be displayed to indicate to a user that a target analyte has been sensed. For example, the sensor compounds described herein are typically of n-type semiconductor, where the major charge carriers are electrons, resulting in an electrically conductive material. Thus, in some examples, various sensor compounds described herein can initially exhibit photocurrent, which is then increased following the adsorption of analytes that are capable of donating electrons (reductants). In other examples, various sensor compounds described herein can initially exhibit no photocurrent which is then present following the adsorption of a target analyte. In yet other examples, adsorption of analytes do not donate or withdraw (reduce or oxidize) electrons, such as aliphatic or aromatic hydrocarbons, which can decrease the inherent photocurrent of various sensor compounds, likely by altering the pi-pi stacking of the nanostructure of the sensor compound. In yet other examples, peroxides can function as oxidants resulting in a decrease in photocurrent in various sensor compounds. In additional examples, various sensor compounds can detect HCl gas, which can cause a decrease in photocurrent.

In other examples, the sensory materials can experience a detectable change in electrical conductivity upon exposure to a target analyte without inducing a photocurrent via a light source. This can occur via interfacial charge transfer between the target analyte and the sensory material. Thus, a change (increase or decrease) in conductivity in the sensor compound can be detected upon exposure of the sensor compound to the target analyte whether the detection environment is dark or illuminated.

In other examples, the sensor compound can be a fluorescent sensor compound. Where this is the case, detection can generally be based on quenching of the fluorescence emission of the sensor compound upon interaction of with the target analyte. A corresponding fluorescence detector can be used to detect fluorescence and a computing module can be used to correlate detected fluorescence with a corresponding analyte concentration based on predetermined references.

Typically, the sensor compound can be a compound having one of three general structural formulas. In one example, the sensor compound can be compound having a structure according to Formula I:

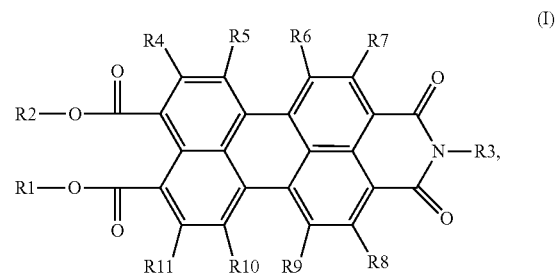

where R1, R2, and R3 are independently chosen from $C_1$-$C_{20}$ substituted or unsubstituted linear aliphatic groups, branched aliphatic groups, cyclic groups, and aryl groups, or combinations thereof, and where R4-R11 are independently chosen from hydrogen, halides, carboxyl groups, hydroxyl groups, nitrile groups, $C_1$-$C_8$ alkyl groups, and combinations thereof. The diester-monoimides of Compound I are typically a precursor and intermediate compound used to prepare PTCDI compounds of Compound II shown below.

The R1 and R2 groups can generally be selected to facilitate the transfer of electrons to the perylene backbone structure upon interaction with a non-explosive analyte. This can be achieved via any of the detection modes described above (i.e. change in photocurrent, change in electrical conductivity, fluorescence quenching, etc.) In some examples, R1 and R2 can be the same as one another. In other examples, R1 and R2 can be different from one another. For example, in structure I.01 R1 and R2 are the same, whereas in structure I.02 R1 and R2 are different.

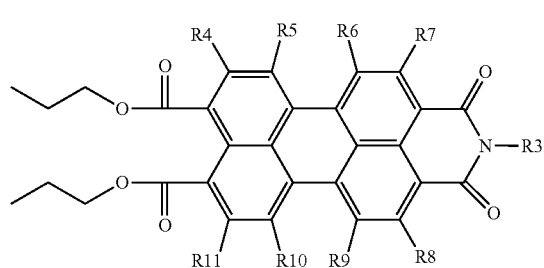
(I.01)

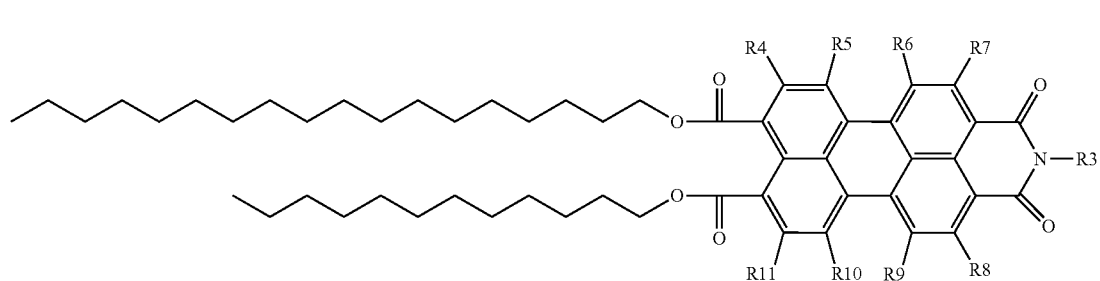
(I.02)

In some specific examples, R1, R2, or both can be a $C_2$-$C_6$ substituted or unsubstituted linear or branched aliphatic group. This can be illustrated in structures I.01 above and I.03 below, for example.

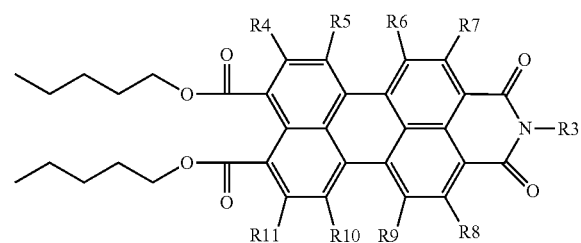
(I.03)

R3 can generally be a morphology control group, but can also be an electron donor group to help facilitate transfer of electrons to the perylene backbone upon interaction with a non-explosive analyte, or a combination thereof. In some examples, the R3 group can be a morphology control group. As such, selection of a particular morphology control group can affect how the sensor compound assembles as a nanostructure. For example, where R3 is a linear aliphatic group having nine or more carbons, the sensor compound can tend to arrange as a nanobelt. Thus, structure I.04 below can generally have a nanobelt arrangement when formed into a nanostructure.

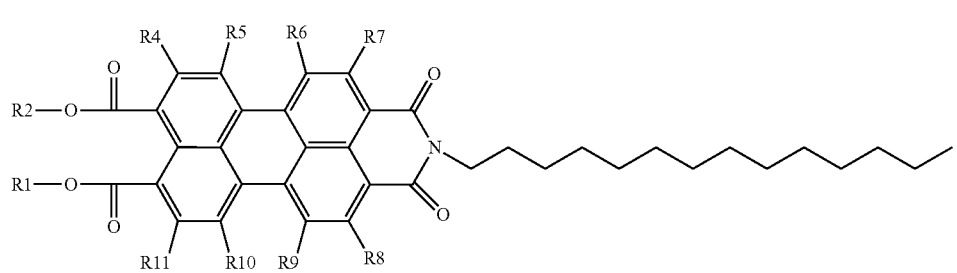
(I.04)

Other R3 groups can tend to provide nanotube structures or nanofiber structures. For example, in some cases, structure I.05 can tend to form a nanofiber arrangement when formed into a nanostructure.

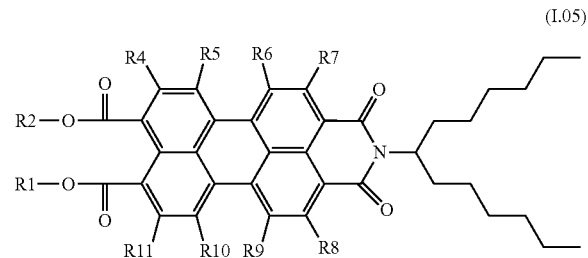
(I.05)

Thus, a broad variety of R3 groups can be employed in the sensor compound. In some examples, where the R3 group is a linear aliphatic group, the R3 group can include ethyl, butyl, hexyl, heptyl, octyl, nonyl, decyl, undecyl, dodecyl, tridecyl, tetradecyl, pentadecyl, hexadecyl, or other linear aliphatic groups. Where the R3 group is a branched aliphatic group, the R3 group can include hexaheptyl, pentylhexyl, butylpentyl, butyloctyl, or other branched aliphatic groups. Whether the R3 group is linear, branched, or cyclic, in some examples, one or more carbon groups can be substituted with an oxygen group to form a mono- or polyether chain, such as structure I.06 below, for example.

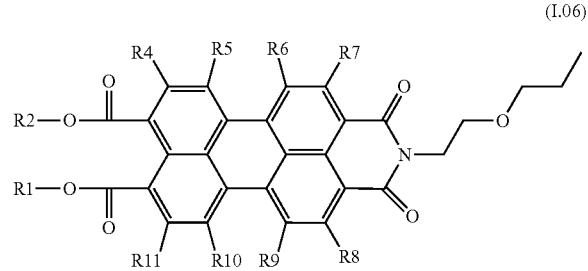
(I.06)

In other examples, one or more carbon groups can be substituted with a nitrogen group to form a nitrile group, a primary, secondary, or tertiary amine, or an amide, such as in structure I.07, for example.

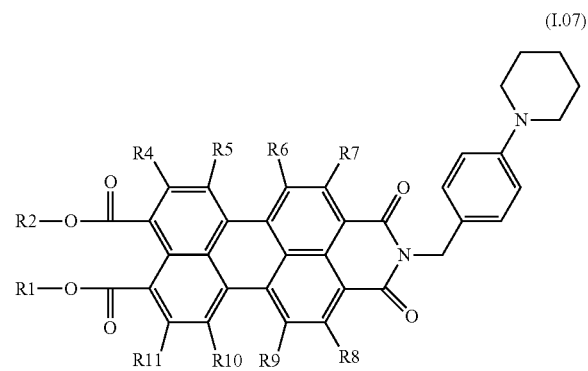
(I.07)

In other examples, one or more carbon groups can be substituted with a sulfur group or other desirable substituent. In one specific example, R3 can be a $C_8$-$C_{16}$ substituted or unsubstituted linear or branched aliphatic group, such as structures I.05 and I.06, for example.

R4-R11 can typically be solubilizing groups, but in some cases can also be electron donating groups. Generally, any group can be used for R4-R11 that does not significantly diminish the selectivity and sensitivity of the sensor compound. In some examples, R4-R11 can include hydrogen, a halide, a carboxyl group, a hydroxyl group, a nitrile group, a $C_1$-$C_8$ alkyl group, the like, or a combination thereof. In some examples, at least one of R4-R11 is not hydrogen. In some examples, each of R4-R11 is hydrogen. In some examples, at least two of R4-R11 is a halide, a carboxyl group, a hydroxyl group, a nitrile group, a $C_1$-$C_8$ alkyl group, or a combination thereof. This can be illustrated in structures I.08 and I.09 below, for example.

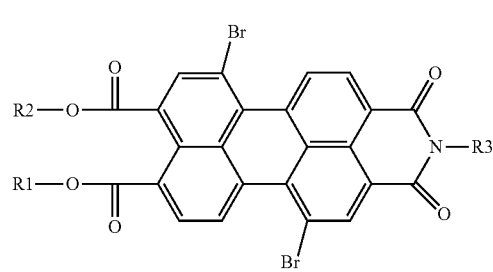
(I.08)

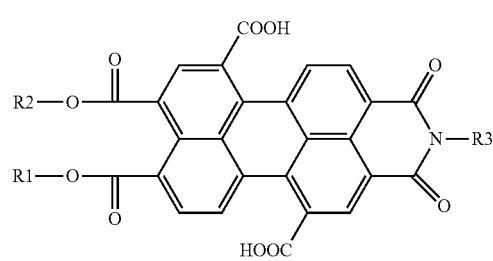
(I.09)

In one specific example, the sensor compound can have structure I.10 or equivalent.

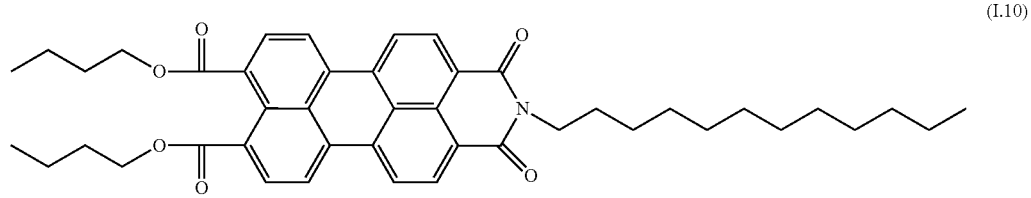 [SMILES: CCCCCCCCCCCCN1C(=O)c2ccc3c4ccc(C(=O)OCCCC)c5c(C(=O)OCCCC)ccc(c6ccc(c2c36)C1=O)c54]

(I.10)

Other sensor compounds can also be used in the method of detecting a non-explosive analyte, such as those having a structure according to Formula II:

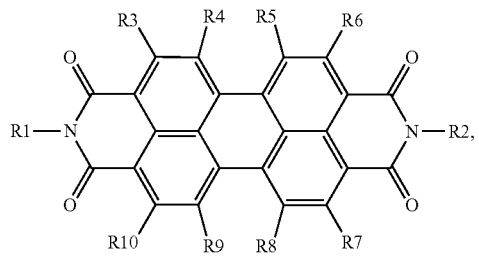

(II)

where R1 and R2 are independently chosen from $C_1$-$C_{20}$ substituted or unsubstituted linear aliphatic groups, branched aliphatic groups, cyclic groups (including heterocyclic groups), and aryl groups, and where R3-R10 are independently chosen from hydrogen, halides, carboxyl groups, hydroxyl groups, nitrile groups, $C_1$-$C_8$ alkyl groups, and combinations thereof.

R1 and R2 can typically be one or more of electron donating groups, morphology control groups, or selectivity enhancing groups. In some examples, R1 and/or R2 can be a morphology control group. Suitable electron donating groups can act as an internal dopant to aid in generation of photocurrent. Suitable selectivity enhancing groups can contain hydrophobic regions, hydrophilic regions, hydrogen binding sites, electrostatic sites, metal ligands, or the like based on the desired target analyte. While either R1 or R2 or both can be a morphology control group, specific reference will be made to R1 for the sake of brevity and clarity. Morphology control groups can also aid in self-assembly of these PTCDI compounds into nanofibers through hydrophobic, van der Waals, π-π stacking, and/or hydrogen bonding interactions. Regardless, where R1 is a morphology control group, R1 can typically be a $C_1$-$C_{20}$ substituted or unsubstituted linear or branched aliphatic group, or aryl group, such as structures II.01, II.02, and II.03 below, for example.

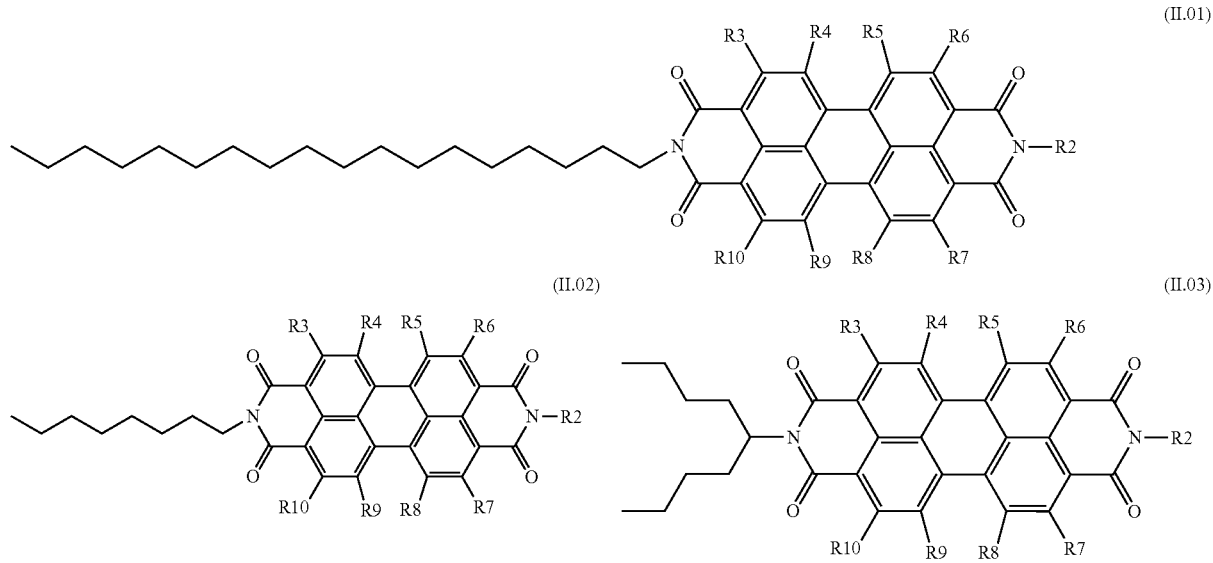

Numerous other R1 groups are also possible, such as those described above with respect to the R3 group for the Formula I structures. For example, where the R1 group of Formula II is a linear aliphatic group, the R1 group can include ethyl, butyl, hexyl, heptyl, octyl, nonyl, decyl, undecyl, dodecyl, tridecyl, tetradecyl, pentadecyl, hexadecyl, or other suitable linear aliphatic group. Where the R1 group is a branched aliphatic group, the R1 group can include hexaheptyl, pentylhexyl, butylpentyl, butyloctyl, or other suitable branched aliphatic group. Whether the R1 group is linear, branched, or cyclic, in some examples, one or more carbon groups can be substituted with an oxygen group to form a mono- or polyether chain, can be substituted with a nitrogen group to form a nitrile group, a primary, secondary, or tertiary amine, or an amide, or can be substituted with any other suitable substituent. In some specific examples, R1 can be a $C_4$-$C_{16}$ substituted or unsubstituted linear or branched aliphatic group. In some examples, R1 can be a substituted or unsubstituted linear aliphatic group. In other examples, R1 can be a substituted or unsubstituted branched aliphatic group. In some examples, whether R1 is linear, branched, or aryl, at least one hydrogen group can be substituted with a halide, such as fluorine, chlorine, bromine, etc. In one specific example, the halide can be fluorine and the R1 can be perfluorinated, such as in structure II.04 below.

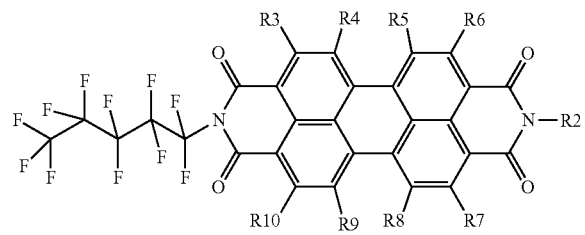

(II.04)

In some examples, R1 and/or R2 can be an electron donating group. While R1 or R2 or both can be an electron donating group, specific reference will be made to R2 for the sake of brevity and clarity. Thus, where R2 is an electron donating group, R2 can typically be a $C_1$-$C_{20}$ substituted or unsubstituted linear aliphatic group, branched aliphatic group, or aryl group. The electron donating group can typically include any group that sufficiently facilitates the transfer of an electron from the electron donating group to the perylene tetracarboxylic diimide (PTCDI) backbone upon exposure to a non-explosive analyte. As described above, this electron transfer can cause a detectable change in the sensor compound, such as via fluorescence quenching, change in conductivity of the chemical sensor, change in photocurrent across the chemical sensor, etc.

Thus, a broad range of electron donating groups can be employed in the chemical sensor of Formula II. In some examples, R2 can be a $C_1$-$C_{20}$ substituted or unsubstituted linear or branched aliphatic group, an alkylbenzene group, a heterocycle, an aryl compound having an oxygen-containing side group, an aryl compound having a nitrogen-containing side group, an aryl compound having a sulfur-containing side group, or a combination thereof.

As non-limiting examples, where R2 is a $C_1$-$C_{20}$ substituted or unsubstituted linear or branched aliphatic group, the sensor compound can have a structure according to those listed for R1 in structures II.01-II.04 above. Other non-limiting examples of $C_1$-$C_{20}$ substituted or unsubstituted linear or branched R2 groups are illustrated in the following structures:

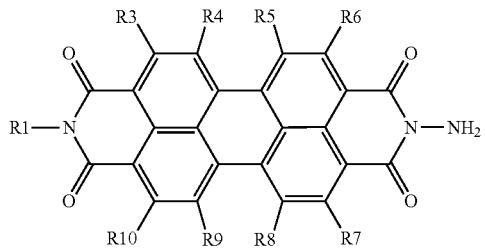

(II.05)

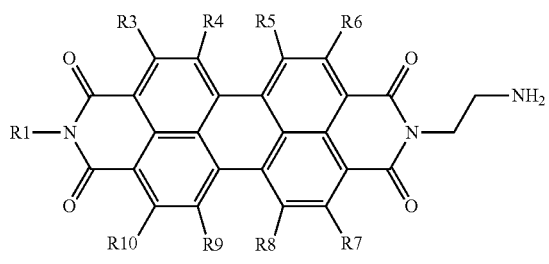

(II.06)

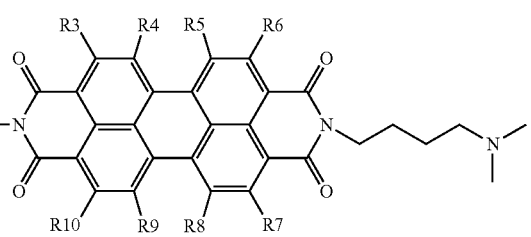

(II.07)

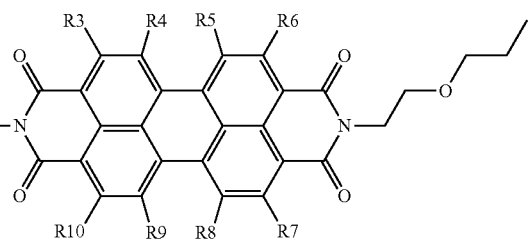

(II.08)

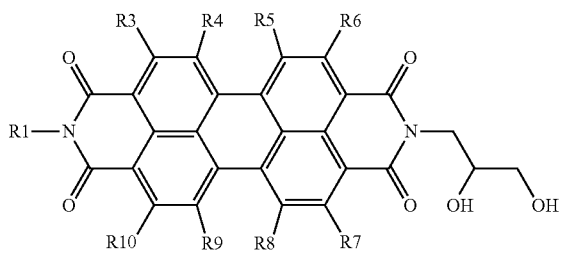

(II.09)

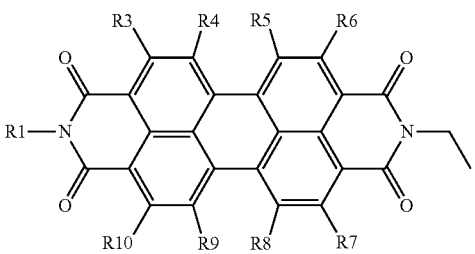

(II.10)

-continued

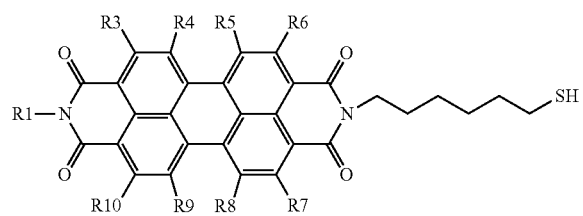
(II.11)

As will be appreciated by one skilled in the art, numerous other $C_1$-$C_{20}$ substituted or unsubstituted linear or branched aliphatic R2 groups can also be employed in Formula II in addition to those illustrated in structures II.05-II.11.

In other examples, R2 can include an alkylbenzene group. Alkylbenzene groups can include one or more alkyl groups attached to a benzene ring, such as, for example:

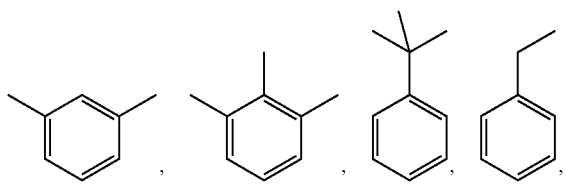

or combinations thereof. Such groups act as selectivity enhancing groups. Generally, such selectivity enhancing groups can be characterized by the following general formulas:

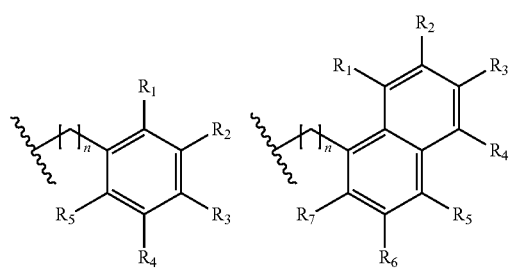

where R1 through R7 are either hydrogen, straight chain, cyclic, or aromatic hydrocarbons of 18 carbons or less, and n ranges from 0 to 18 carbons.

In yet other examples, R2 can include a heterocycle. Heterocycles can include any cyclical compound where a carbon atom has been substituted with a non-carbon atom. Non-limiting examples can include:

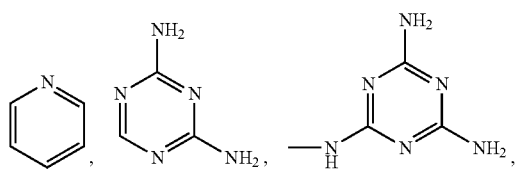

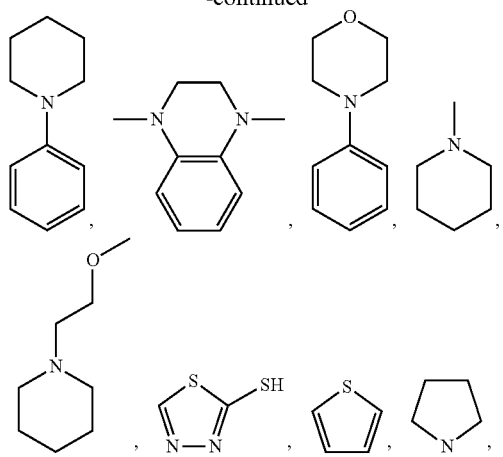

or combinations thereof.

In other examples, R2 can include an aryl compound having an oxygen-containing side group, such as, for example:

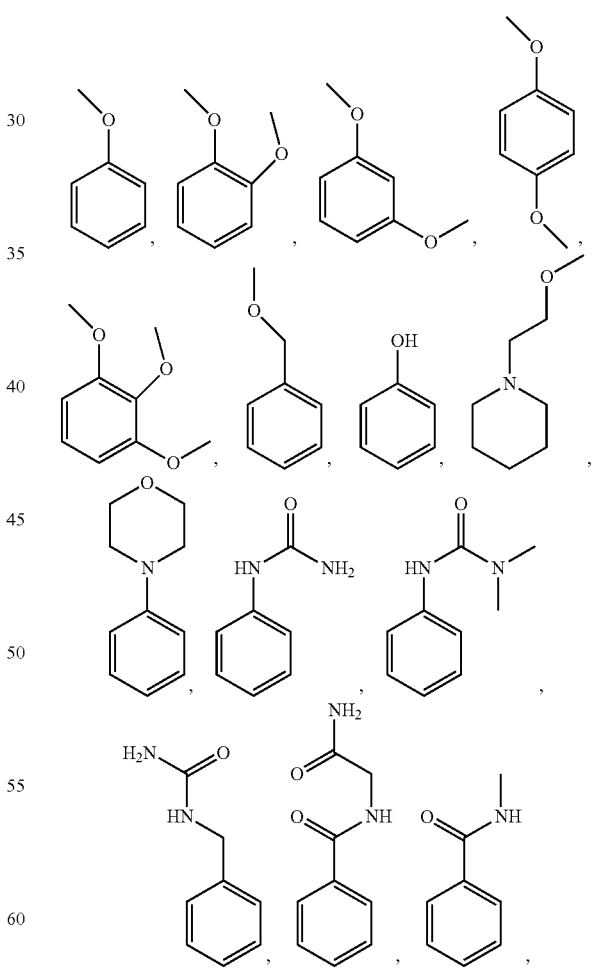

or combinations thereof.

In some other examples, R2 can include an aryl compound having a nitrogen-containing side group, such as, for example:

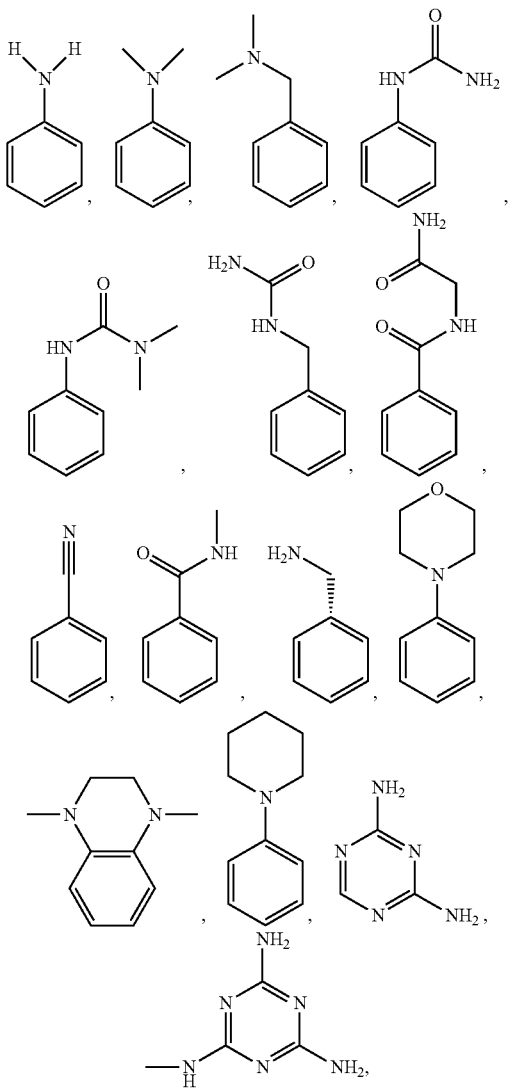

or combinations thereof.

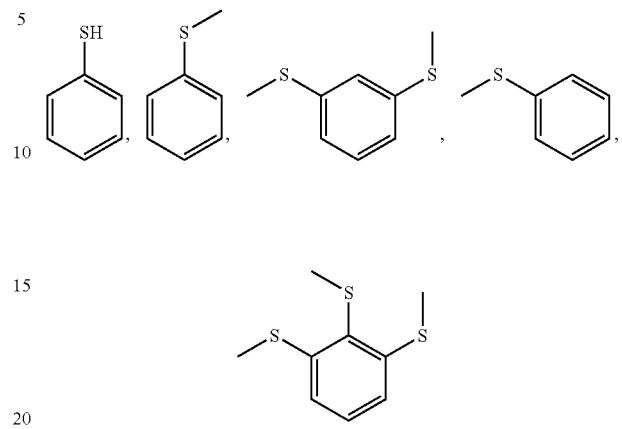

or combinations thereof.

In additional examples, R2 can include an aryl compound having a sulfur-containing side group, such as, for example:

Thus, the R2 group of Formula II can include a wide variety of functional groups, including a combination of the different groups listed above. It is also noted that any functional group described with respect to R1 can also be included at R2, and vice versa.

R3-R10 can typically be solubilizing groups, but in some cases can also be electron donating groups. Generally, any group can be used for R3-R10 that does not significantly diminish the selectivity and sensitivity of the sensor compound. In some examples, R3-R10 can include hydrogen, a halide, a carboxyl group, a hydroxyl group, a nitrile group, a $C_1$-$C_8$ alkyl group, the like, or a combination thereof. In some examples, at least one of R3-R10 is not hydrogen. In some examples, each of R3-R10 is hydrogen. In some examples, at least two of R3-R10 is a halide, a carboxyl group, a hydroxyl group, a nitrile group, a $C_1$-$C_8$ alkyl group, or a combination thereof.

Non-limiting specific examples of chemical sensor compounds having a structure according to Formula II can include:

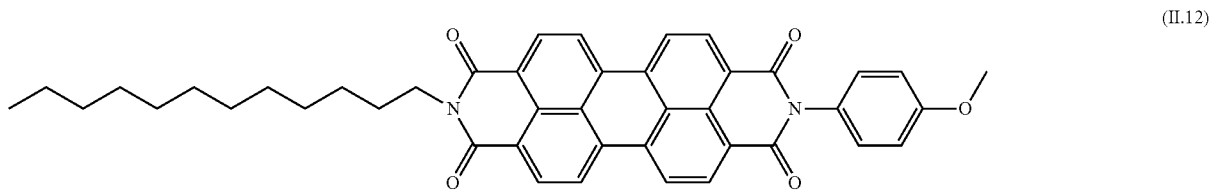
(II.12)

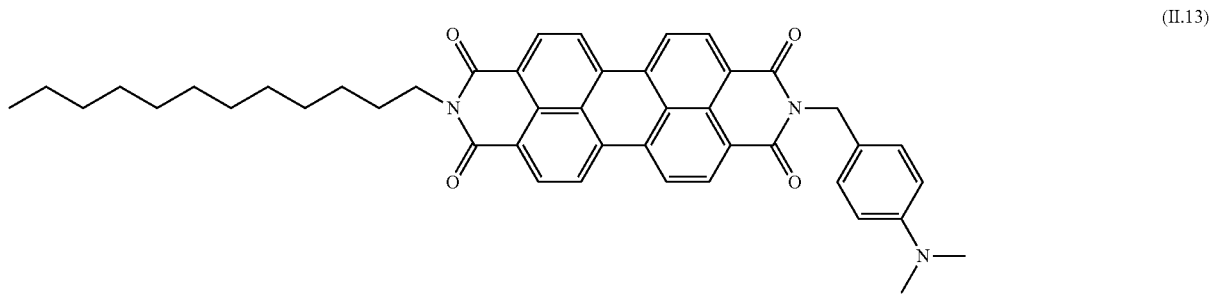
(II.13)

-continued
(II.14)
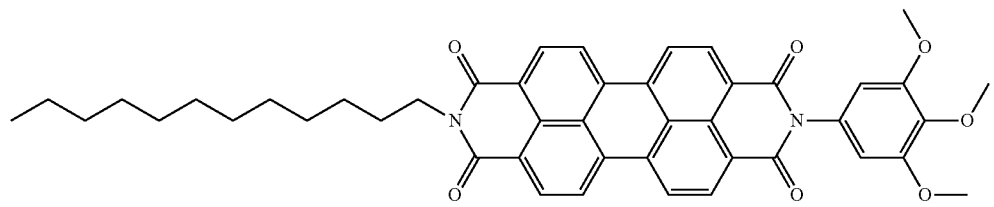
(II.15)
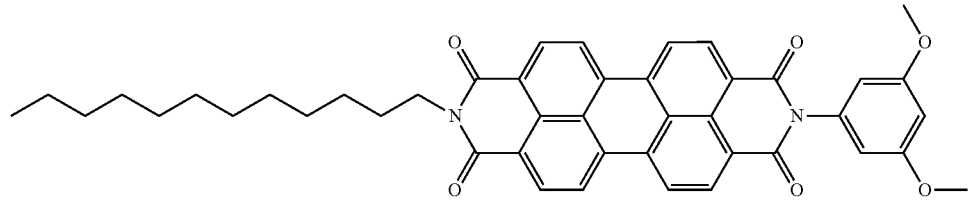
(II.16)
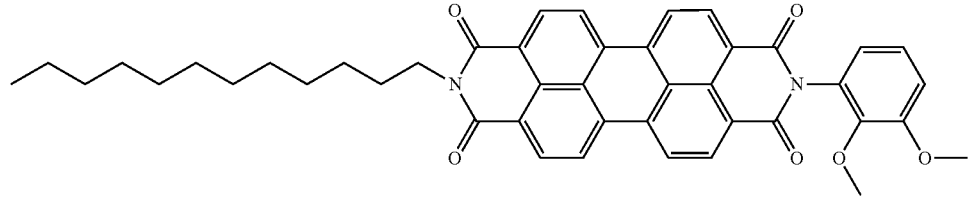
(II.17)
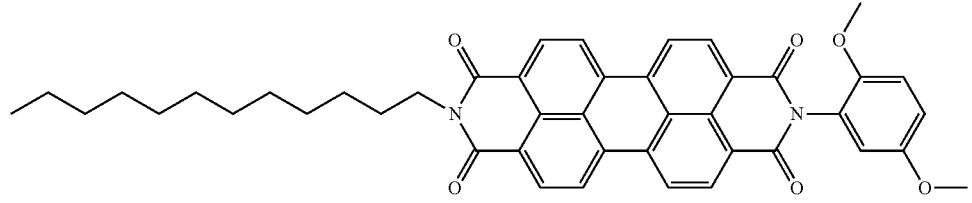
(II.18)
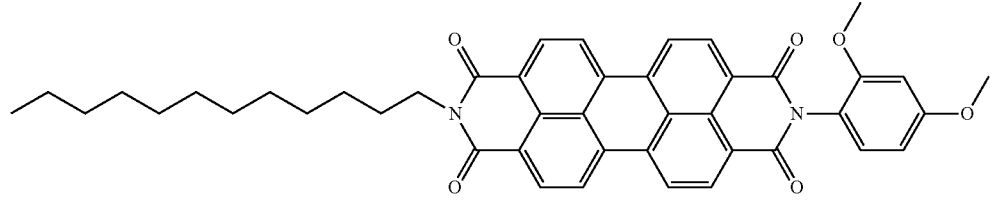
(II.19)
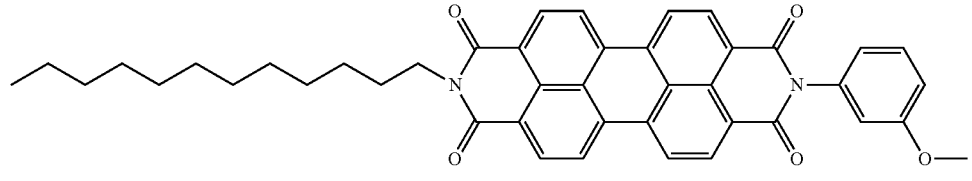
(II.20)
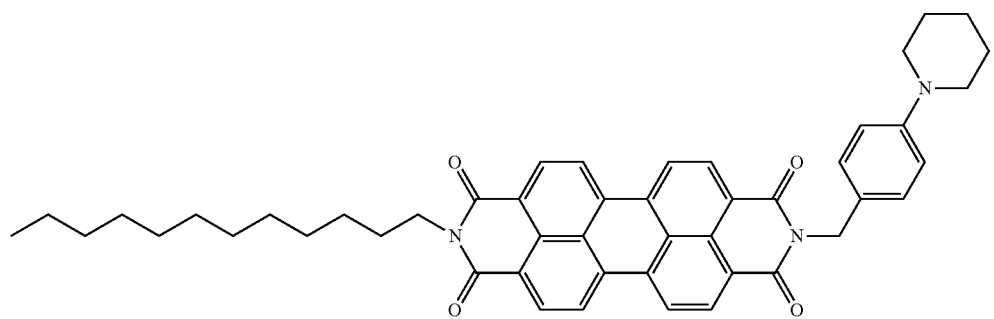

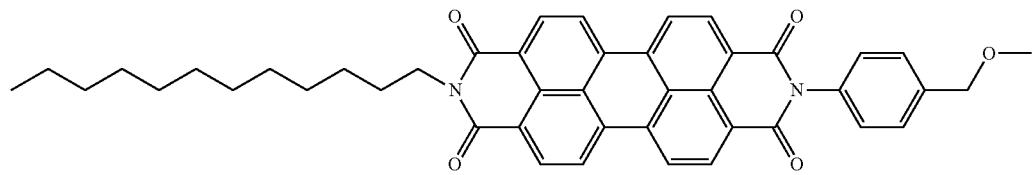
(II.21)
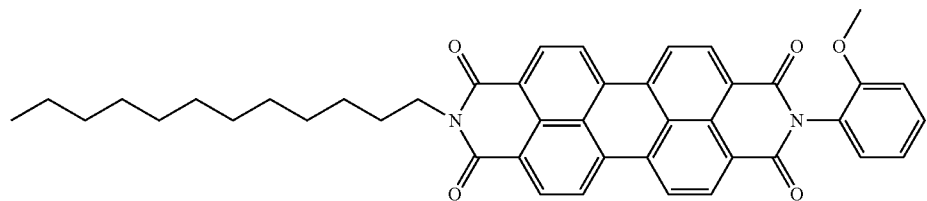
(II.22)
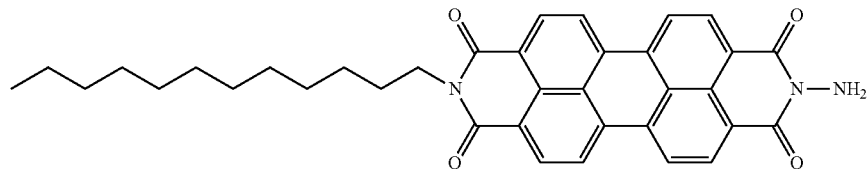
(II.23)
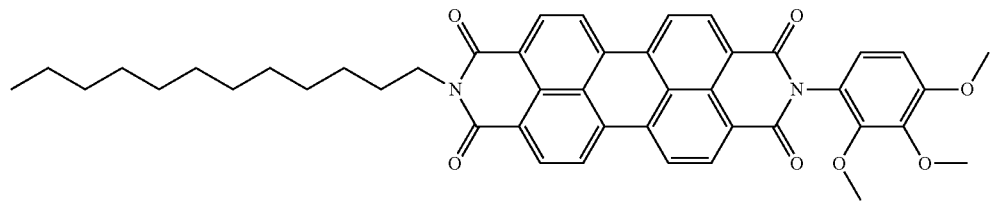
(II.24)
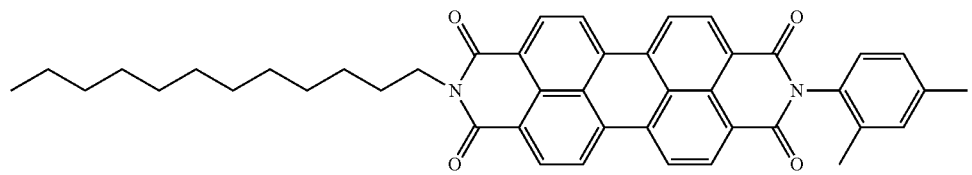
(II.25)
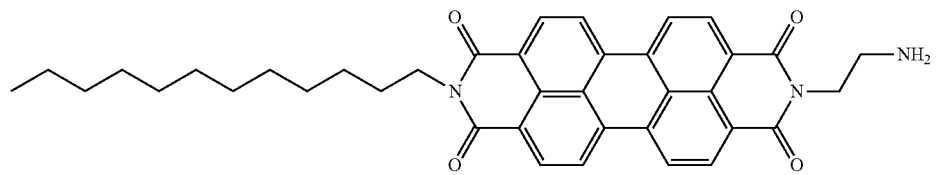
(II.26)
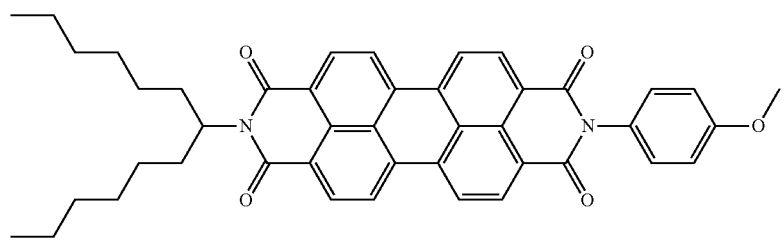
(II.27)
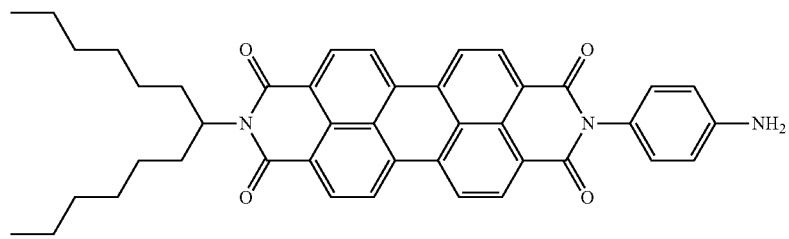
(II.28)

(II.29)
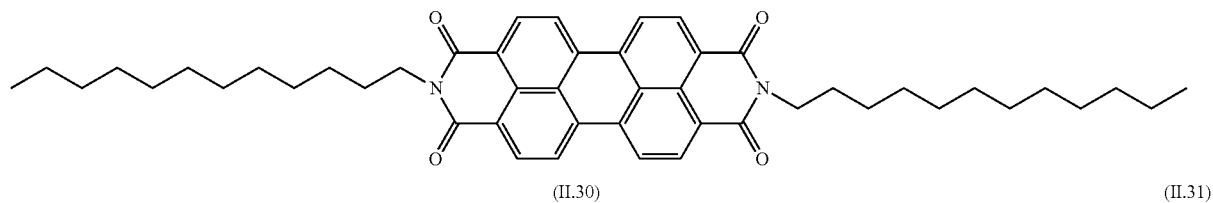
(II.30)
(II.31)
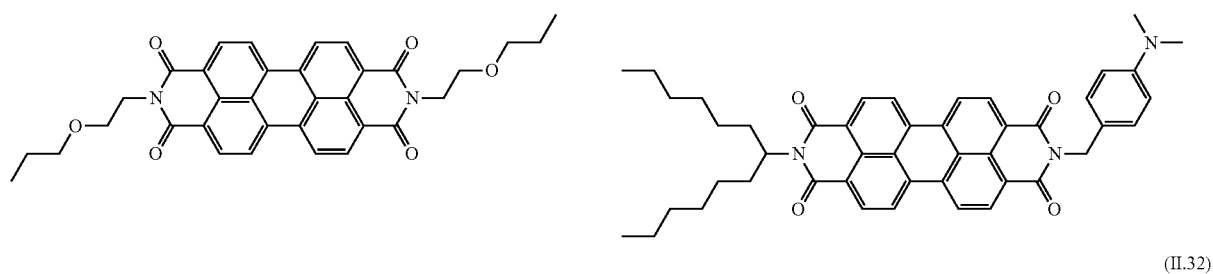
(II.32)
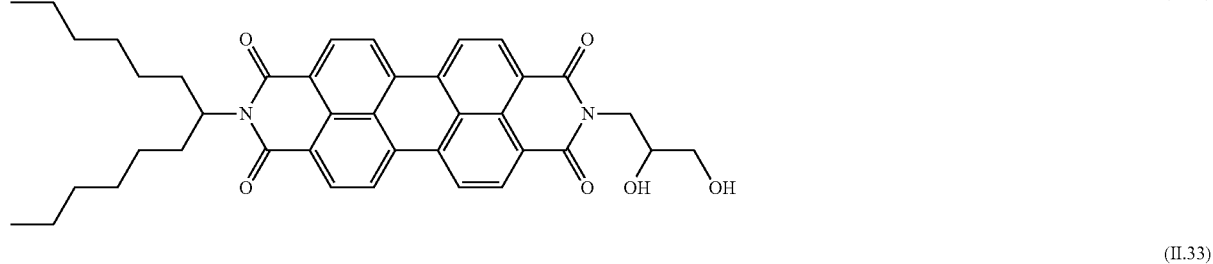
(II.33)
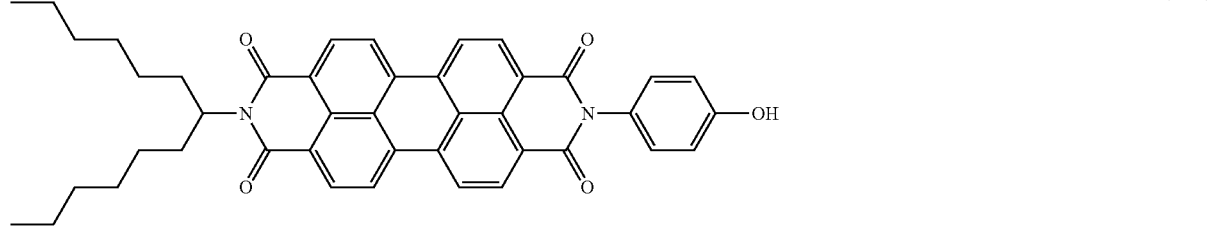
(II.34)
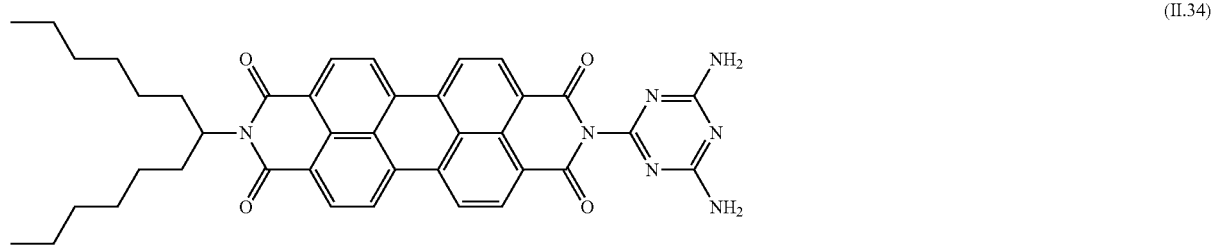
(II.35)
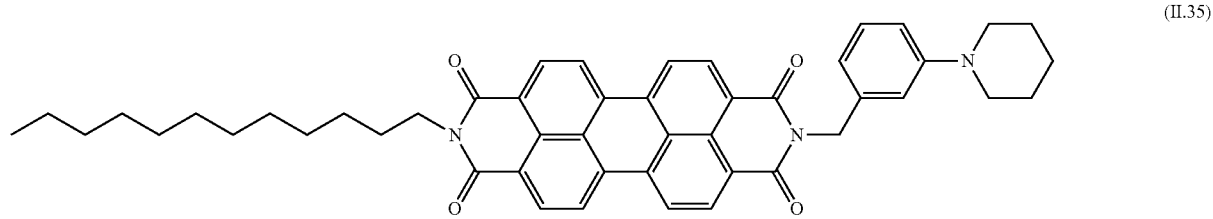

-continued
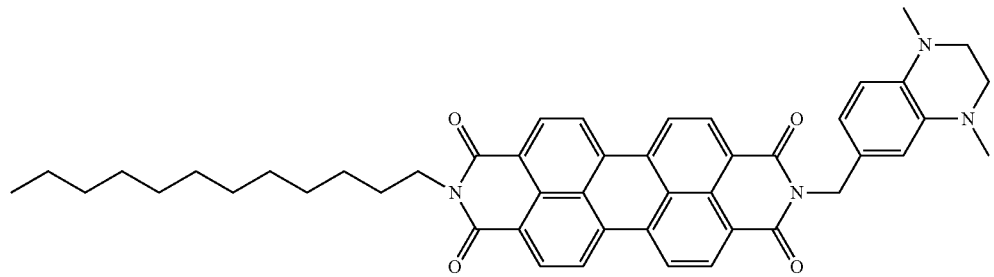
(II.36)
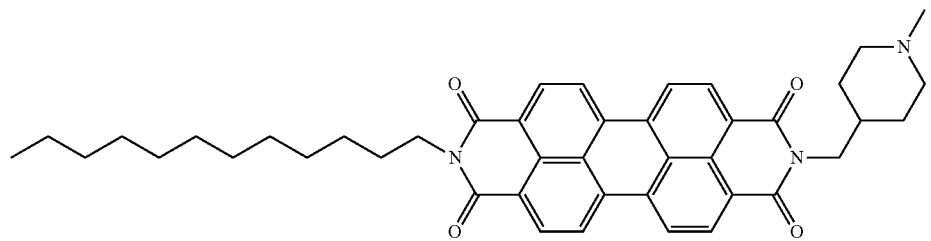
(II.37)
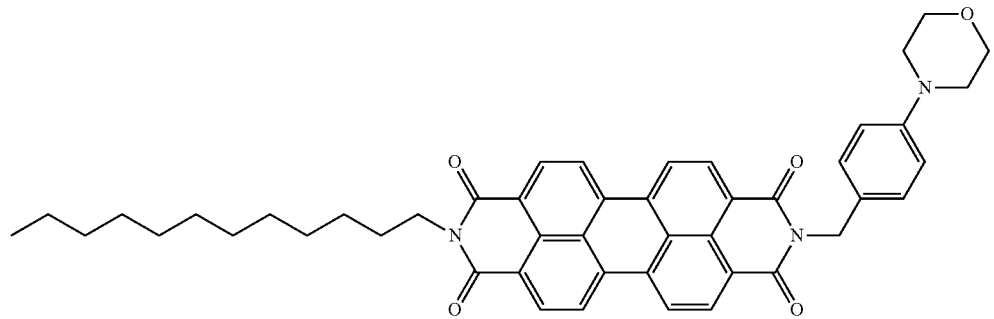
(II.38)
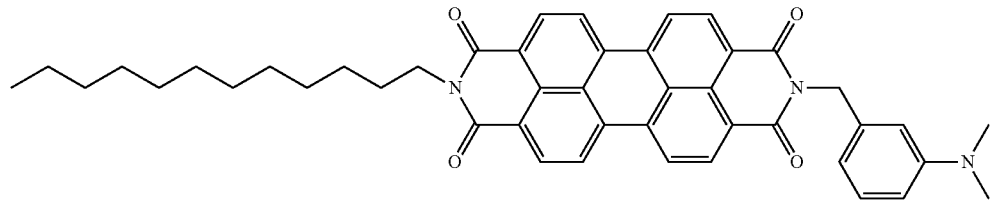
(II.39)
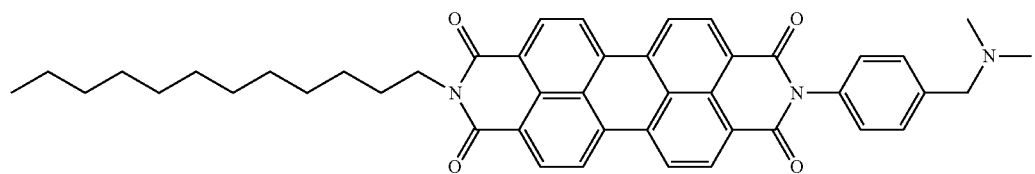
(II.40)
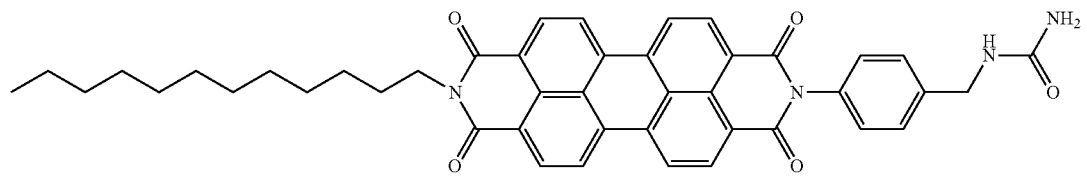
(II.41)

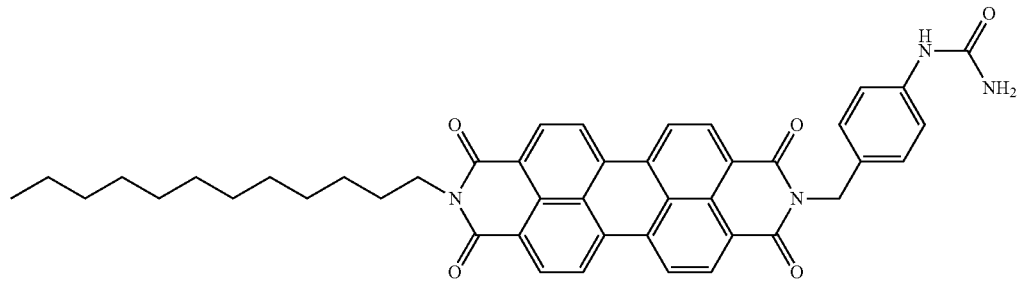
(II.42)
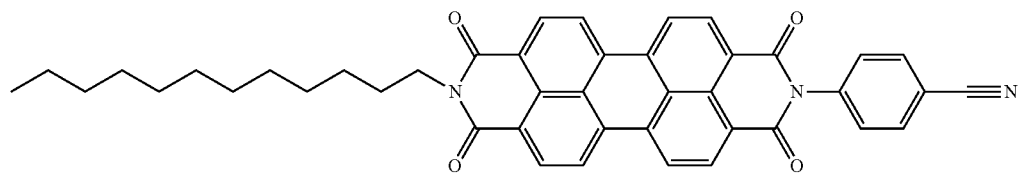
(II.43)
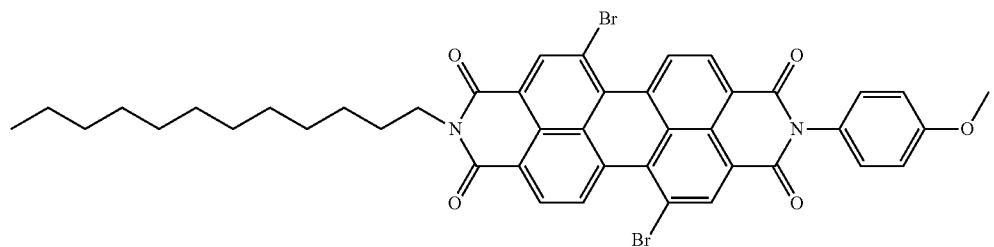
(II.44)
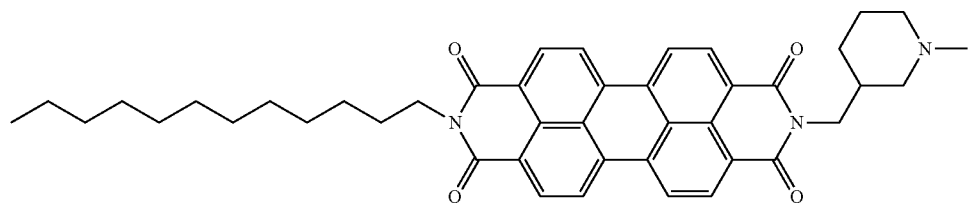
(II.45)
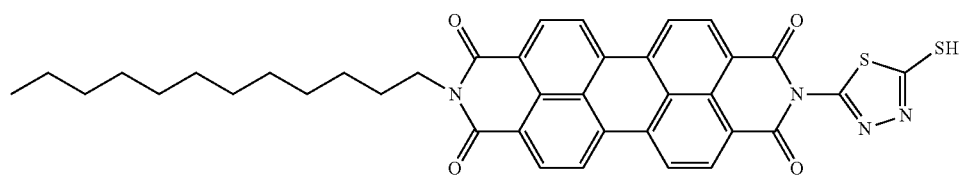
(II.46)
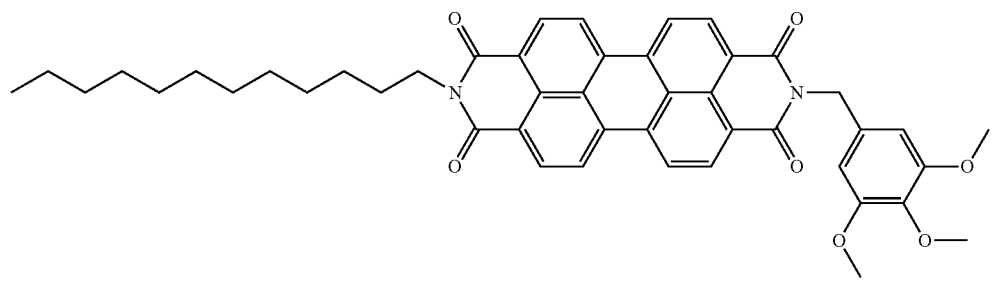
(II.47)
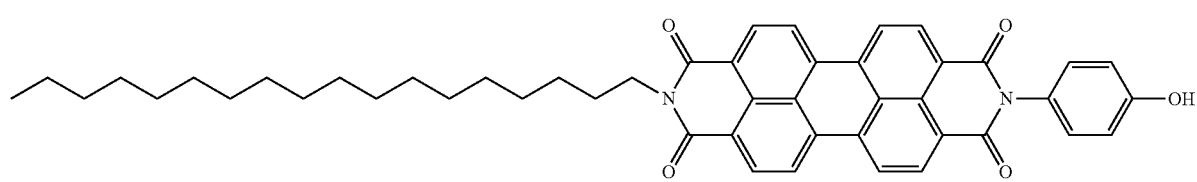
(II.48)

(II.49)
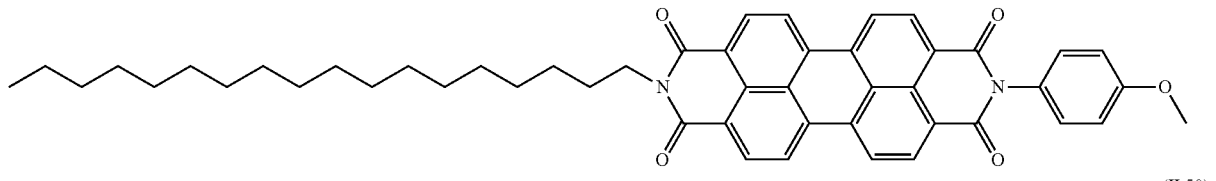
(II.50)
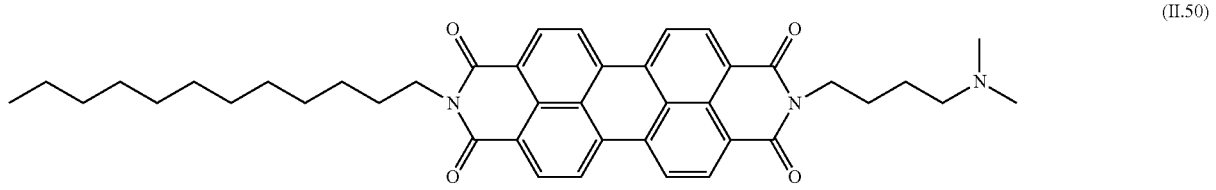
(II.51)
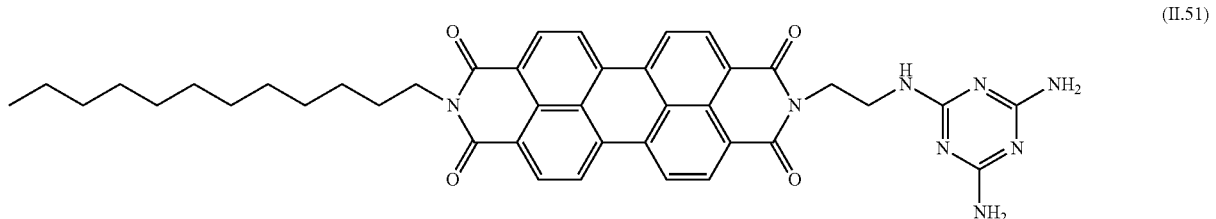
(II.52)
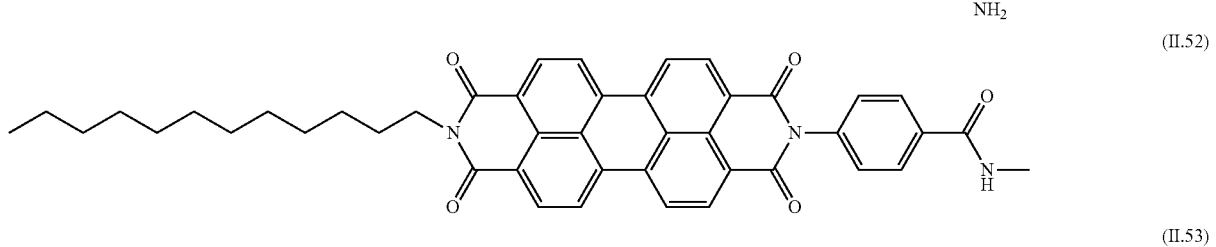
(II.53)
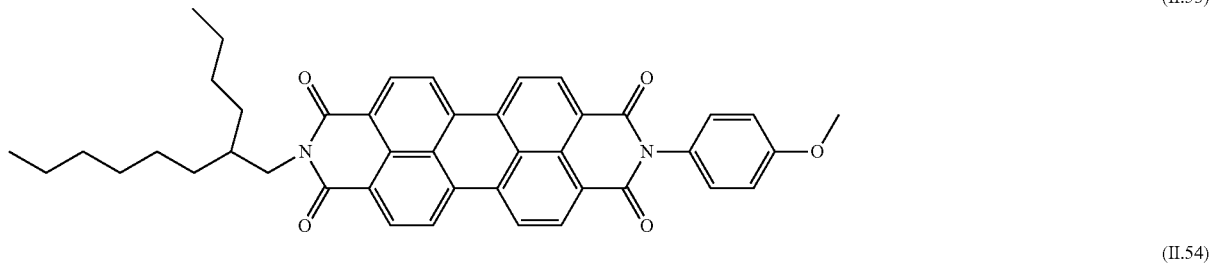
(II.54)
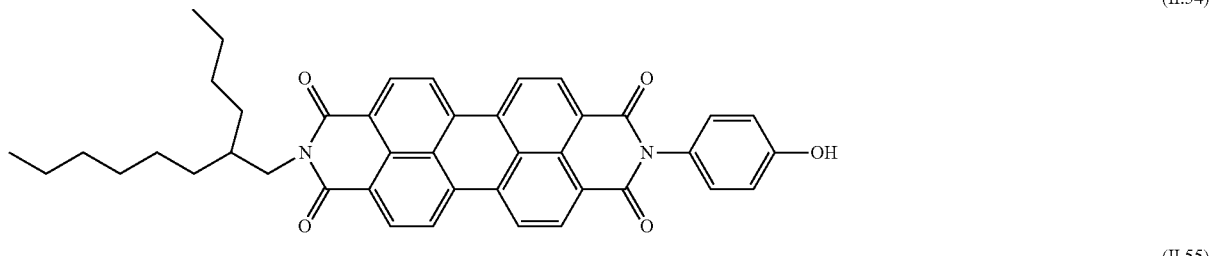
(II.55)
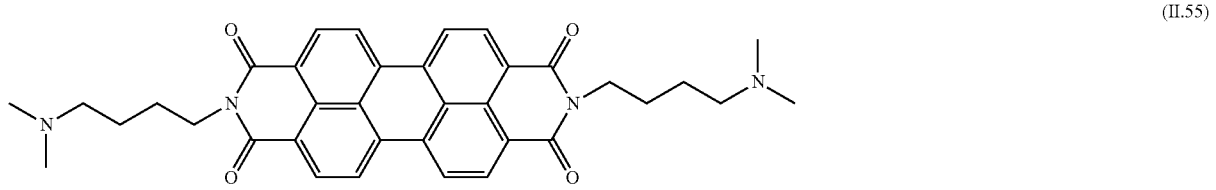
(II.56)
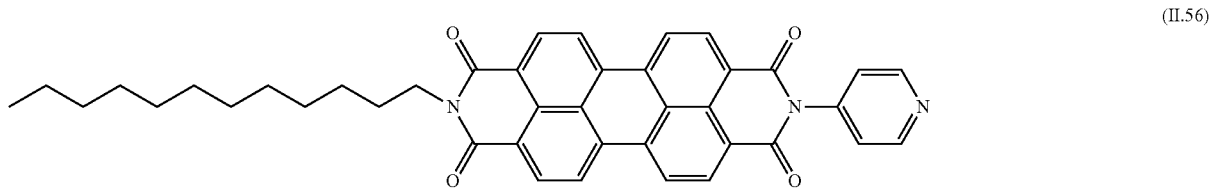

-continued
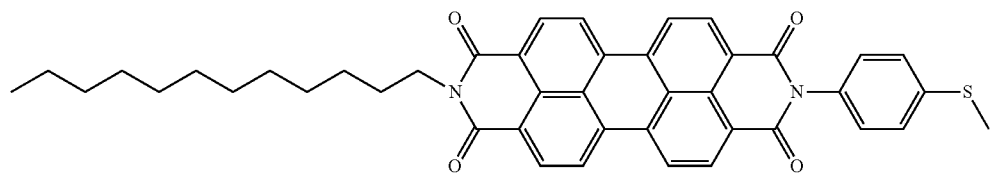
(II.57)
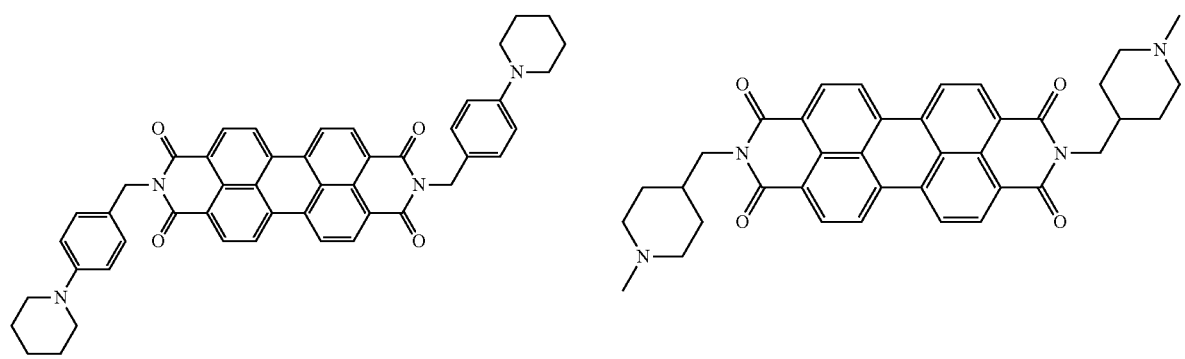
(II.58) (II.59)
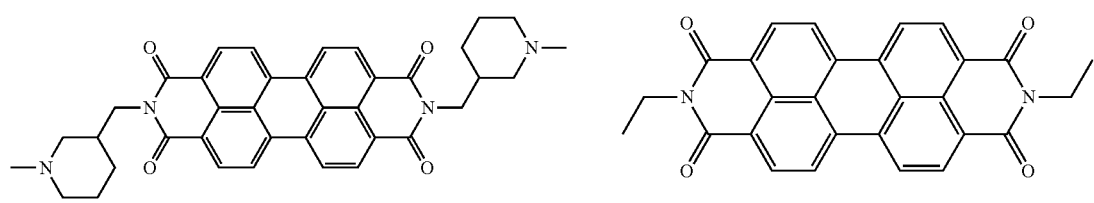
(II.60) (II.61)
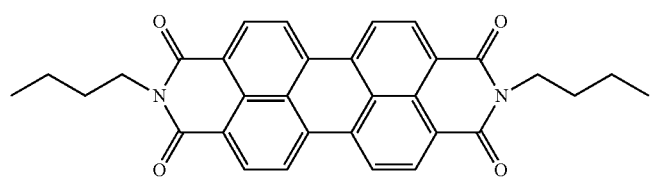
(II.62)
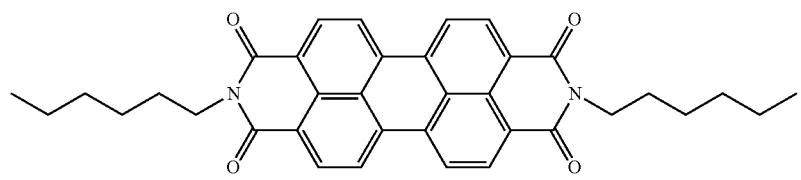
(II.63)
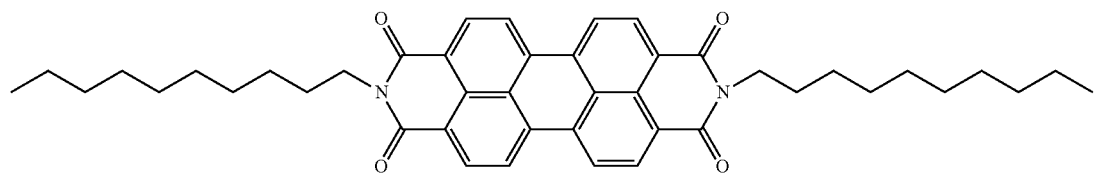
(II.64)
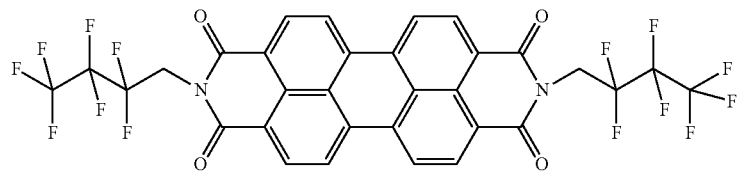
(II.65)

-continued
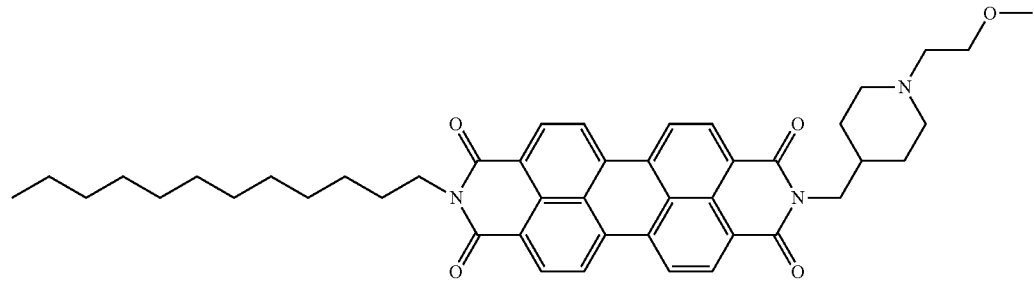
(II.66)
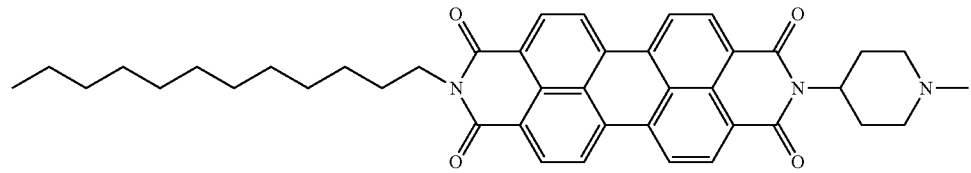
(II.67)
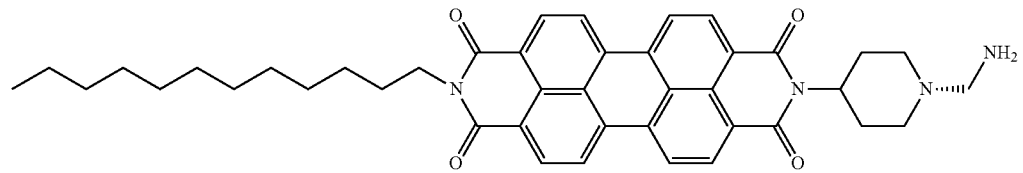
(II.68)
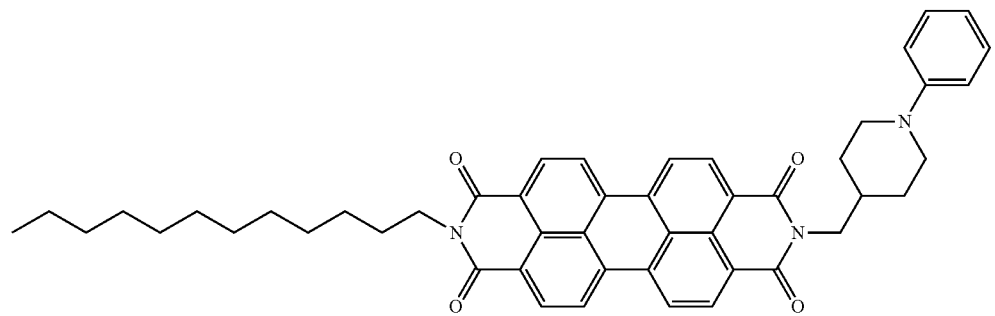
(II.69)
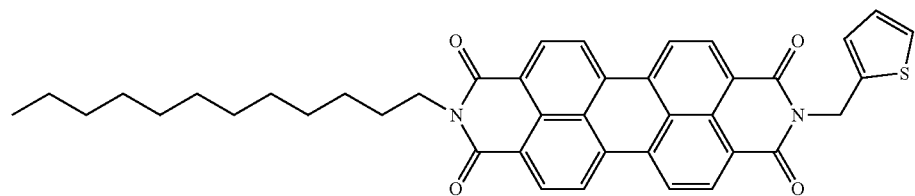
(II.70)
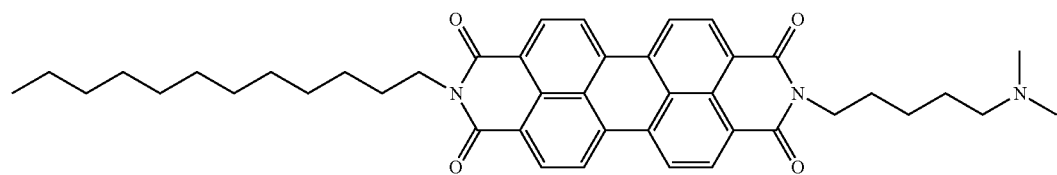
(II.71)
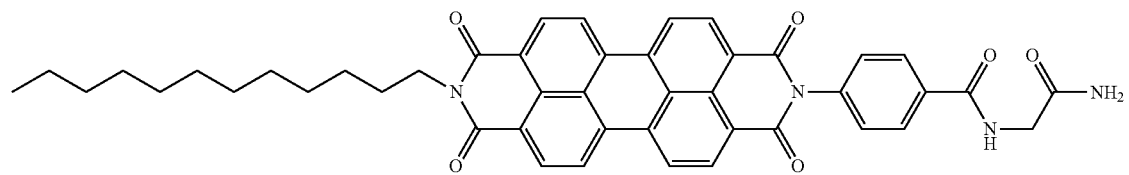
(II.72)

-continued
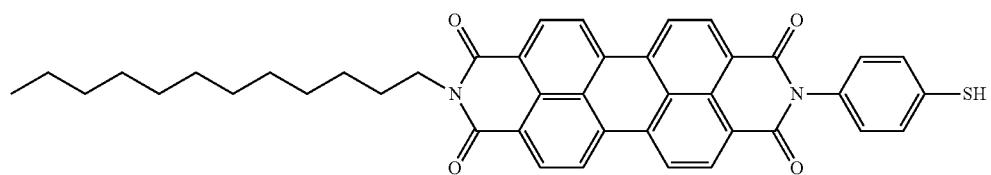
(II.73)
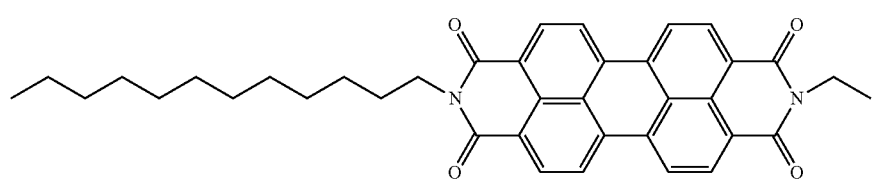
(II.74)
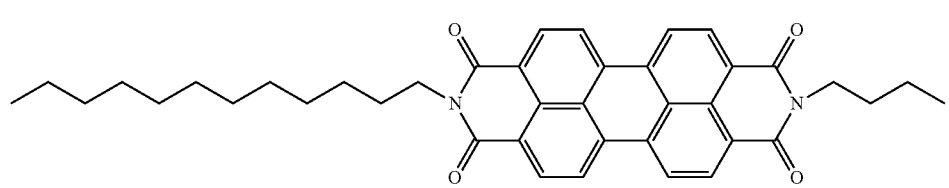
(II.75)
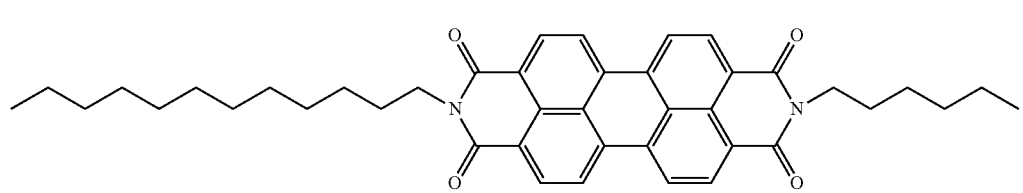
(II.76)
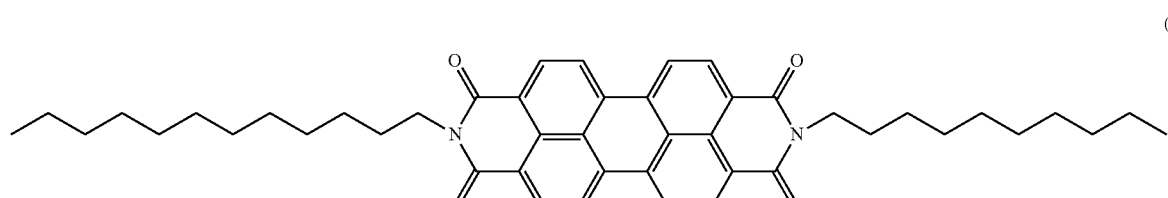
(II.77)
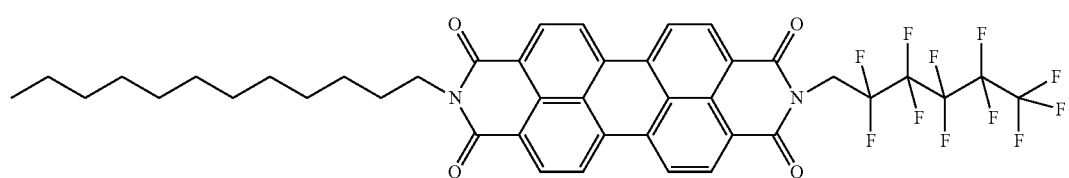
(II.78)
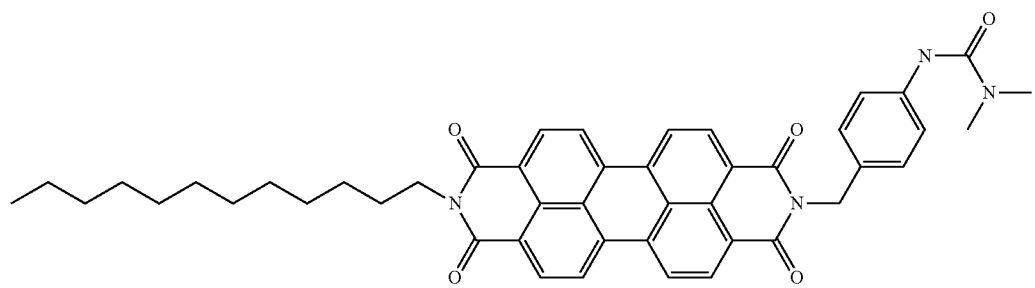
(II.79)
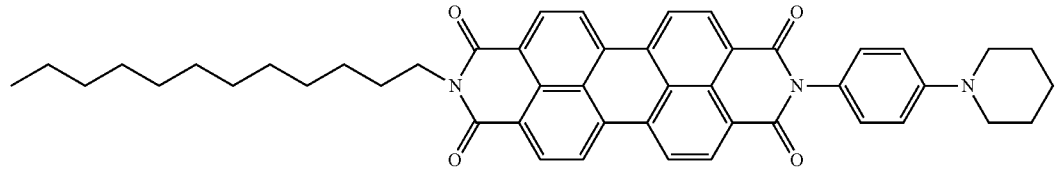
(II.80)

-continued

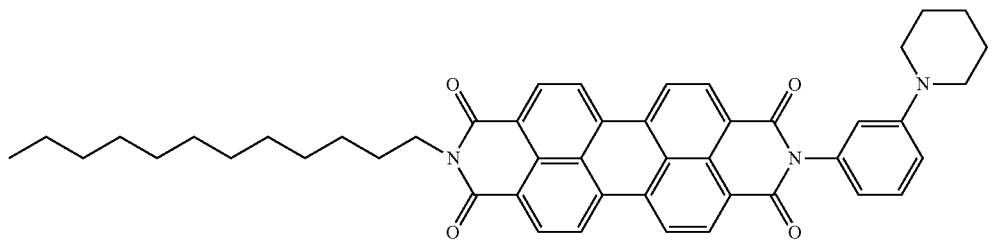

(II.81)

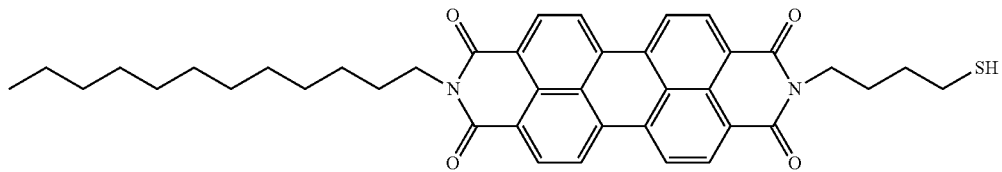

(II.82)

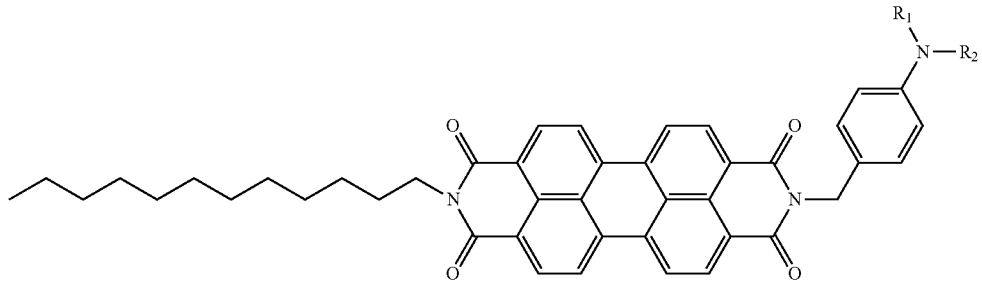

(II.83)

As will be appreciated by one skilled in the art, there are numerous chemical sensor compounds that can be prepared according to Formula II in addition to those presented in structures II.12-II.82. Such compounds can be prepared using known techniques. For example, 3,4,9,10-perylene tetracarboxylic acid bisanhydride can be used a starting material to form a diester-monoimide (e.g. such as those outlined above under Compound I). In one example, this can be accomplished using a known synthesis technique as outlined by Wang, R., et al. (2014), *"Facile synthesis and controllable bromination of asymmetrical intermediates of perylene monoanhydride/monoimide diester" Dyes and Pigments* 98(3): 450-458 which is incorporated herein by reference. The diester-monoimide can then be reacted to form a corresponding monoimide monoanhydride. Although other processes may be used, one example is outlined in Sengupta, S., et al. (2014), *"Synthesis of Regioisomerically Pure 1,7-Dibromoperylene-3,4,9,10-tetracarboxylic Acid Derivatives," The Journal of Organic Chemistry* 79(14): 6655-6662 which is also incorporated herein by reference. The resulting monoanhydride can then be reacted to form the desired bisimide via a condensation reaction with primary amines or ammonia.

Additionally, still other sensor compounds can be used in the method of detecting a non-explosive analyte, such as those having a structure according to Formula III:

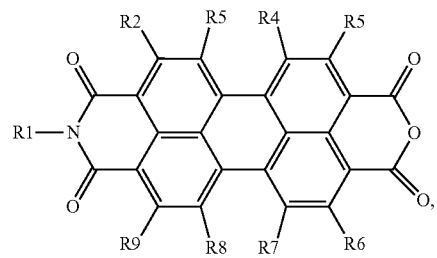

(III)

where R1 is chosen from $C_1$-$C_{20}$ substituted or unsubstituted linear aliphatic groups, branched aliphatic groups, cyclic groups (including heterocyclic groups), and aryl groups, and where R2-R9 are independently chosen from hydrogen, halides, carboxyl groups, hydroxyl groups, nitrile groups, $C_1$-$C_8$ alkyl groups, and combinations thereof.

Numerous R1 groups can be used with a sensor compound according to Formula III. For example, any of the R1 groups described or illustrated with respect to R1 of Formula II can also be used for R1 of Formula III. Non-limiting examples are illustrated in structures III.01 and III.02 below.

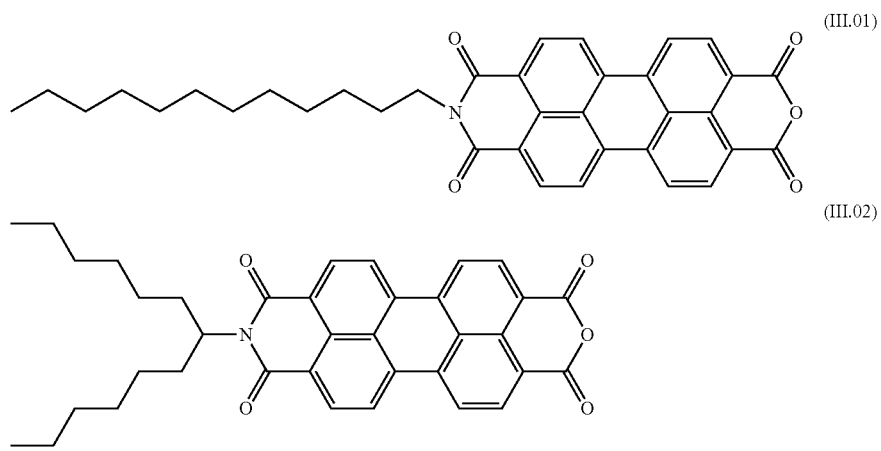

In some specific examples, R1 can be a $C_4$-$C_{16}$ substituted or unsubstituted linear or branched aliphatic group. In some examples, R1 can be a substituted or unsubstituted linear aliphatic group. In other examples, R1 can be a substituted or unsubstituted branched aliphatic group.

R2-R9 can typically be solubilizing groups, but in some cases can also be electron donating groups. Generally, any group can be used for R2-R9 that does not significantly diminish the selectivity and sensitivity of the sensor compound. In some examples, R2-R9 can include hydrogen, a halide, a carboxyl group, a hydroxyl group, a nitrile group, a $C_1$-$C_8$ alkyl group, the like, or a combination thereof. In some examples, at least one of R2-R9 is not hydrogen. In some examples, each of R2-R9 is hydrogen. In some examples, at least two of R2-R9 are independently a halide, a carboxyl group, a hydroxyl group, a nitrile group, a $C_1$-$C_8$ alkyl group, or a combination thereof.

As previously described, any one of the sensor compounds described herein can be used in the method of detecting a non-explosive analyte. Further, in some examples, a combination of different sensor compounds can be used to detect a non-explosive analyte. In some examples, the combination can include a plurality of compounds according to Formula I, a plurality of compounds according to Formula II, a plurality of compounds according to Formula III, or any combination of one or more compounds according to any of Formulas I, II, or III.

While any of the compounds described herein can be used in the method of detecting a non-explosive analyte, there are also described herein sensor compounds for detecting a target analyte, including both non-explosive and explosive analytes. The sensor compound for detecting a target analyte can include a compound having a structure according to Formula I:

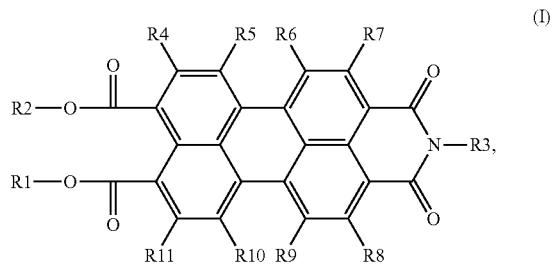

where R1, R2, and R3 are independently chosen from $C_1$-$C_{20}$ substituted or unsubstituted linear aliphatic groups, branched aliphatic groups, and aryl groups, and where R4-R11 are independently chosen from hydrogen, halides, carboxyl groups, hydroxyl groups, nitrile groups, $C_1$-$C_8$ alkyl groups, and combinations thereof.

In another example, the sensor compound for detecting a target analyte can include a compound having a structure according to Formula II:

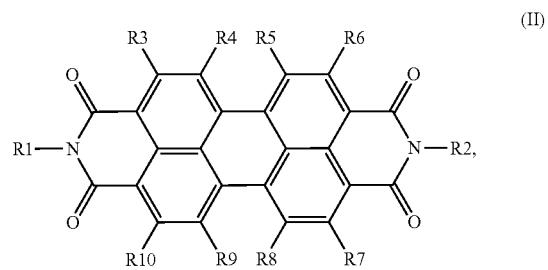

where R1 is chosen from $C_2$-$C_{20}$ substituted or unsubstituted linear aliphatic groups, branched aliphatic groups, and aryl groups, where R2 comprises a $C_2$-$C_{10}$ substituted or unsubstituted linear aliphatic group, an alkylbenzene group, a heterocycle, an aryl compound having an oxygen-containing side group, an aryl compound having a nitrogen-containing side group, an aryl compound having a sulfur-containing side group, or a combination thereof, and where R3-R10 are independently chosen from hydrogen, halides, carboxyl groups, hydroxyl groups, nitrile groups, $C_1$-$C_8$ alkyl groups, and combinations thereof.

It is noted that a combination of sensor compounds having a structure according to Formula I, Formula II, or both can be used to detect a target analyte. In some examples, the sensor compound can be a compound having a structure according to Formula I. Where this is the case, the compound can include the same features as the Formula I sensor compound described above with respect to the method of detecting a non-explosive composition. For example, each of structures I.01-I.10 are illustrative of non-limiting examples of the sensor compound for detecting a target analyte, including both non-explosive and explosive compounds.

In some examples, R1, R2, or both can be a $C_1$-$C_{12}$ substituted or unsubstituted linear aliphatic group, branched aliphatic group, or aryl group. In other examples, R1, R2, or both can be a $C_1$-$C_{12}$ substituted or unsubstituted linear or branched aliphatic group. In yet other examples, R1, R2, or both can be a $C_2$-$C_8$ or $C_2$-$C_6$ substituted or unsubstituted linear or branched aliphatic group.

While R3 can generally be a $C_1$-$C_{20}$ substituted or unsubstituted linear aliphatic group, branched aliphatic group, or aryl group, in some examples R3 can be a $C_4$-$C_{18}$ substituted or unsubstituted linear aliphatic group, branched aliphatic group, or aryl group. In yet other examples, R3 can be a $C_8$-$C_{16}$ substituted or unsubstituted linear or branched aliphatic group.

R4-R11 can include those groups described above with respect to the method of detecting a non-explosive analyte.

In some examples, the sensor compound can be a compound having a structure according to Formula II. In this case, R1 generally can be a $C_2$-$C_{20}$ substituted or unsubstituted linear aliphatic group, branched aliphatic group, aryl group, or a combination thereof. However, in other examples, R1 can be a $C_4$-$C_{16}$ substituted or unsubstituted linear aliphatic group, branched aliphatic group, aryl group, or combination thereof. In other examples, R1 can be a $C_2$-$C_{10}$ or $C_{14}$-$C_{20}$ substituted or unsubstituted linear or branched aliphatic group. In some examples, R1 can be a substituted or unsubstituted linear aliphatic group. In other examples, R1 can be a substituted or unsubstituted branched aliphatic group. In some examples, at least one hydrogen group of R1 can be substituted with a halide, such as fluorine, chlorine, bromine, etc. In one specific example, the halide can be fluorine. Non-limiting examples of suitable R1 groups are illustrated in structures II.01-II.04 above.

R2 can include a wide variety of functional groups, such as a $C_2$-$C_{10}$ substituted or unsubstituted linear aliphatic group, an alkylbenzene group, a heterocycle, an aryl compound having an oxygen-containing side group, an aryl compound having a nitrogen-containing side group, an aryl compound having a sulfur-containing side group, or a combination thereof, for example.

In some examples, R2 can include a $C_2$-$C_{10}$ substituted or unsubstituted linear or branched aliphatic group. Where this is the case, non-limiting examples of suitable R2 groups can be illustrated in the following structures:

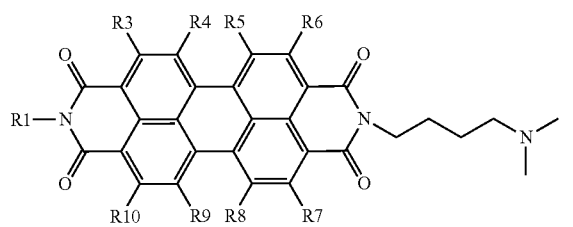

(II.07)

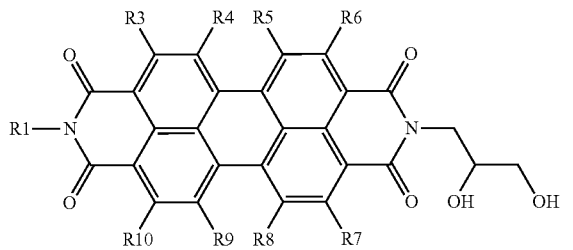

(II.09)

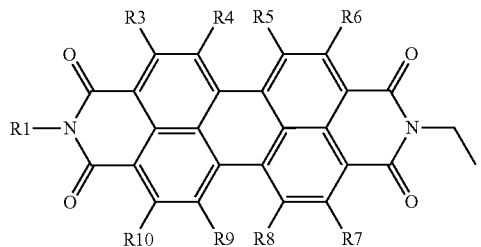

(II.10)

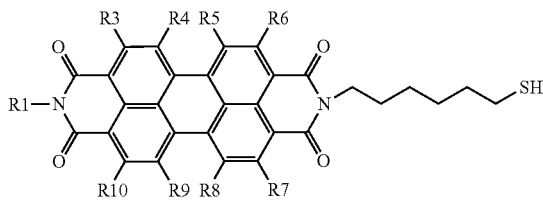

(II.11)

As will be appreciated by one skilled in the art, numerous other $C_2$-$C_{10}$ substituted or unsubstituted linear or branched aliphatic R2 groups can also be employed in Formula II in addition to those illustrated in structures II.07 and II.09-II.11. For example, in some cases, one or more hydrogen groups can be substituted for a halide. In some examples, the halide can be fluorine. In some examples, where the $C_2$-$C_{10}$ substituted or unsubstituted linear or branched aliphatic R2 group includes a nitrogen group, the nitrogen group is not associated with a primary amine group. In some examples, where the $C_2$-$C_{10}$ substituted or unsubstituted linear or branched aliphatic R2 group includes an oxygen group, the oxygen group is not associated with an ether group.

In other examples, R2 can include an alkylbenzene group. Alkylbenzene groups can include one or more alkyl groups attached to a benzene ring, such as, for example:

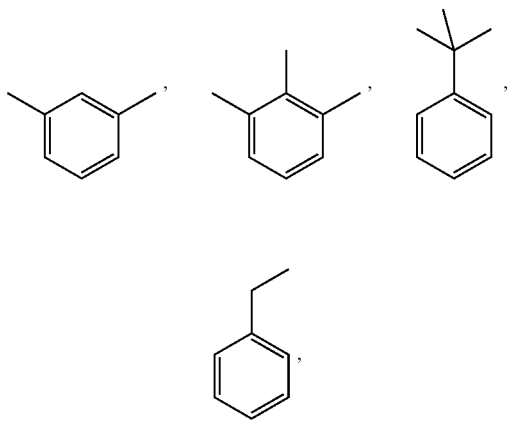

or combinations thereof.

In yet other examples, R2 can include a heterocycle. These heterocycles can include a variety of cyclical compounds where a carbon atom has been substituted with a non-carbon atom. Non-limiting examples can include:

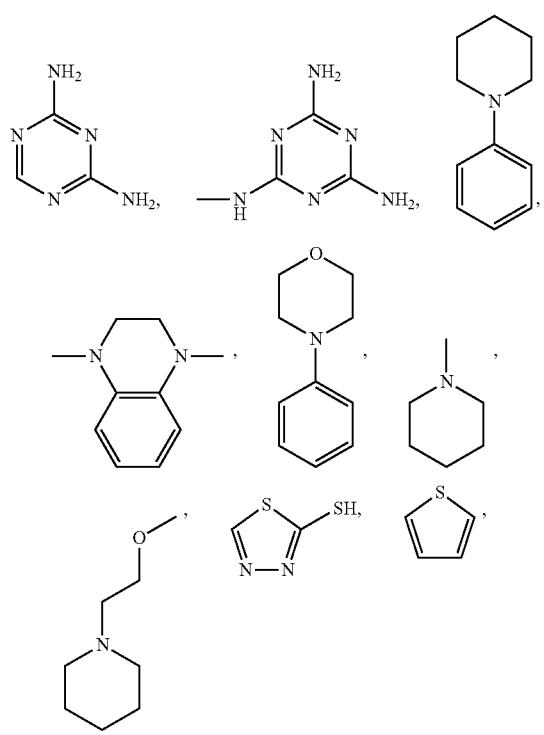

or combinations thereof. In some examples, where R2 includes a heterocycle, R2 is not pyridine.

In other examples, R2 can include an aryl compound having an oxygen-containing side group, such as, for example:

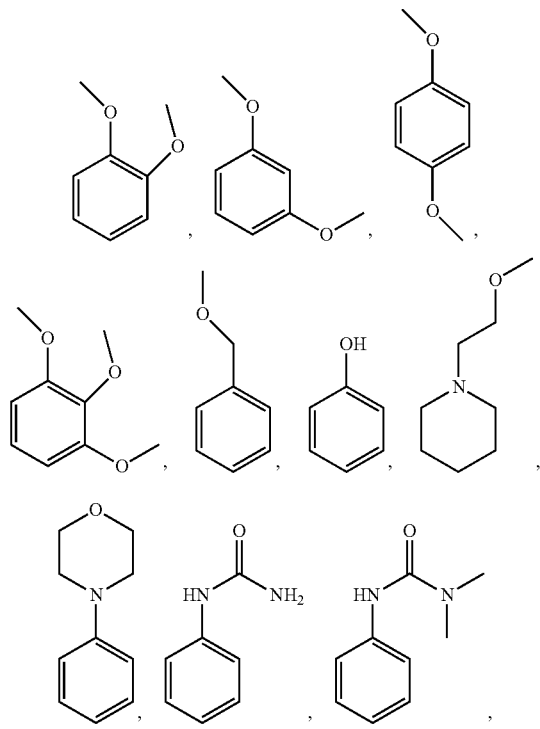

or combinations thereof. In some examples, where R2 includes an aryl compound having an oxygen-containing side group, R2 is not methoxy benzene (i.e. mono-methoxy benzene). In some examples, where R2 is not methoxy benzene, R2 is not para-methoxy benzene. In some examples, where R2 is not methoxy benzene, R2 is not meta-methoxy benzene. In some examples, where R2 is not methoxy benzene, R2 is not ortho-methoxy benzene.

In some other examples, R2 can include an aryl compound having a nitrogen-containing side group, such as, for example:

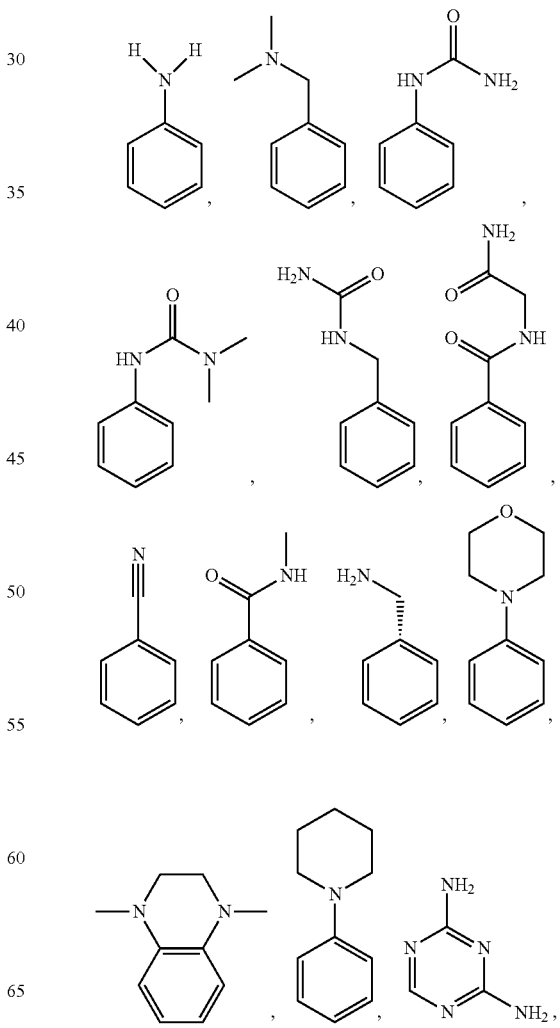

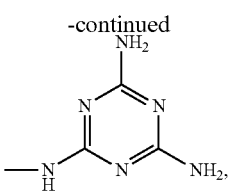

or combinations thereof. In some examples, where R2 includes an aryl compound having a nitrogen-containing side group, R2 is not or does not include dimethylaniline.

In additional examples, R2 can include an aryl compound having a sulfur-containing side group, such as, for example:

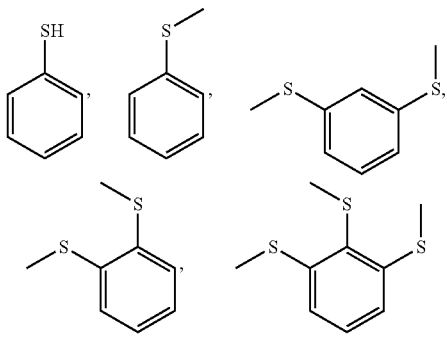

or combinations thereof.

As will be apparent to one skilled in the art, various other R2 groups can also be used in the sensor compound having a structure according to Formula II. Generally, non-limiting examples of suitable R1 and R2 groups are illustrated in structures II.14-II.28 and II.31-II.82 above.

With respect to R3-R10, these groups can typically be solubilizing groups, but in some cases can also be electron donating groups. Generally, any group can be used for R3-R10 that does not significantly diminish the selectivity and sensitivity of the sensor compound. In some examples, R3-R10 can include hydrogen, a halide, a carboxyl group, a hydroxyl group, a nitrile group, a $C_1$-$C_8$ alkyl group, the like, or a combination thereof. In some examples, at least one of R3-R10 is not hydrogen. In some examples, each of R3-R10 is hydrogen. In some examples, at least two of R3-R10 is a halide, a carboxyl group, a hydroxyl group, a nitrile group, a $C_1$-$C_8$ alkyl group, or a combination thereof.

In another aspect of the current disclosure, the sensor compounds for detecting a target analyte, including both explosive and non-explosive analytes, can be included in a sensor device. The sensor device for detecting a target analyte can include a substrate and a nanostructure sensor material positioned on the substrate in a plurality of detection zones. The nanostructure sensor material can include or be formed of a sensor compound as described herein. The nanostructure sensor material can take the form of nanofibers, nanobelts, the like, and combinations thereof. In some examples, the nanostructure sensor material can be deposited or otherwise positioned on the substrate so as to form a porous thin film at each of the plurality of detection zones. In some examples, the substrate can include a plurality of holes allowing fluid to flow through the substrate. Thus, when the substrate is exposed to a fluid, such as a gas or liquid, that includes the target analyte, the fluid can be directed to pass through the porous film and plurality of holes in the substrate. In some examples, this can be facilitated by employing a housing having an inlet and an outlet and positioning the substrate within the housing between the inlet and the outlet. The housing can act to direct the fluid through the holes in the substrate to increase the area of contact between the fluid and the porous film formed of the sensor compound nanostructures.

Depending on the mode of detection of the independent nanostructures, the device can include other features to facilitate sensing of the target analyte. For example, in some cases, the substrate can include independently addressable electrode pairs at one or more of the plurality of detection zones. This can facilitate detection of a change in conductivity of the nanostructure via interfacial charge transfer, for example. In other examples, the sensor device can include a light source to induce photocurrent across the nanostructure or to produce a fluorescent emission of the nanostructure. This can facilitate detection of a change in photocurrent across the nanostructure or detection of fluorescence quenching of the nanostructure. The sensor device can also include a fluorescence detector or any other suitable detector to facilitate displaying a change in the sensor compound nanostructure upon exposure to a target analyte.

With respect to the sensor compounds that can be used with the sensor device, generally any of the sensor compounds described above for detection of a target analyte can be used. For example, the sensor compound can be a compound according to Formula I. In other examples, the sensor compound can be a compound according to Formula II.

In other examples, at least two of the plurality of detection zones can include different sensor compounds. Where this is the case, in some examples, one or more of the different sensor compounds can be a sensor compound according to Formula I. In other examples, one or more of the different sensor compounds can be a sensor compound according to Formula II. In yet other examples, one or more of the different sensor compounds can be a sensor compound having a structure according to Formula III:

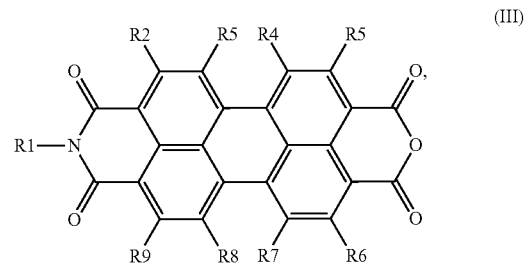

where R1 is chosen from $C_1$-$C_{20}$ substituted or unsubstituted linear aliphatic groups, branched aliphatic groups, cyclic groups (including heterocyclic groups), and aryl groups, and where R2-R9 are independently chosen from hydrogen, halides, carboxyl groups, hydroxyl groups, nitrile groups, $C_1$-$C_8$ alkyl groups, and combinations thereof. However, where one or more of the detection zones includes a sensor compound having a structure according to Formula III, at least one of the plurality of detection zones includes a sensor compound having a structure according to Formula I or Formula II.

The chemical sensors described herein can open broad applications in detection of numerous analytes, such as peroxide based explosives, chemical warfare agents, narcotic drugs and chemicals used to manufacture illicit drugs, and improvised explosive devices, for example.

EXAMPLES

Example 1—Sensor Compound Comparison with PBTTF/TCNQ Sensor Material

A number of sensor compounds were prepared and deposited on a substrate as a thin film. The sensor compounds were exposed to various target analytes to determine the limit of detection, direction of current response, and rate of recovery after detection of the target analyte by the sensor compound. As a comparison, a standard p-phenylenebistetrathiafulvalene (PBTTF)-tetracyanoquinodimethane (TCNQ) sensor material was also evaluated. Some representative results of these studies are presented in Tables 1-6 below.

TABLE 1

Evaluation of sensor compound having structure II.12.

| | Structure II.12 | |
|---|---|---|
| Analyte | Limit of Detection | Response/Recovery |
| Ammonia | 2 ppm | Positive/Medium |
| Methyl Amine | 400 ppb | Positive/Medium |
| Crystal methamphetamine Analog | 1.5 ppb | Positive/Medium |

TABLE 2

Evaluation of sensor compound having structure II.13.

| | Structure II.13 | |
|---|---|---|
| Analyte | Limit of Detection | Response/Recovery |
| Ammonia | 2 ppb | Positive/Medium |
| Methyl Amine | 24 ppb | Positive/Rapid |
| Crystal methamphetamine Analog | 3 ppb | Positive/Rapid |
| Tri-t-butyl phosphine | 140 ppb | Positive/Rapid |
| Hexane | ppt | Negative/Rapid |

TABLE 3

Evaluation of sensor compound having structure III.02.

| | Structure III.02 | |
|---|---|---|
| Analyte | Limit of Detection | Response/Recovery |
| Ammonia | 100 ppb | Positive/Slow |
| Methyl Amine | 100 ppb | Positive/Slow |
| Crystal methamphetamine Analog | 50 ppb | Positive/Slow |

TABLE 3-continued

Evaluation of sensor compound having structure III.02.

| | Structure III.02 | |
|---|---|---|
| Analyte | Limit of Detection | Response/Recovery |
| HCl | 100 ppb | Negative/Slow |
| Hexane | 100 ppm | Negative/Rapid |

TABLE 4

Evaluation of sensor compound having structure II.14.

| | Structure II.14 | |
|---|---|---|
| Analyte | Limit of Detection | Response/Recovery |
| Ammonia | 200 ppb | Positive/Rapid |
| Methyl Amine | 45 ppb | Positive/Medium |
| Tri-t-butyl phosphine | 330 ppb | Positive/Slow |

TABLE 5

Evaluation of sensor compound having structure II.42.

| | Structure II.42 | |
|---|---|---|
| Analyte | Limit of Detection | Response/Recovery |
| Ammonia | 3 ppm | Positive/Slow |
| HCl | 2 ppm | Negative/Rapid |

TABLE 6

Evaluation of PBTTF/TCNQ sensor compound.

| | PBTTF/TCNQ | |
|---|---|---|
| Analyte | Limit of Detection | Response/Recovery |
| Ammonia | 150 ppb | Positive/Medium |
| Crystal methamphetamine analog | 5 ppb | Positive/Slow |
| HCl | 100 ppb | Negative/Slow |

Example 2—Evaluation of a Select Sensor Compounds

A number of sensor compounds were prepared and deposited on a substrate as a thin film. SEM micrographs were obtained for the sensor compounds. Further, the sensor materials were exposed to a variety of target analytes to determine current response as a function of time.

Figure 1B:
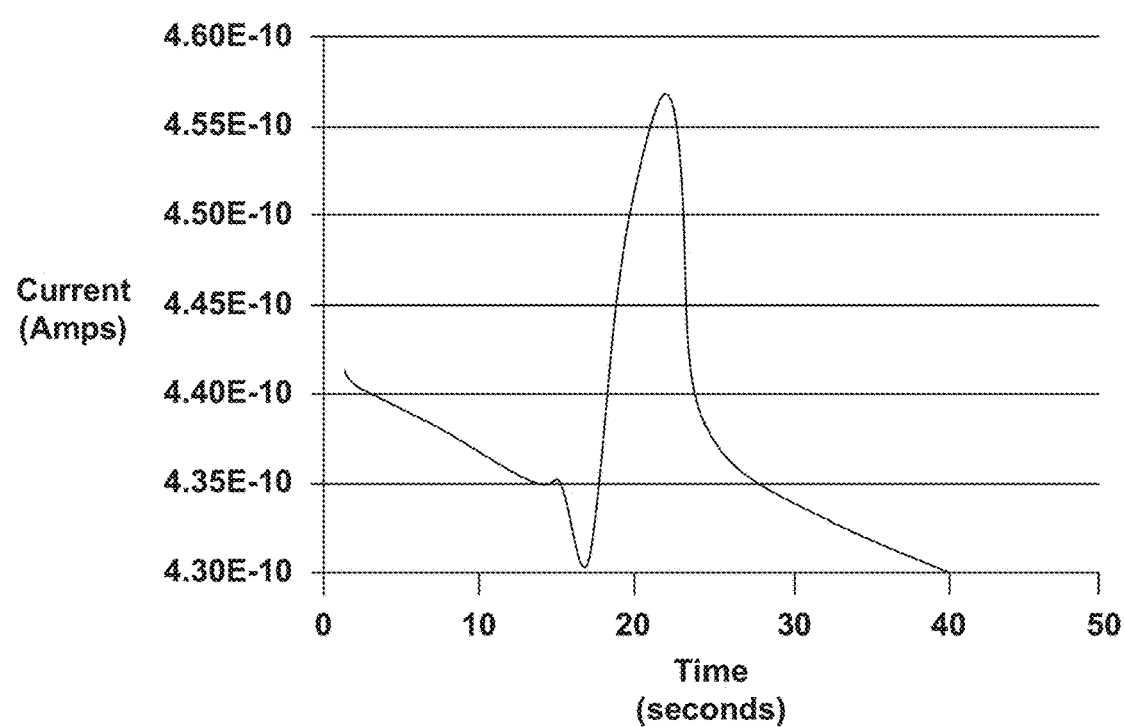
FIG. 1B is a graph illustrating change in current as a function of time for the sensor compound of FIG. 1A upon exposure to hydrogen peroxide.
Figure 1C:
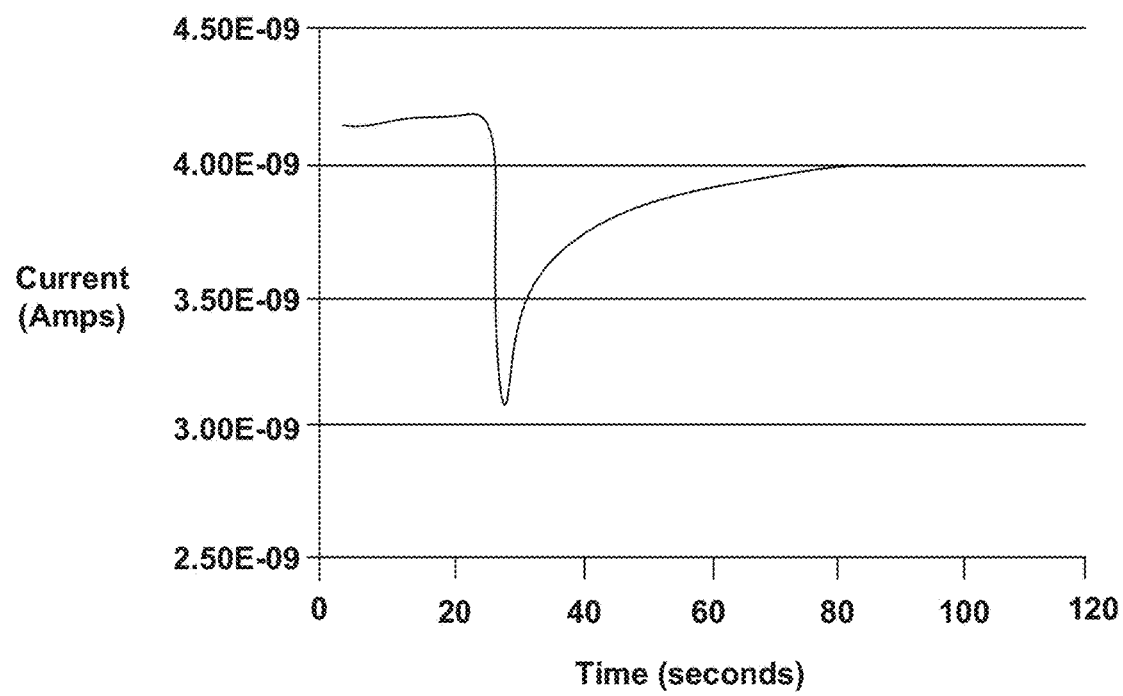
FIG. 1C is a graph illustrating change in current as a function of time for the sensor compound of FIG. 1A upon exposure to hexane.
Figure 1D:
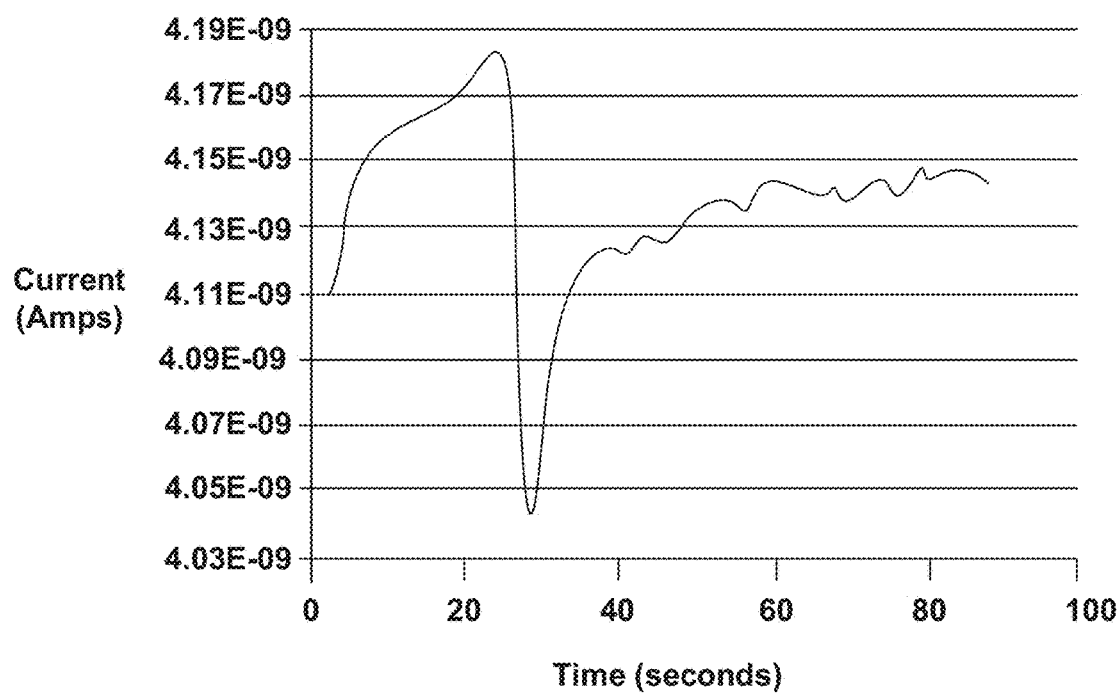
FIG. 1D is a graph illustrating change in current as a function of time for the sensor compound of FIG. 1A upon exposure to hydrochloric acid.
Figure 1E:
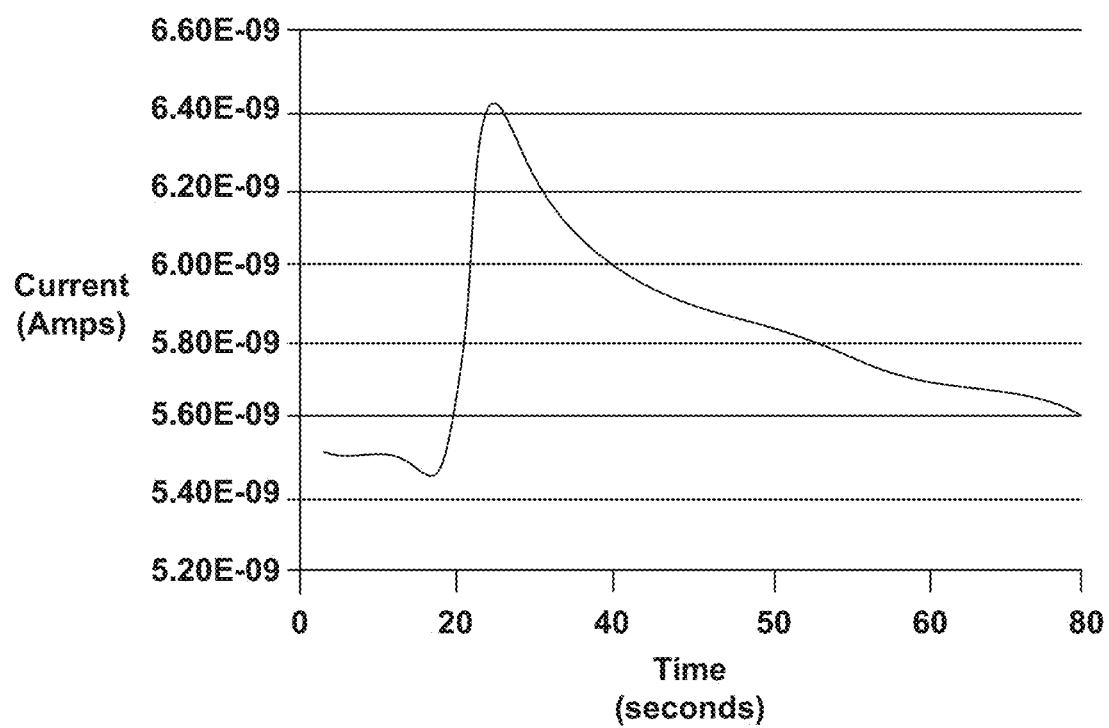
FIG. 1E is a graph illustrating change in current as a function of time for the sensor compound of FIG. 1A upon exposure to an amine-containing drug.

FIG. 1A illustrates an SEM image of a sensor compound having structure II.12. The structure II.12 chemical sensor was exposed to various target analytes to determine the electrical response properties of the chemical sensor upon exposure to these analytes. FIG. 1B depicts an example of the response properties of one example of this material upon exposure to hydrogen peroxide. FIG. 1C depicts an example of the response properties of one example of this material upon exposure to hexane. FIG. 1D depicts an example of the response properties of one example of this material upon exposure to hydrochloric acid. FIG. 1E depicts an example of the response properties of one example of this material upon exposure to an amine-containing drug.

Figure 2A:
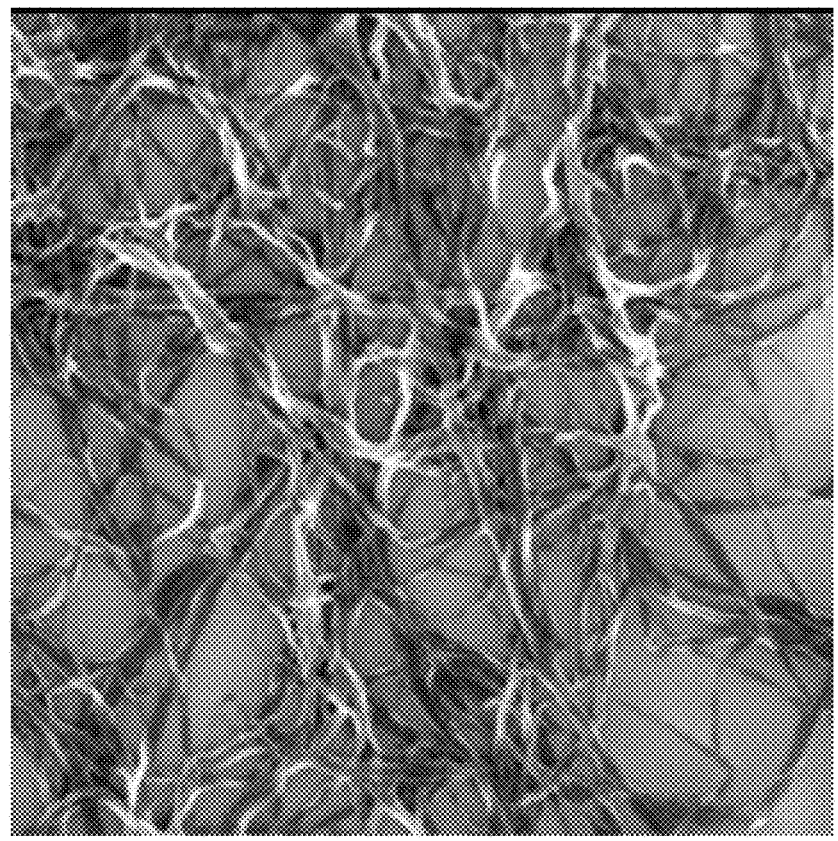
FIG. 2A illustrates an SEM image of a sensor compound, in accordance with some examples of the current disclosure.
Figure 2B:
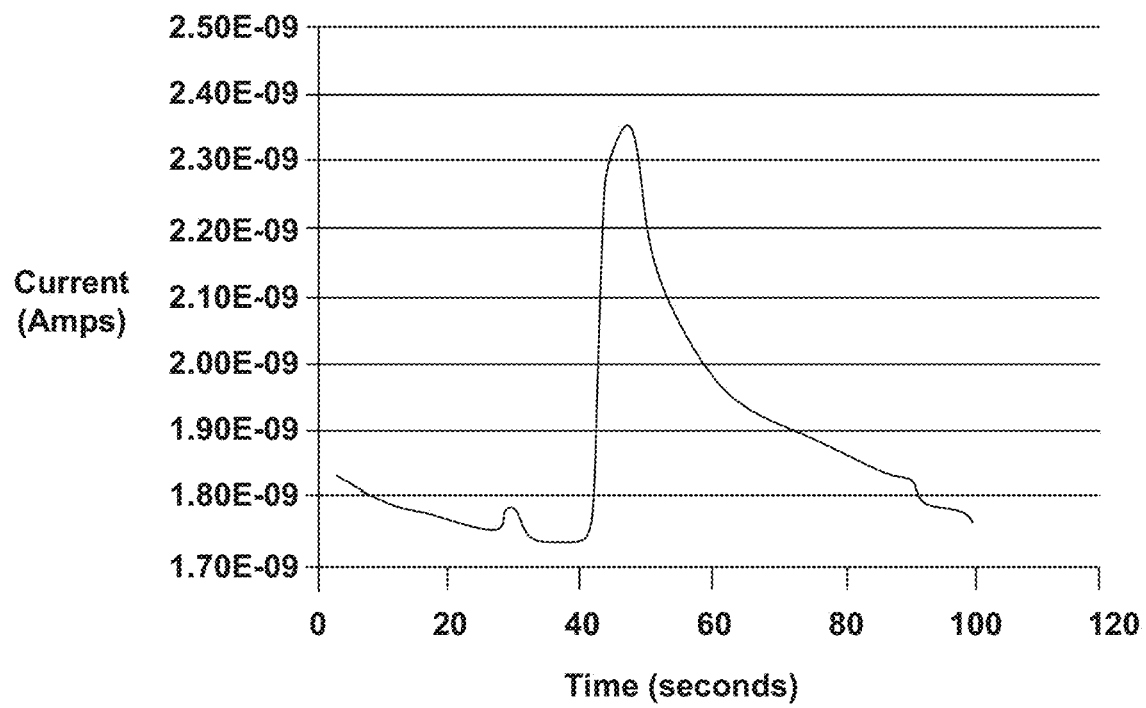
FIG. 2B is a graph illustrating change in current as a function of time for the sensor compound of FIG. 2A upon exposure to hydrogen peroxide.
Figure 2C:
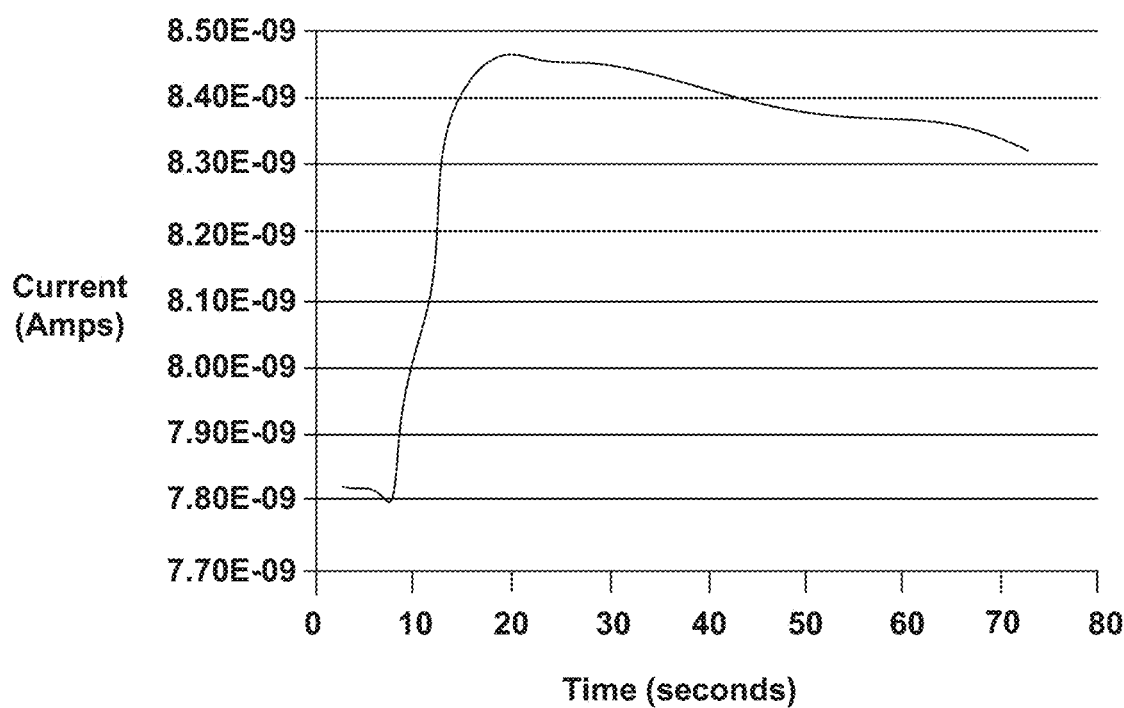
FIG. 2C is a graph illustrating change in current as a function of time for the sensor compound of FIG. 2A upon exposure to tert-butyl phosphine.

FIG. 2A illustrates an SEM image of a sensor compound having a structure II.18. The structure II.18 chemical sensor was exposed to various target analytes to determine the electrical response properties of the chemical sensor upon exposure to these analytes. FIG. 2B depicts an example of the response properties of one example of this material upon exposure to hydrogen peroxide. FIG. 2C depicts an example of the response properties of one example of this material upon exposure to tert-butyl phosphine.

Figure 3A:
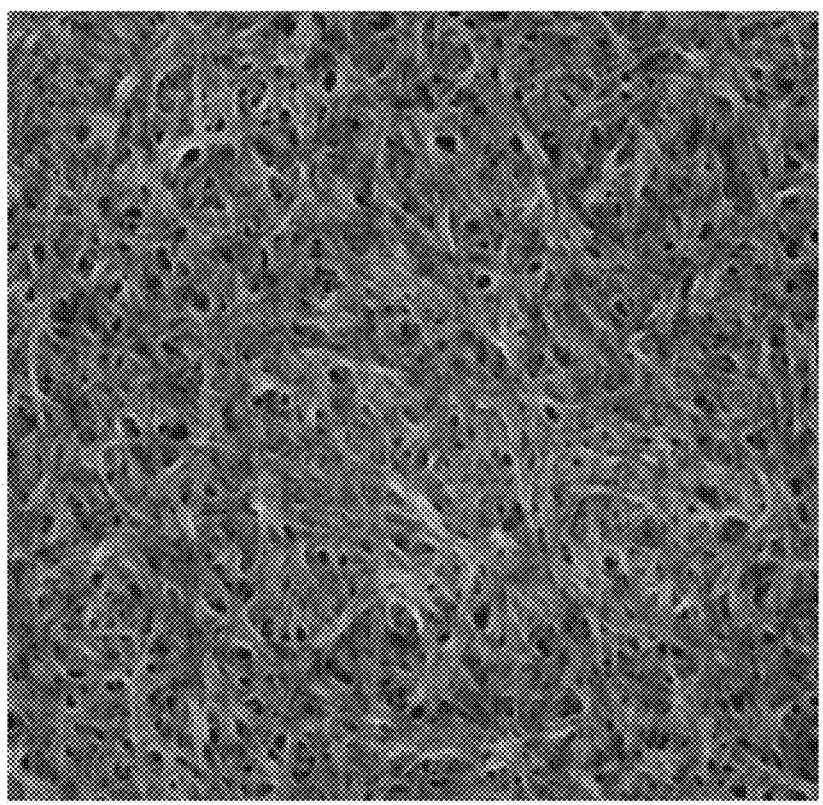
FIG. 3A illustrates an SEM image of a sensor compound, in accordance with some examples of the current disclosure.
Figure 3B:
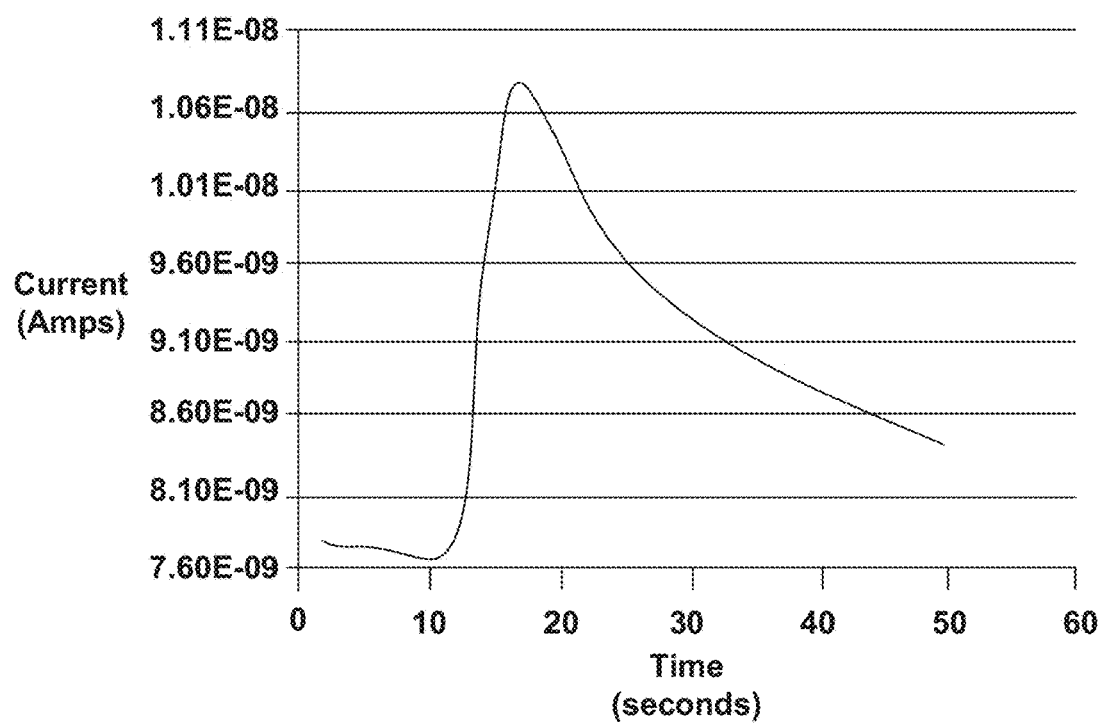
FIG. 3B is a graph illustrating change in current as a function of time for the sensor compound of FIG. 3A upon exposure to hydrogen peroxide.

FIG. 3A illustrates an SEM image of a sensor compound having a structure II.13. The structure II.13 chemical sensor was exposed to hydrogen peroxide to determine the electrical response properties of the chemical sensor upon exposure to this anylayte. FIG. 3B depicts an example of the response properties of one examples of this material upon exposure to hydrogen peroxide.

Figure 4A:
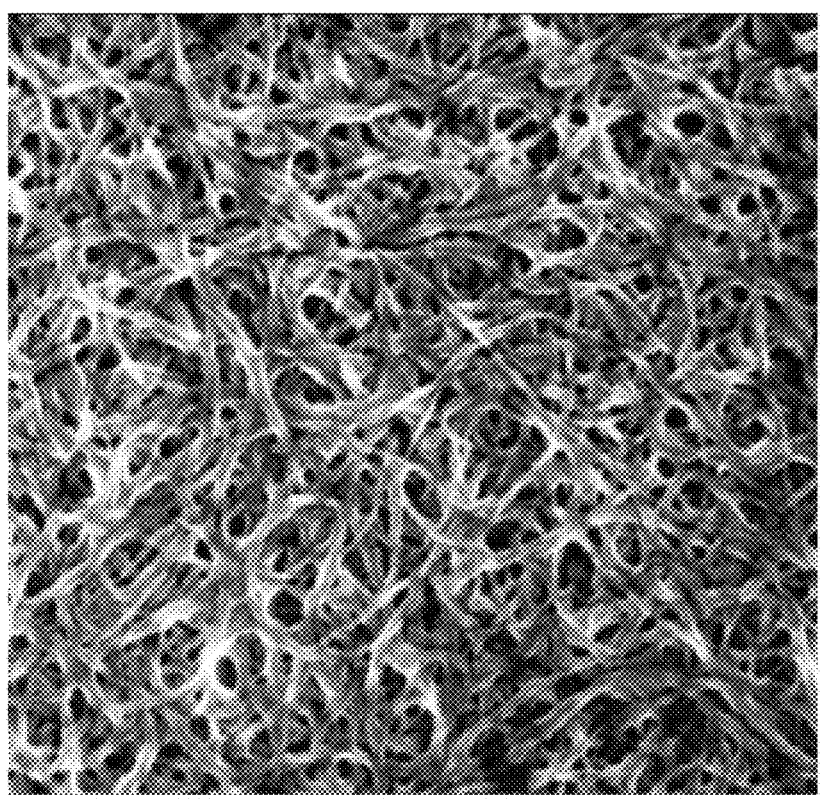
FIG. 4A illustrates an SEM image of a sensor compound, in accordance with some examples of the current disclosure.
Figure 4B:
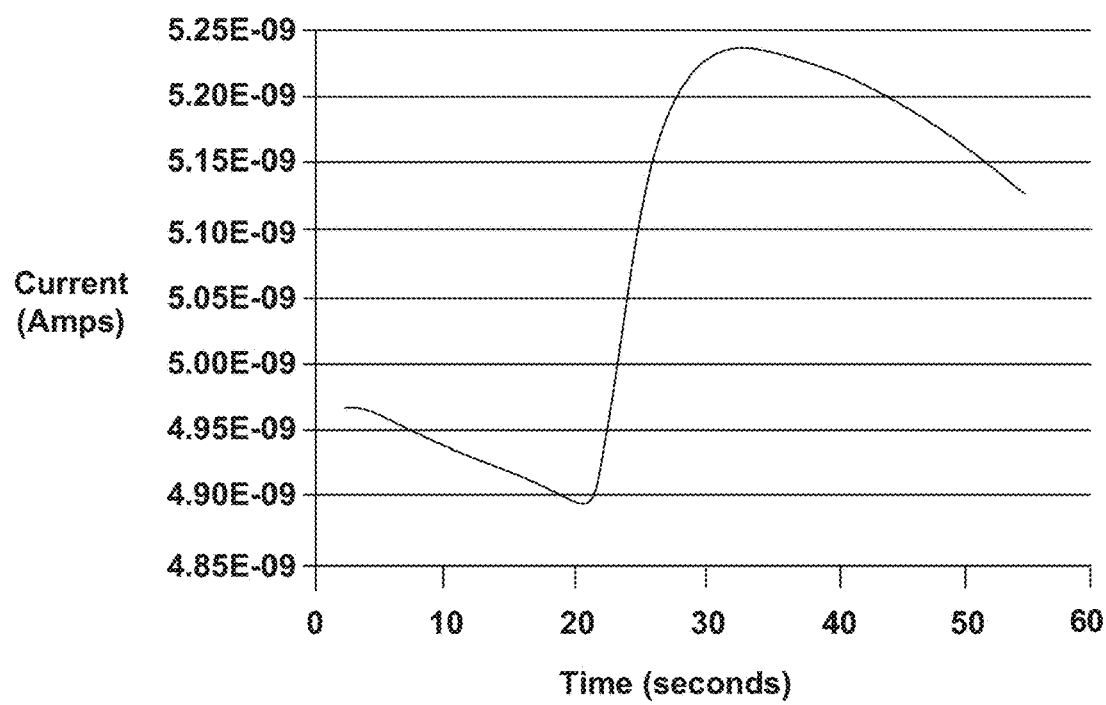
FIG. 4B is a graph illustrating change in current as a function of time for the sensor compound of FIG. 4A upon exposure to hydrogen peroxide.

FIG. 4A illustrates an SEM image of a sensor compound having a structure II.14. The structure II.14 chemical sensor was exposed to hydrogen peroxide to determine the electrical response properties of the chemical sensor upon exposure to this anylayte. FIG. 4B depicts an example of the response properties of one examples of this material upon exposure to hydrogen peroxide.

Figure 5A:
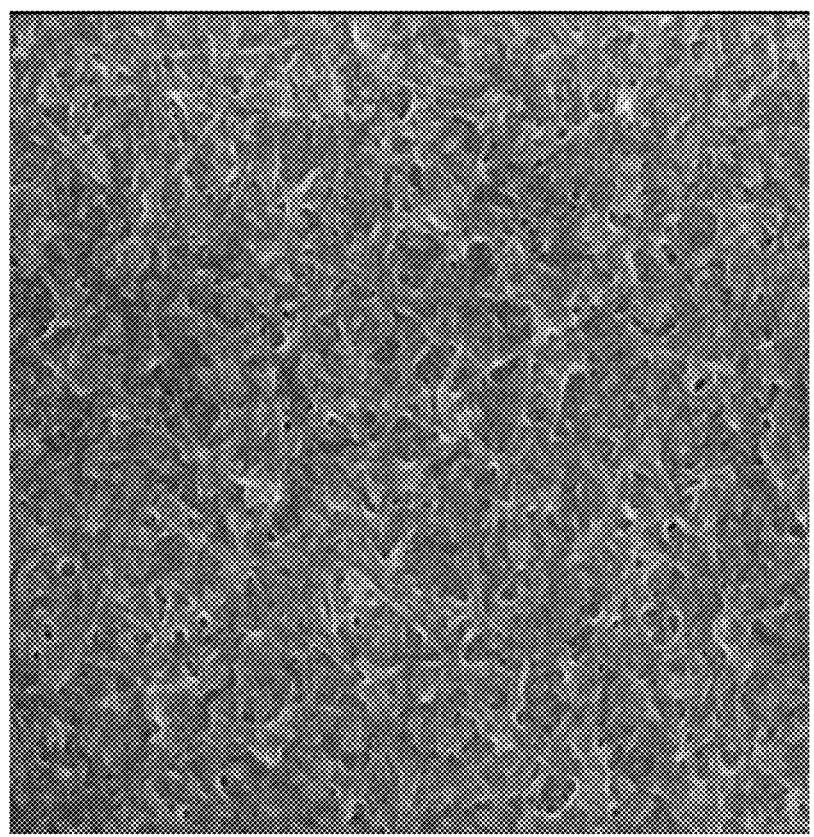
FIG. 5A illustrates an SEM image of a sensor compound, in accordance with some examples of the current disclosure.
Figure 5B:
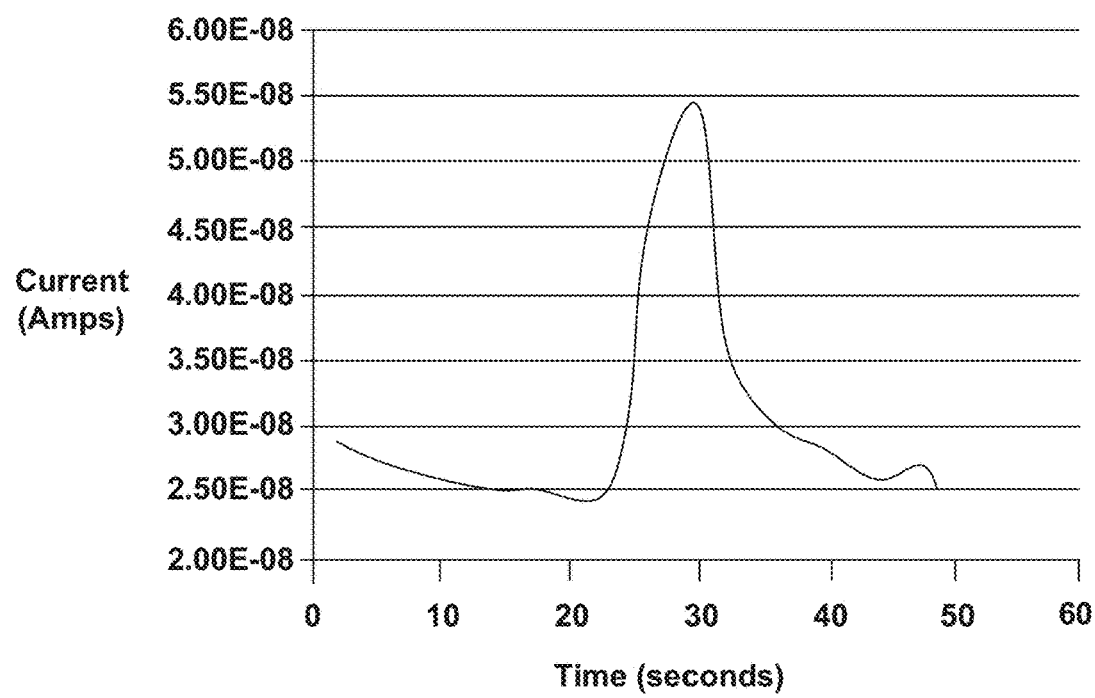
FIG. 5B is a graph illustrating change in current as a function of time for the sensor compound of FIG. 5A upon exposure to hydrogen peroxide.

FIG. 5A illustrates an SEM image of a sensor compound having a structure II.15. The structure II.15 chemical sensor was exposed to hydrogen peroxide to determine the electrical response properties of the chemical sensor upon exposure to this anylayte. FIG. 5B depicts an example of the response properties of one examples of this material upon exposure to hydrogen peroxide.

Figure 6A:
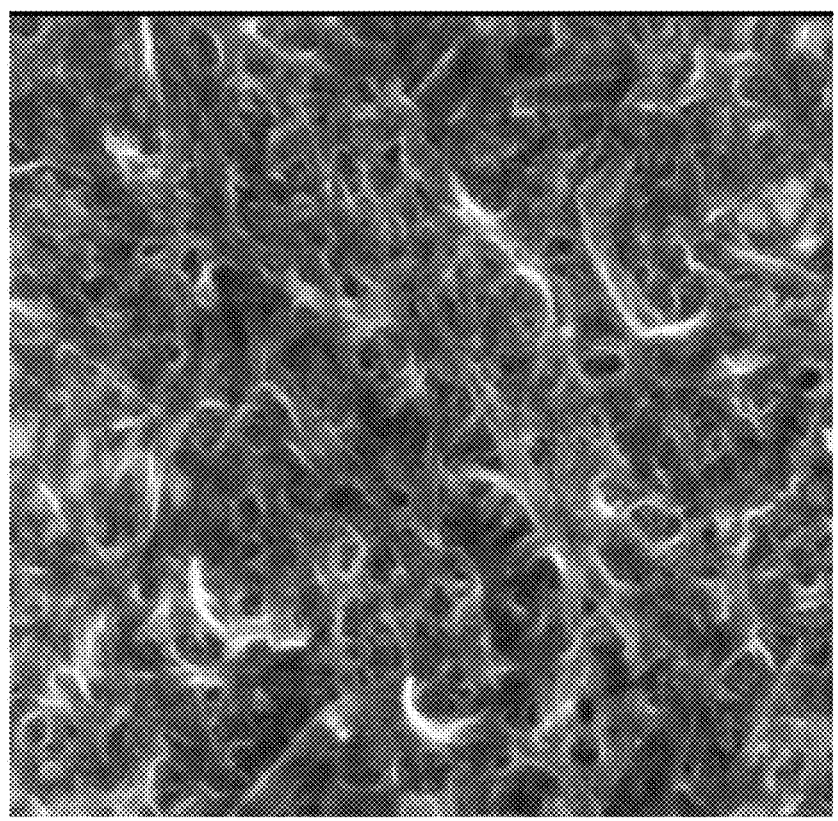
FIG. 6A illustrates an SEM image of a sensor compound, in accordance with some examples of the current disclosure.
Figure 6B:
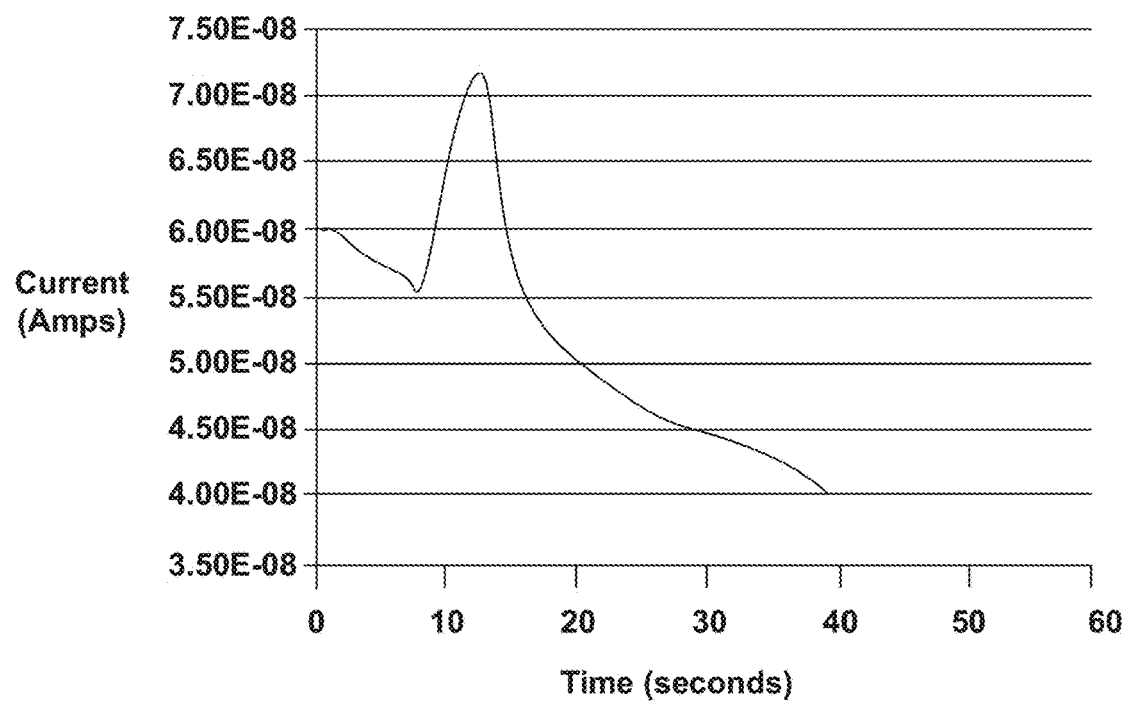
FIG. 6B is a graph illustrating change in current as a function of time for the sensor compound of FIG. 6A upon exposure to hydrogen peroxide.

FIG. 6A illustrates an SEM image of a sensor compound having a structure II.16. The structure II.16 chemical sensor was exposed to hydrogen peroxide to determine the electrical response properties of the chemical sensor upon exposure to this anylayte. FIG. 6B depicts an example of the response properties of one examples of this material upon exposure to hydrogen peroxide.

Figure 7A:
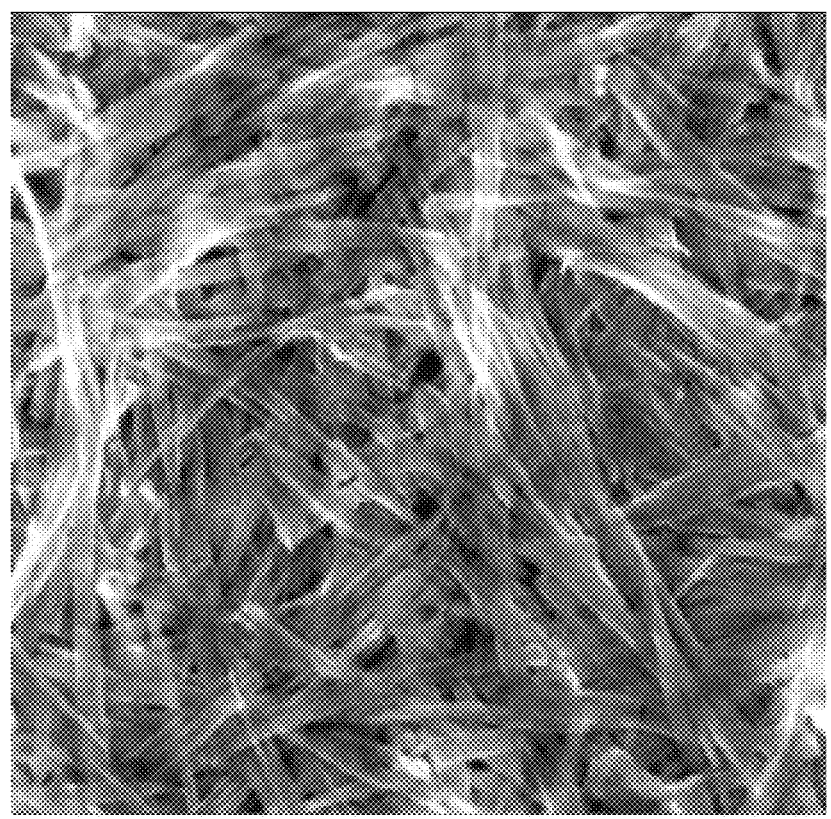
FIG. 7A illustrates an SEM image of a sensor compound, in accordance with some examples of the current disclosure.
Figure 7B:
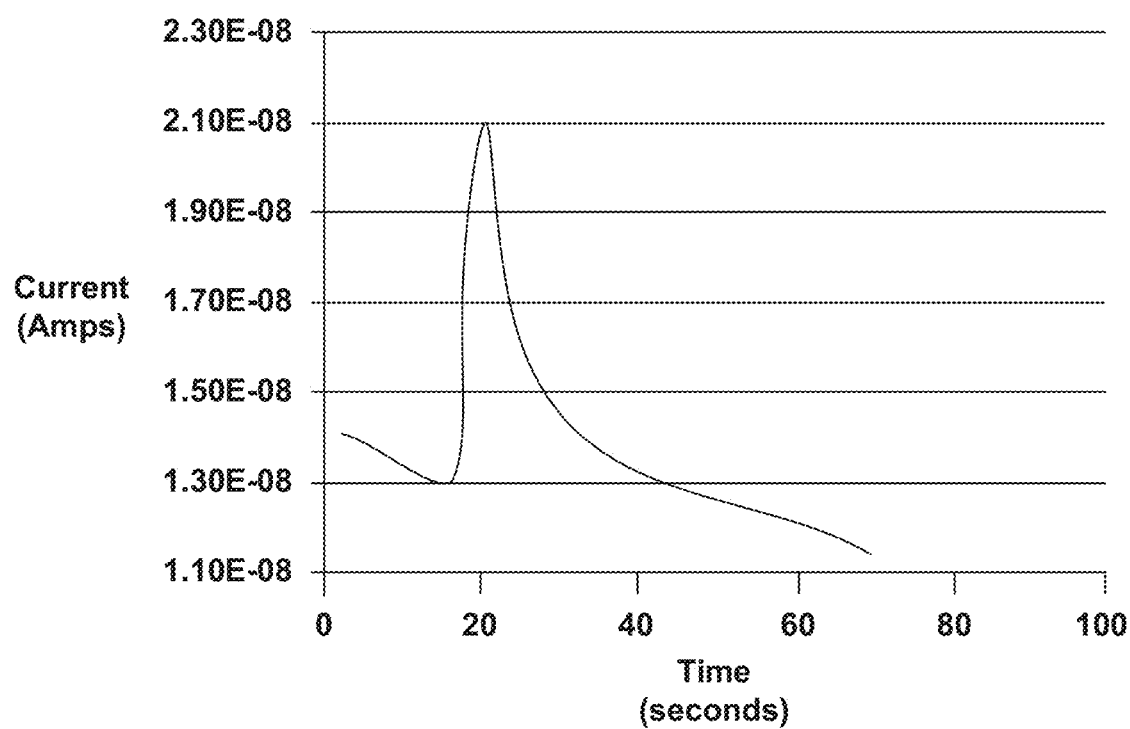
FIG. 7B is a graph illustrating change in current as a function of time for the sensor compound of FIG. 7A upon exposure to hydrogen peroxide.

FIG. 7A illustrates an SEM image of a sensor compound having a structure II.17. The structure II.17 chemical sensor was exposed to hydrogen peroxide to determine the electrical response properties of the chemical sensor upon exposure to this anylayte. FIG. 7B depicts an example of the response properties of one examples of this material upon exposure to hydrogen peroxide.

Figure 8A:
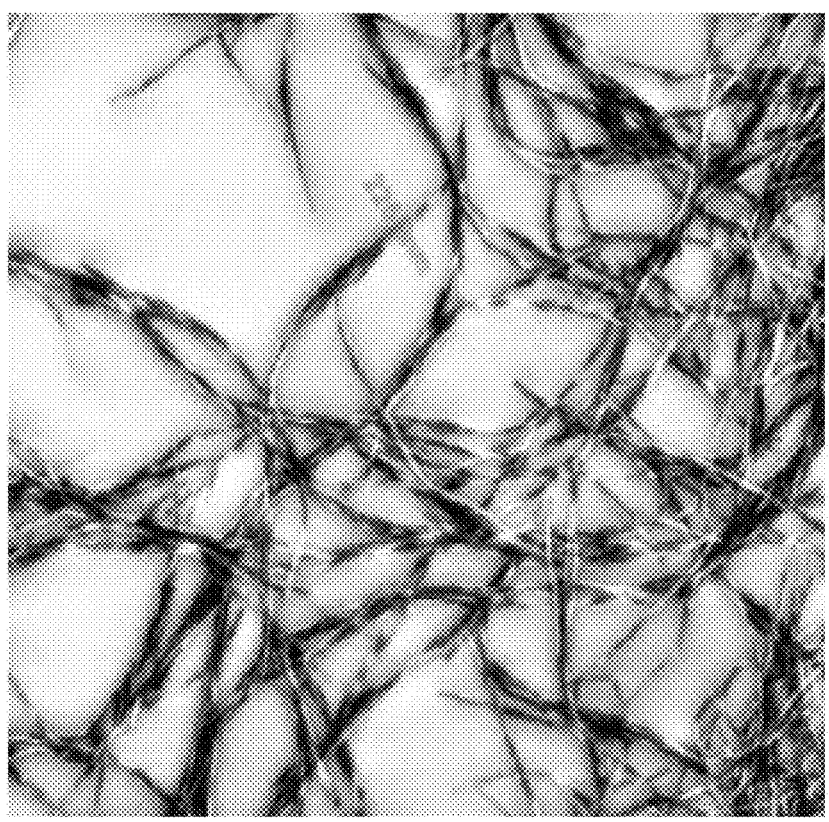
FIG. 8A illustrates an SEM image of a sensor compound, in accordance with some examples of the current disclosure.
Figure 8B:
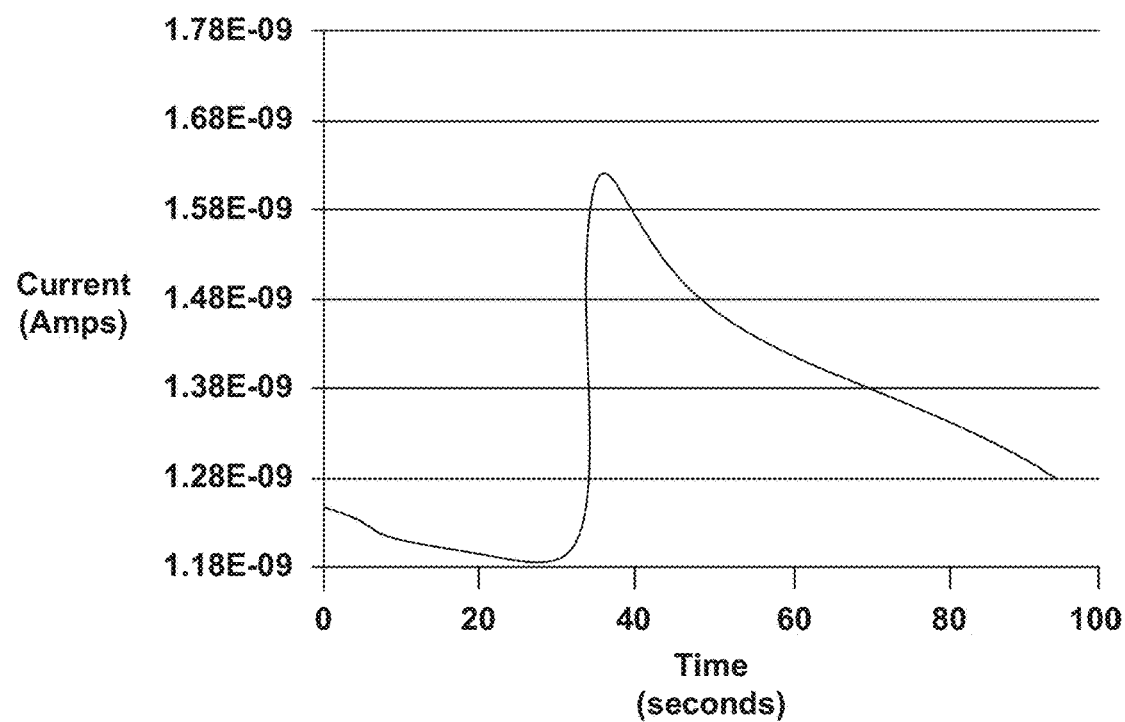
FIG. 8B is a graph illustrating change in current as a function of time for the sensor compound of FIG. 8A upon exposure to hydrogen peroxide.

FIG. 8A illustrates an SEM image of a sensor compound having a structure II.19. The structure II.19 chemical sensor was exposed to hydrogen peroxide to determine the electrical response properties of the chemical sensor upon exposure to this anylayte. FIG. 8B depicts an example of the response properties of one examples of this material upon exposure to hydrogen peroxide.

Figure 9A:
FIG. 9A illustrates an SEM image of a sensor compound, in accordance with some examples of the current disclosure.
Figure 9B:
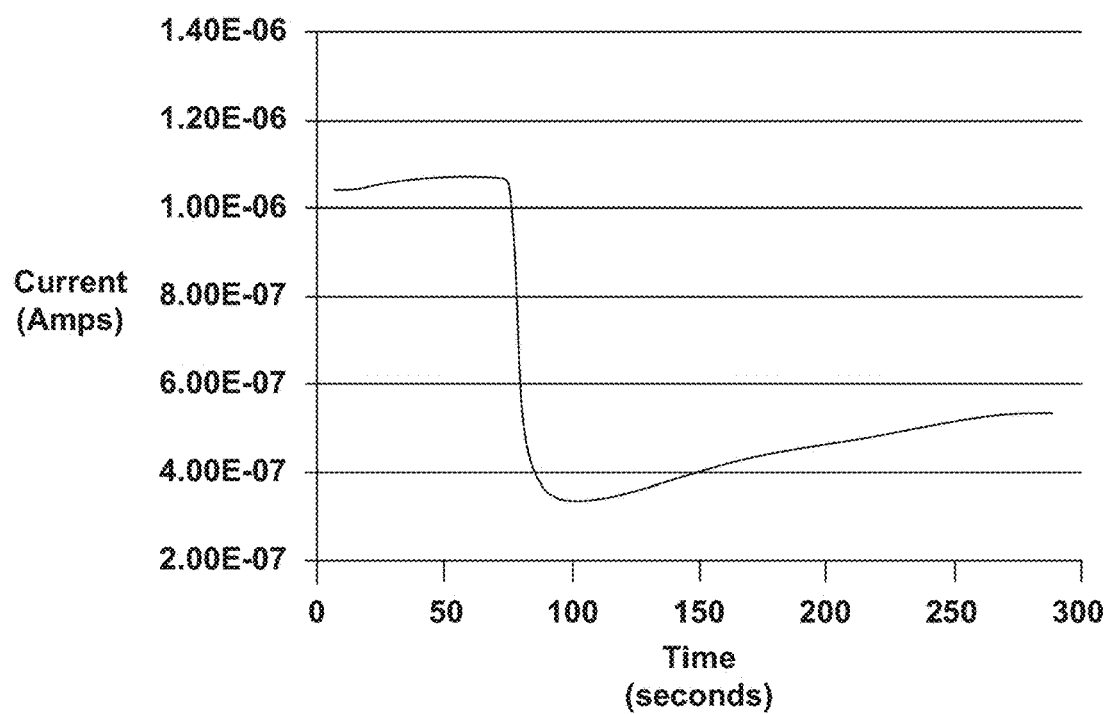
FIG. 9B is a graph illustrating change in current as a function of time for the sensor compound of FIG. 9A upon exposure to hydrogen peroxide.

FIG. 9A illustrates an SEM image of a sensor compound having a structure II.20. The structure II.20 chemical sensor was exposed to hydrogen peroxide to determine the electrical response properties of the chemical sensor upon exposure to this anylayte. FIG. 9B depicts an example of the response properties of one examples of this material upon exposure to hydrogen peroxide.

Figure 10A:
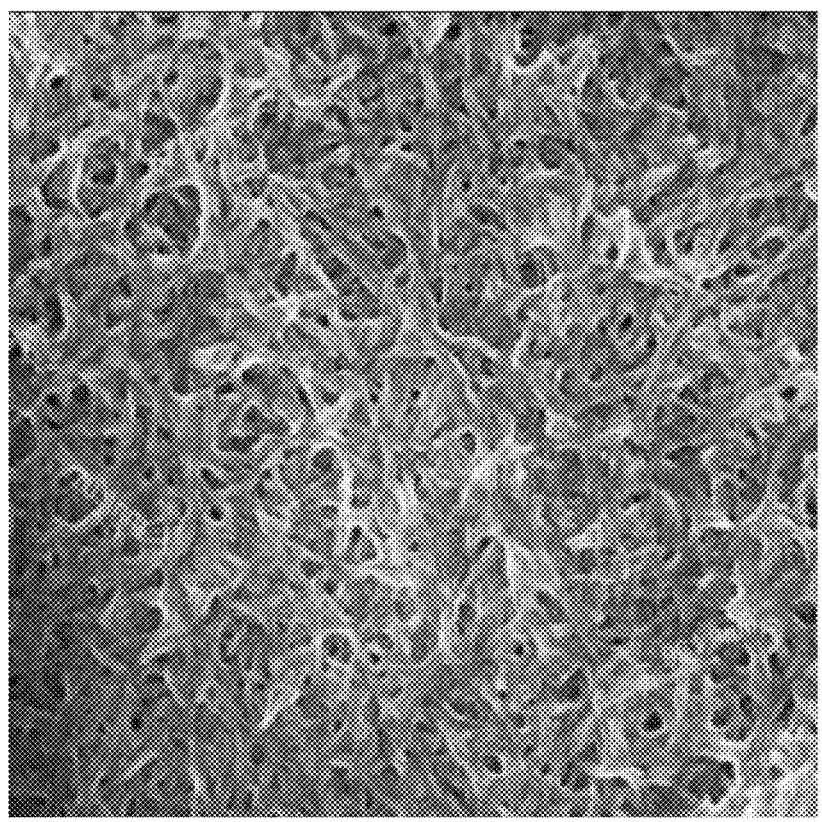
FIG. 10A illustrates an SEM image of a sensor compound, in accordance with some examples of the current disclosure.
Figure 10B:
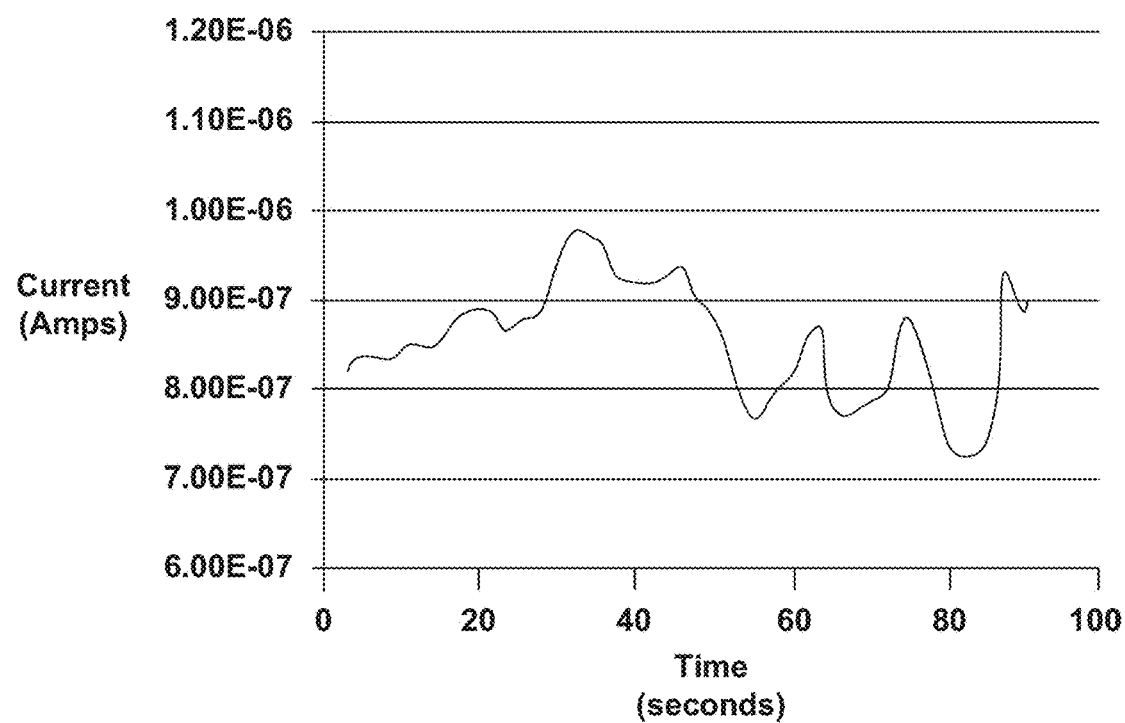
FIG. 10B is a graph illustrating change in current as a function of time for the sensor compound of FIG. 10A upon exposure to hydrogen peroxide.

FIG. 10A illustrates an SEM image of a sensor compound having a structure II.21. The structure II.21 chemical sensor was exposed to hydrogen peroxide to determine the electrical response properties of the chemical sensor upon exposure to this anylayte. FIG. 10B depicts an example of the response properties of one examples of this material upon exposure to hydrogen peroxide.

Figure 11A:
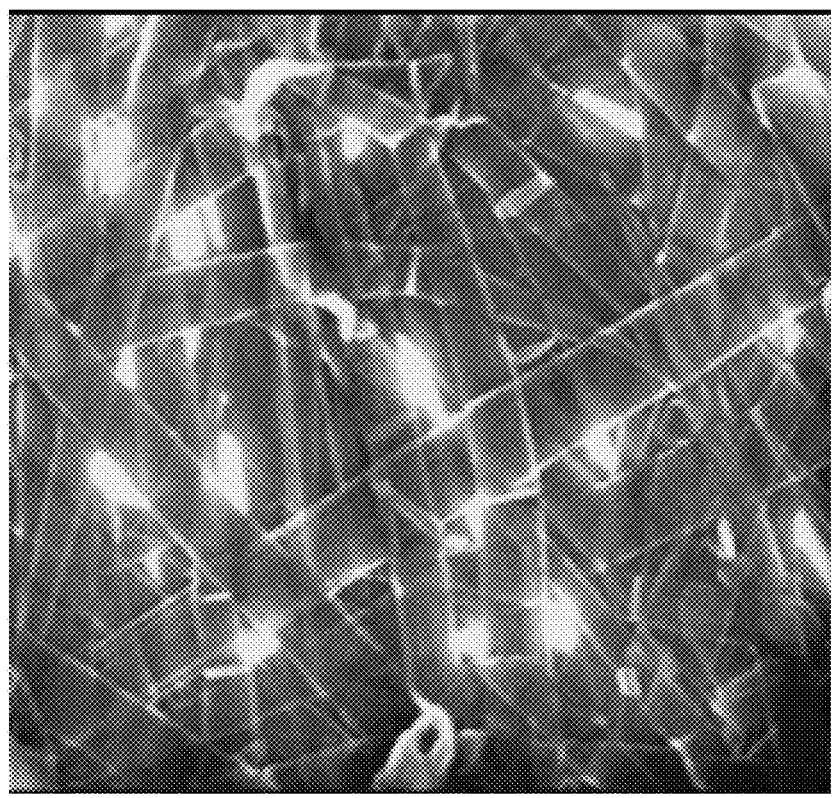
FIG. 11A illustrates an SEM image of a sensor compound, in accordance with some examples of the current disclosure.
Figure 11B:
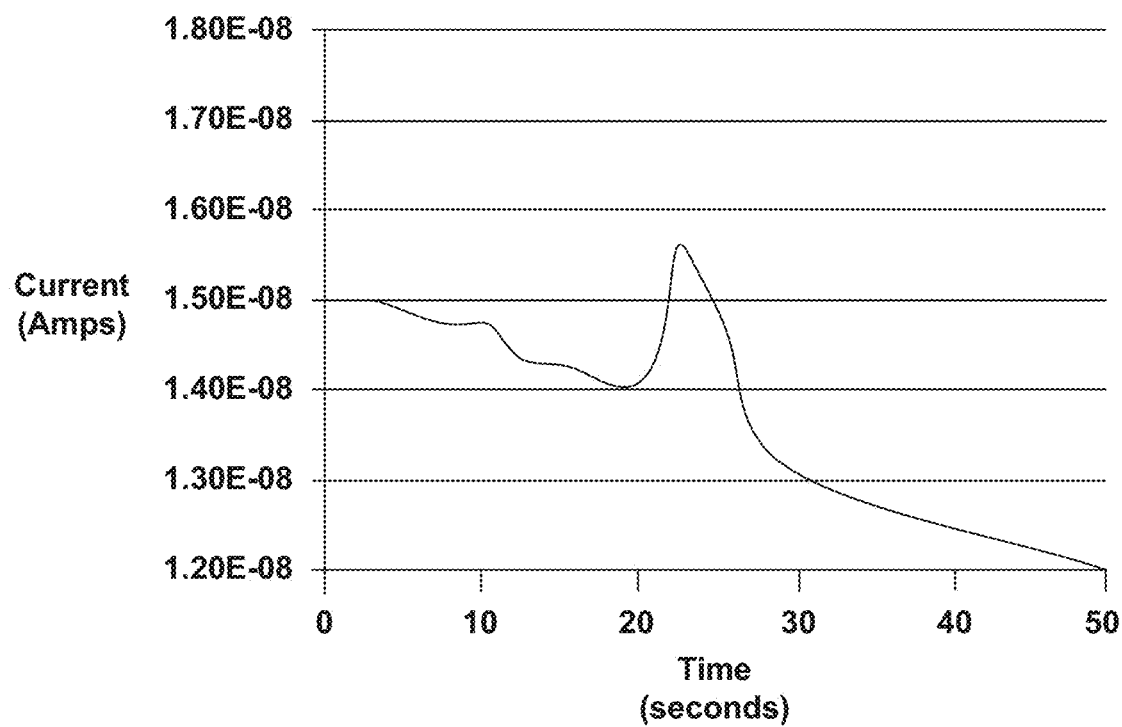
FIG. 11B is a graph illustrating change in current as a function of time for the sensor compound of FIG. 11A upon exposure to hydrogen peroxide.

FIG. 11A illustrates an SEM image of a sensor compound having a structure II.22. The structure II.22 chemical sensor was exposed to hydrogen peroxide to determine the electrical response properties of the chemical sensor upon exposure to this anylayte. FIG. 11B depicts an example of the response properties of one examples of this material upon exposure to hydrogen peroxide.

Figure 12A:
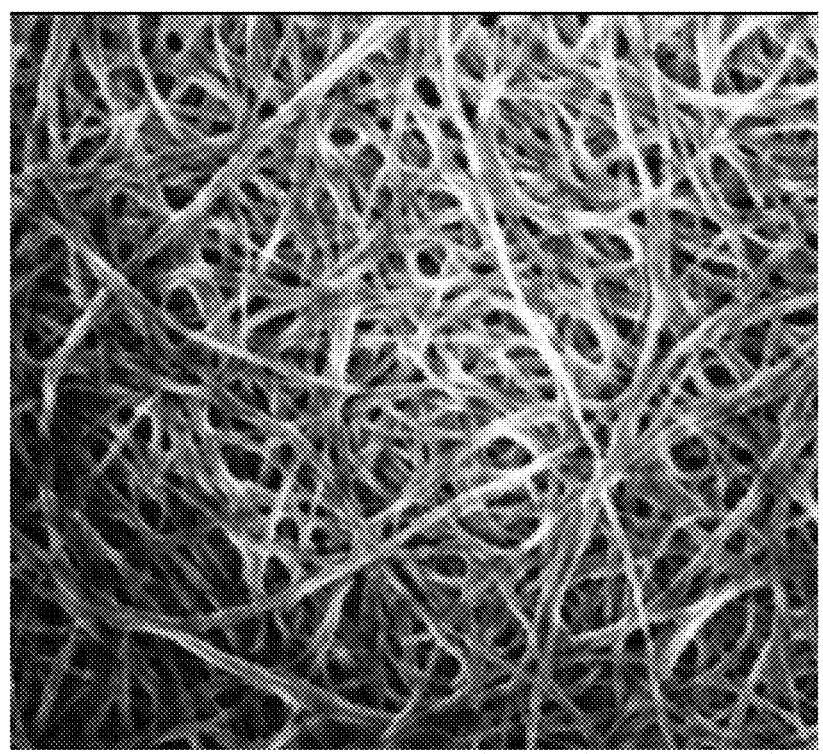
FIG. 12A illustrates an SEM image of a sensor compound, in accordance with some examples of the current disclosure.
Figure 12B:
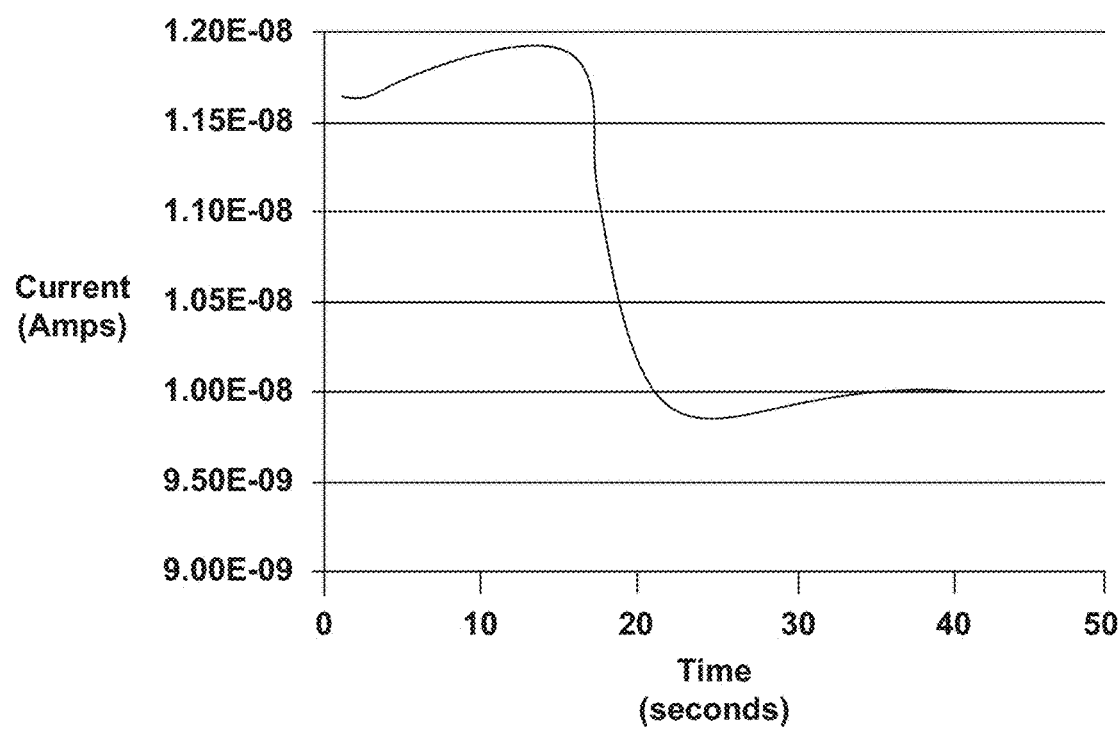
FIG. 12B is a graph illustrating change in current as a function of time for the sensor compound of FIG. 12A upon exposure to hydrogen peroxide.

FIG. 12A illustrates an SEM image of a sensor compound having a structure II.23. The structure II.23 chemical sensor was exposed to hydrogen peroxide to determine the electrical response properties of the chemical sensor upon exposure to this anylayte. FIG. 12B depicts an example of the response properties of one examples of this material upon exposure to hydrogen peroxide.

Figure 13A:
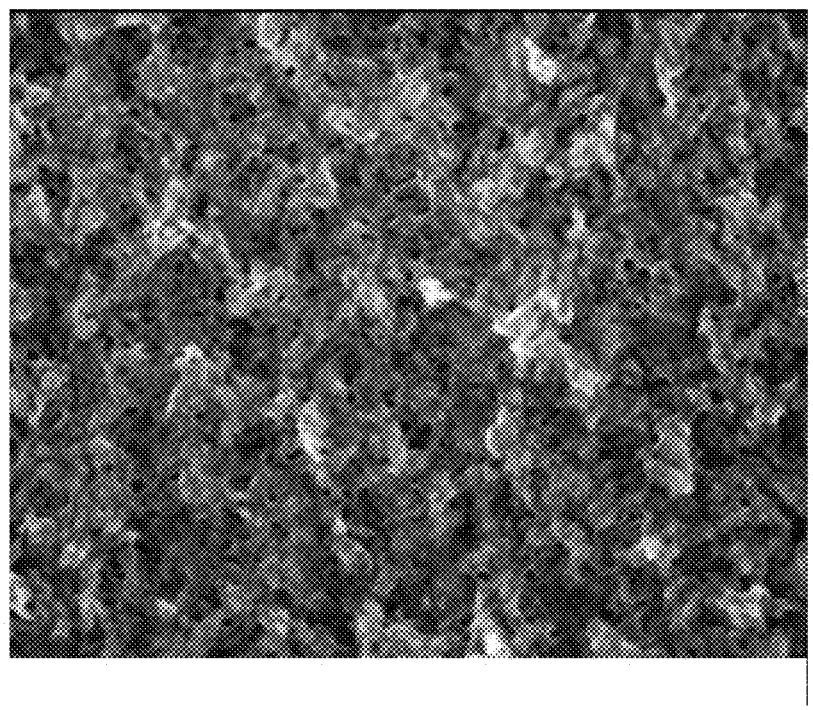
FIG. 13A illustrates an SEM image of a sensor compound, in accordance with some examples of the current disclosure.
Figure 13B:
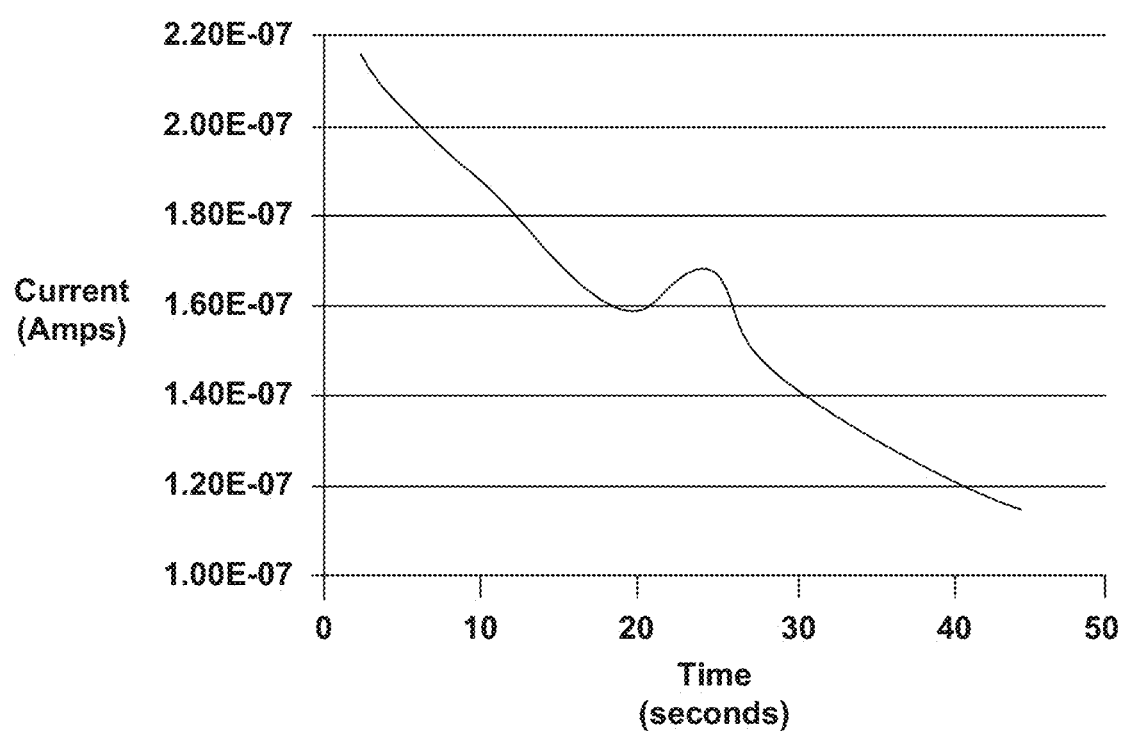
FIG. 13B is a graph illustrating change in current as a function of time for the sensor compound of FIG. 13A upon exposure to hydrogen peroxide.

FIG. 13A illustrates an SEM image of a sensor compound having a structure II.24. The structure II.24 chemical sensor was exposed to hydrogen peroxide to determine the electrical response properties of the chemical sensor upon exposure to this anylayte. FIG. 13B depicts an example of the response properties of one examples of this material upon exposure to hydrogen peroxide.

Figure 14A:
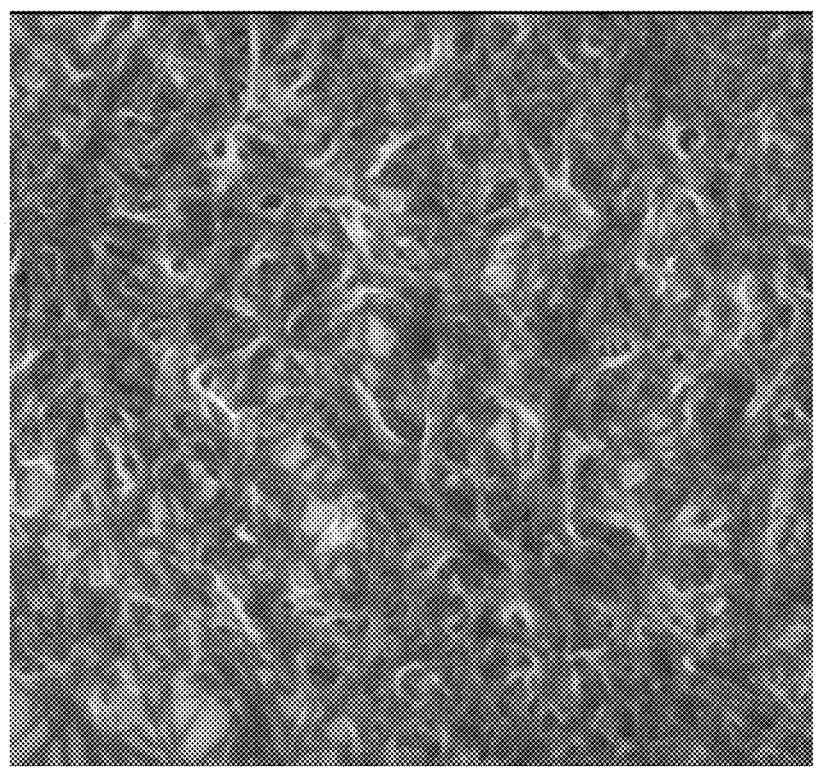
FIG. 14A illustrates an SEM image of a sensor compound, in accordance with some examples of the current disclosure.
Figure 14B:
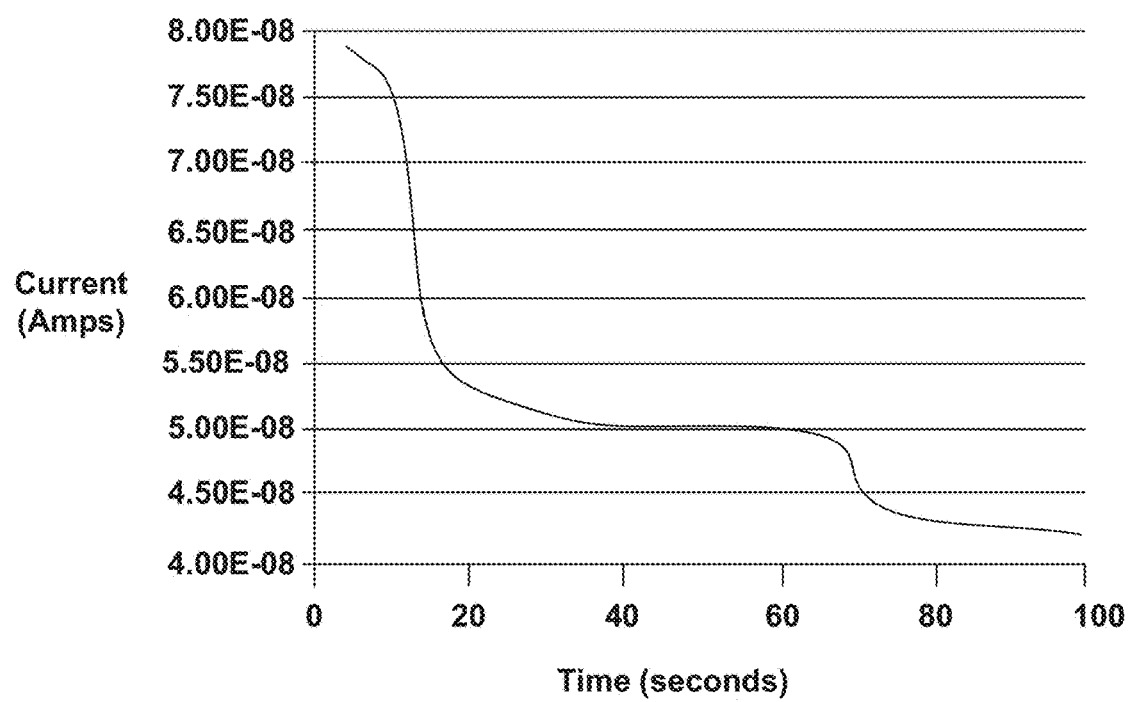
FIG. 14B is a graph illustrating change in current as a function of time for the sensor compound of FIG. 14A upon exposure to hydrogen peroxide.

FIG. 14A illustrates an SEM image of a sensor compound having a structure II.25. The structure II.25 chemical sensor was exposed to hydrogen peroxide to determine the electrical response properties of the chemical sensor upon exposure to this anylayte. FIG. 14B depicts an example of the response properties of one examples of this material upon exposure to hydrogen peroxide.

Figure 15A:
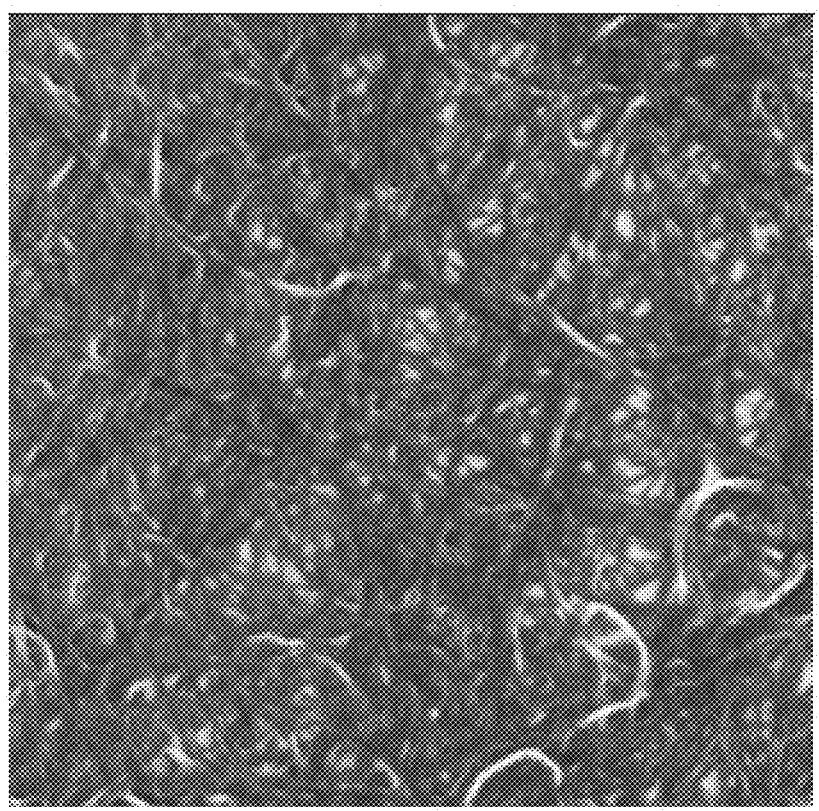
FIG. 15A illustrates an SEM image of a sensor compound, in accordance with some examples of the current disclosure.
Figure 15B:
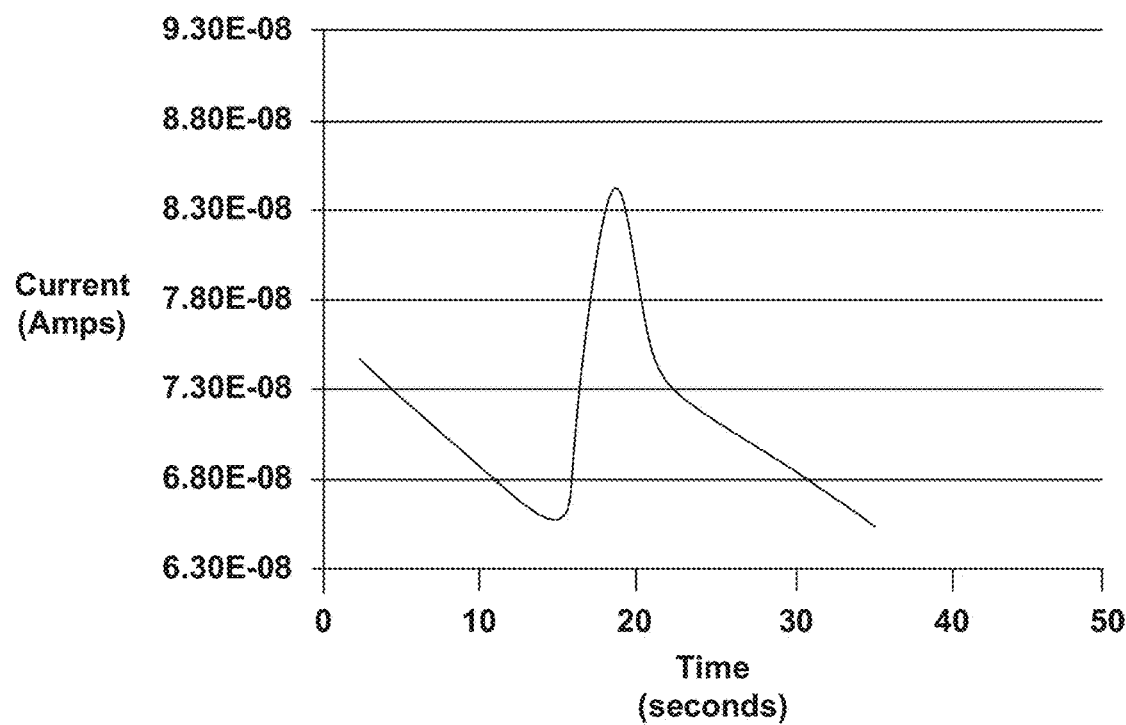
FIG. 15B is a graph illustrating change in current as a function of time for the sensor compound of FIG. 15A upon exposure to hydrogen peroxide.

FIG. 15A illustrates an SEM image of a sensor compound having a structure II.26. The structure II.26 chemical sensor was exposed to hydrogen peroxide to determine the electrical response properties of the chemical sensor upon exposure to this anylayte. FIG. 15B depicts an example of the response properties of one examples of this material upon exposure to hydrogen peroxide.

Figure 16A:
FIG. 16A illustrates an SEM image of a sensor compound, in accordance with some examples of the current disclosure.
Figure 16B:
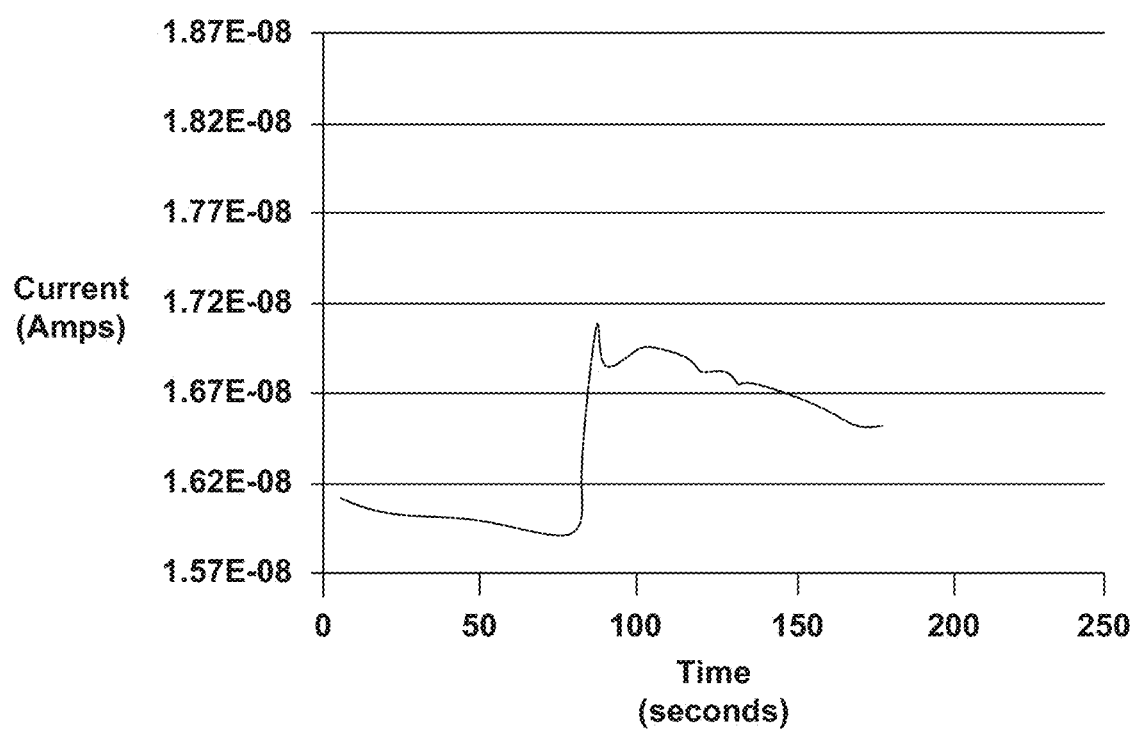
FIG. 16B is a graph illustrating change in current as a function of time for the sensor compound of FIG. 16A upon exposure to hydrogen peroxide.

FIG. 16A illustrates an SEM image of a sensor compound having a structure III.02. The structure III.02 chemical sensor was exposed to hydrogen peroxide to determine the electrical response properties of the chemical sensor upon exposure to this anylayte. FIG. 16B depicts an example of the response properties of one examples of this material upon exposure to hydrogen peroxide.

Figure 17A:
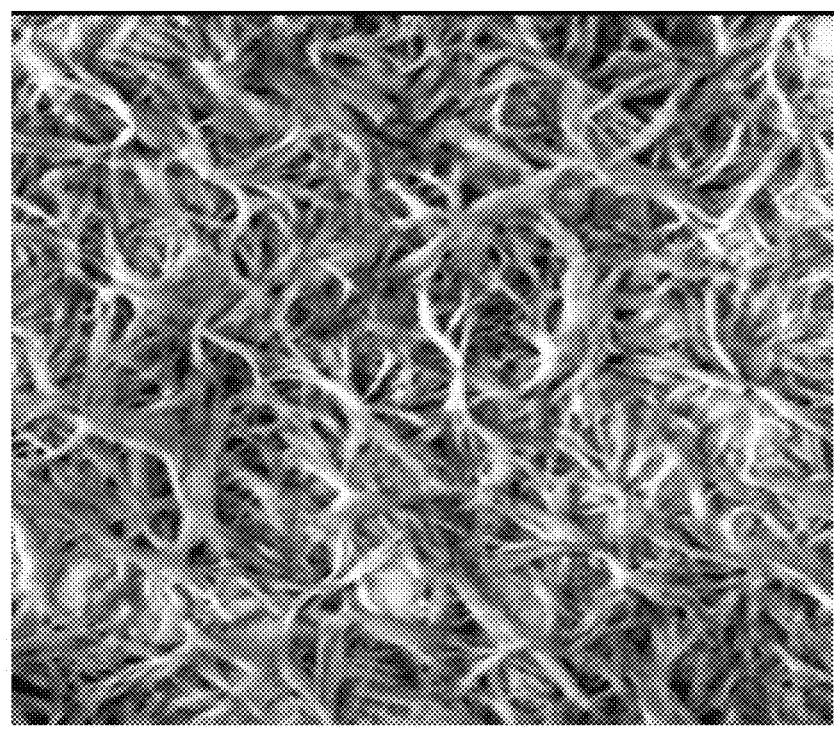
FIG. 17A illustrates an SEM image of a sensor compound, in accordance with some examples of the current disclosure.
Figure 17B:
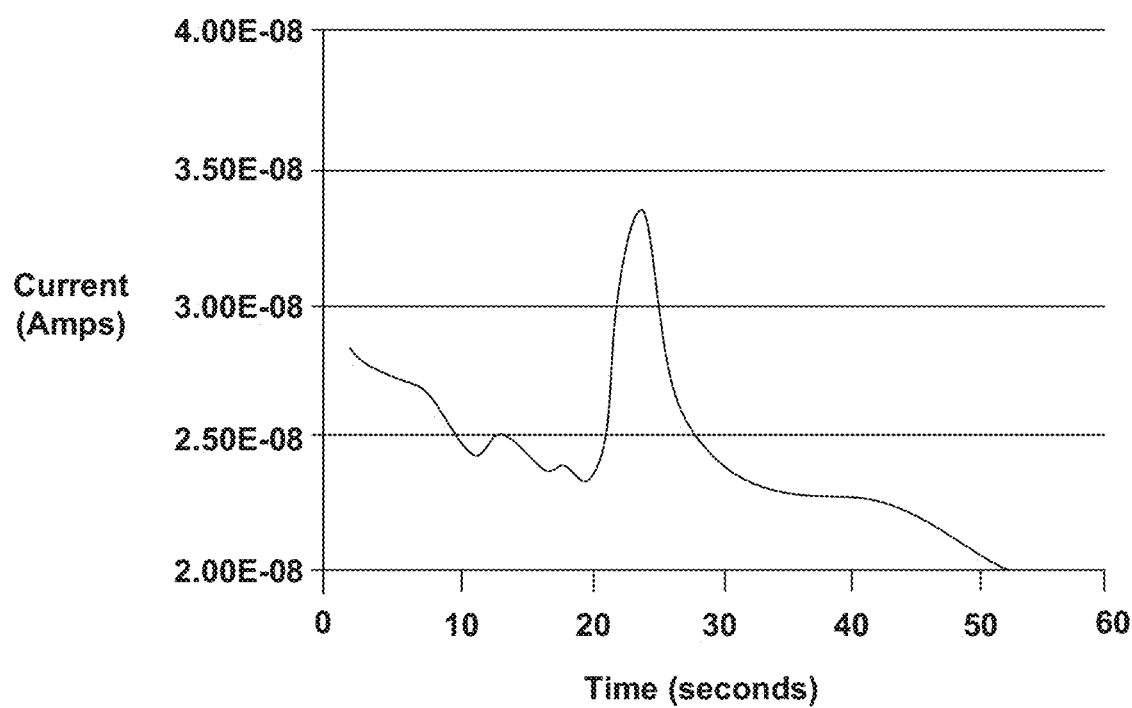
FIG. 17B is a graph illustrating change in current as a function of time for the sensor compound of FIG. 17A upon exposure to hydrogen peroxide.

FIG. 17A illustrates an SEM image of a sensor compound having a structure II.27. The structure II.27 chemical sensor was exposed to hydrogen peroxide to determine the electrical response properties of the chemical sensor upon exposure to this anylayte. FIG. 17B depicts an example of the response properties of one examples of this material upon exposure to hydrogen peroxide.

Figure 18:
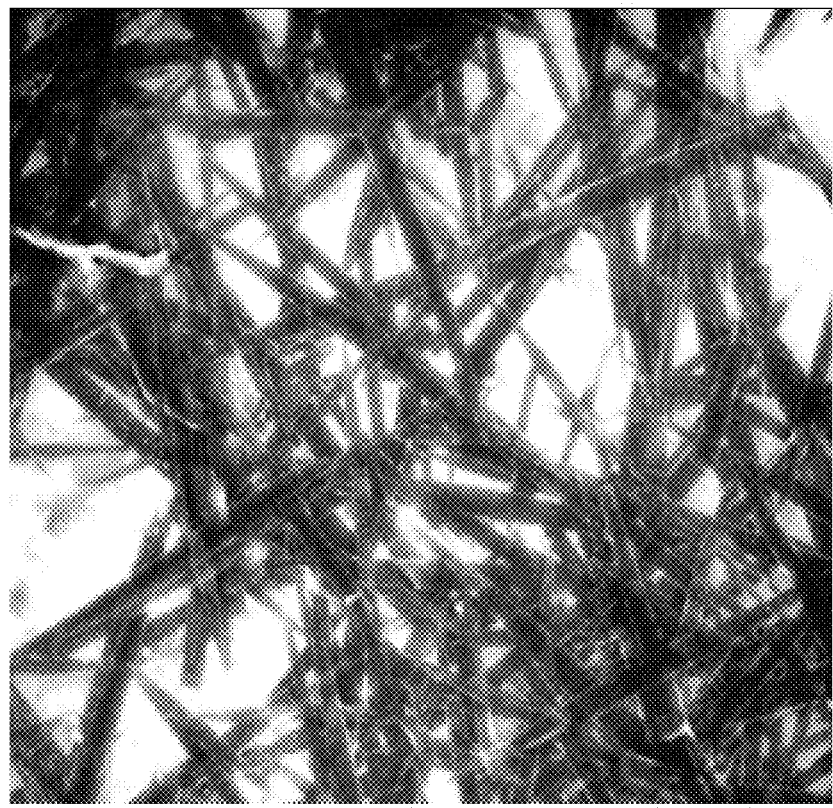
FIG. 18 illustrates an SEM image of a sensor compound, in accordance with some examples of the current disclosure.

FIG. 18 illustrates an SEM image of a sensor compound having a structure II.28.

Figure 19A:
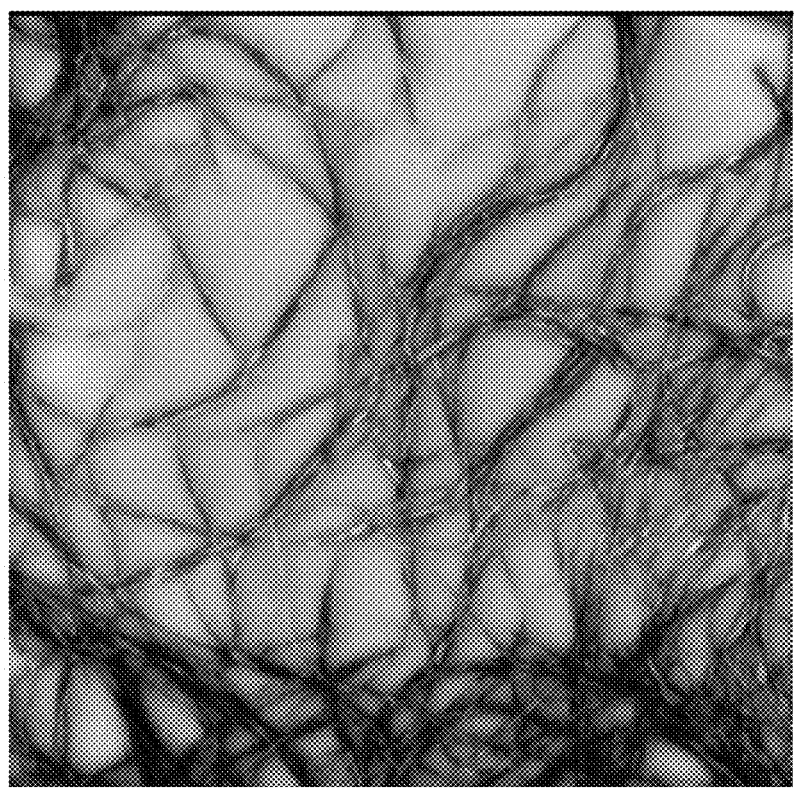
FIG. 19A illustrates an SEM image of a sensor compound, in accordance with some examples of the current disclosure.
Figure 19B:
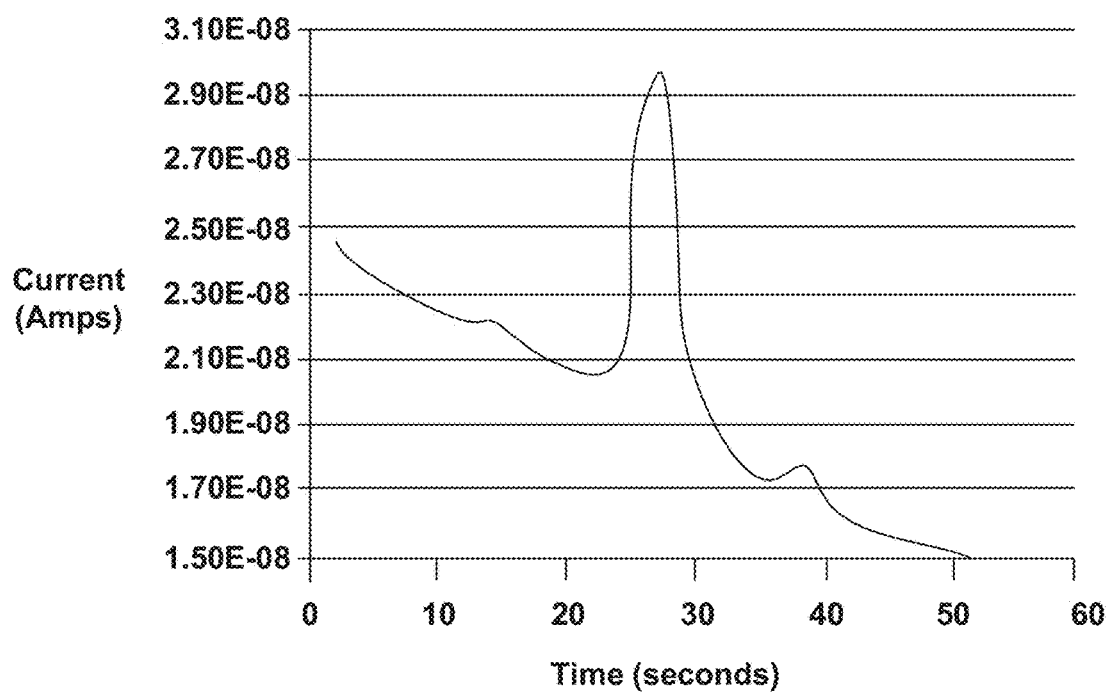
FIG. 19B is a graph illustrating change in current as a function of time for the sensor compound of FIG. 19A upon exposure to hydrogen peroxide.

FIG. 19A illustrates an SEM image of a sensor compound having a structure II.29. The structure II.29 chemical sensor was exposed to hydrogen peroxide to determine the electrical response properties of the chemical sensor upon exposure to this anylayte. FIG. 19B depicts an example of the response properties of one examples of this material upon exposure to hydrogen peroxide.

Example 3—Synthesis of Select Sensor Compounds

Figure 20:
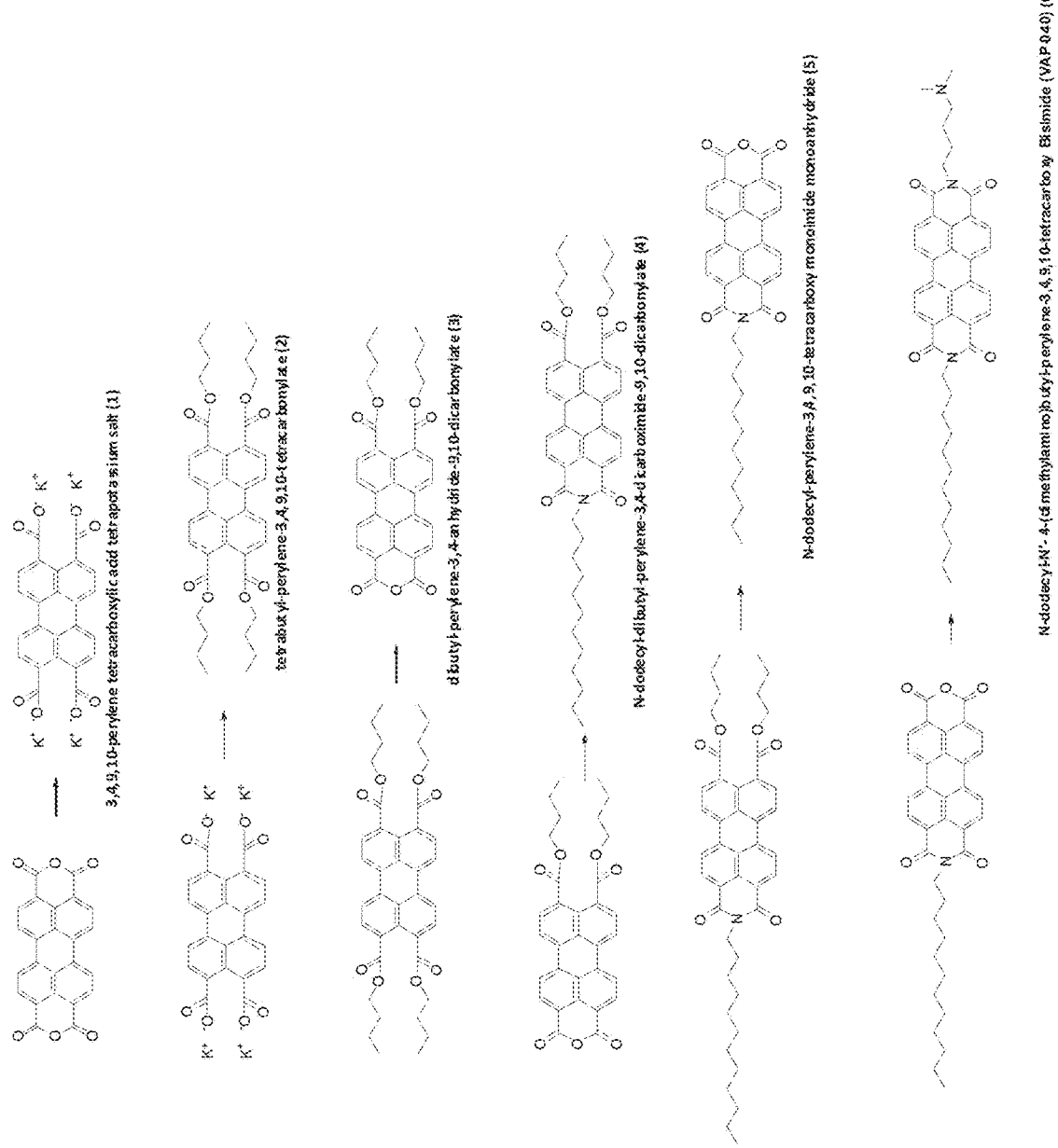
FIG. 20 is a schematic illustrating synthesis of N-dodecyl-N'-4-(dimethylamino) butyl-perylene-3,4,9,10-tetracarboxy bisimide (VAP-040) from 3,4,9,10-perylene tetracarboxylic acid bisanhydride in accordance with one specific example.

FIG. 20 is a schematic illustrating synthesis of N-dodecyl-N'-4-(dimethylamino)butyl-perylene-3,4,9,10-tetracarboxy Bisimide (VAP-040) from 3,4,9,10-perylene tetracarboxylic acid bisanhydride. Compounds 1-4 were prepared by the method outlined by Wang, Shi et al. 2013 (previously cited), while compound 5 was formed using the methods described in Sengupta, Dubey et al. 2014 (also previously cited).

A mixture of 3,4,9,10-perylene tetracarboxylic acid bisanhydride (15.0 g, 38.3 mmol) and potassium hydroxide (11.1 g, 172 mmol) in 190 mL water were heated to reflux for 3 hours. The reaction mixture was allowed to cool and then added to 145 mL isopropanol. The resulting precipitate was collected by filtration, washed with ethanol and vacuum dried to form a yellow solid 3,4,9,10-perylene tetracarboxylic acid tetrapotassium salt (1). The yellow solid (22.1 g, 38.1 mmol) was used without further purification.

The 3,4,9,10-perylene tetracarboxylic acid (22.1 g, 38.1 mmol), n-bromobutane (90.6 ml), potassium carbonate (44.2 g, 320 mmol), tetrabutyl ammonium bromide (18.5 g, 57.6 mmol), KI (0.63 g, 3.81 mmol) and 225 ml deionized water were stirred vigorously at reflux temperature for 16 h. The resulting mixture was cooled to room temperature and extracted with dichloromethane (100 mL×3). The combine organic layers were washed with water and brine. The $CH_2Cl_2$ solution was dried with $Na_2SO_4$. The solvent was removed with rotary concentrator and the residue was recrystallized from dichloromethane/acetonitrile and vacuum dried to afford (14.2 g, 57%) as a red solid. MS (MALDI-TOF): m/z=652.30 ($M^+$). The red solid was tetrabutyl-perylene-3,4,9,10-tetracarbonylate (2).

The tetrabutyl-perylene-3,4,9,10-tetracarbonylate (5.0 g, 7.67 mmol), p-toluenesulfonic acid monohydrate (pTsOH.H2O, 4.38 g, 23.0 mmol), were suspended in 50 ml n-heptane and heated to reflux for 30 minutes. The product was collected by filtration while still hot and washed with 100 mL ethanol then vacuum dried to yield 3.88 g (96%) as a dark red solid. TLC (silica: 2% ACN in $CH_2Cl_2$) shows 1 spot rf=0.33. MS (MALDI-TOF): m/z=522.23 ($M^+$). The dark red solid was dibutyl-perylene-3,4-anhydride-9,10-dicarbonylate (3).

In a 250 mL rb flask, dibutyl-perylene-3,4-anhydride-9,10-dicarbonylate (6.0 g, 11.5 mmol), dodecyl amine (3.2 g, 17.2 mmol) and acetic acid (3.6 mL, 3.80 g, 63.3 mmol) were dissolved in 72 mL NMP and heated to 120° C. for 45 minutes. The reaction mixture was poured into 300 mL water. The precipitated product was isolated by filtration. The product was dissolved in chloroform and washed with water and brine and dried over $Na_2SO_4$. The reaction product was taken up in approximately 100 mL hot ethyl acetate and filtered while hot to remove a small amount of di-addition product as N-dodecyl-dibutyl-perylene-3,4-dicarboximide-9,10-dicarbonylate (4). The pure product was then obtained after recrystallization from ethyl acetate/ethanol to afford 5.66 g (71%) product as a dark red solid. 1H NMR (CDCl3, 400 MHz, ppm): δ 8.55 (d, 2H), 8.37 (dd, 4H), 8.07 (d, 2H), 5.35 (t, 4H), 4.19 (t, 2H), 1.77-1.82 (m, 6H), 1.18-1.60 (m, 22H), 1.00 (t, 6H), 0.85 (t, 3H).

N-dodecyl-dibutyl-perylene-3,4-dicarboximide-9,10-dicarbonylate (5.66 g, 8.21 mmol) and p-toluenesulfonic acid monohydrate (p-TsOH.H2O, 7.8 g, 41.1 mmol) were taken in 225 mL of toluene. The resulting mixture was stirred at 90° C. for 18 h. After being cooled to room temperature the precipitate was collected by filtration, washed with methanol and vacuum dried to afford 4.51 g (98%) product as a dark red solid. MS (MALDI-TOF): m/z=560.0 ($M^+$). The resulting dark red solid product was N-dodecyl-perylene-3,4,9,10-tetracarboxy monoimide monoanhydride (5).

In a 10 mL vial combined N-dodecyl-perylene-3,4,9,10-tetracarboxy monoimide monoanhydride (50.0 mg, 0.089 mmol), 4-(dimethylamino)butylamine (31.0 mg, 0.268 mmol), $Zn(CO_2CH_3)_2$ (1 mg) and imidazole (750 mg). The vial was tightly capped and heated to 125° C. for 4 hours with magnetic stirring. The imidazole was dissolved in 2N HCl, the product was collected by filtration and washed with water and methanol. The product was dissolve in $CHCl_3$ (200 mL) and washed with saturated sodium bicarbonate, water, brine and dried over $Na_2SO_4$. The product was then recrystallized from $CHCL_3$/ACN and vacuum dried to afford 53.9 mg (92%) product as a very dark red solid. 1H NMR (CDCl3, 400 MHz, ppm): δ 8.55-8.74 (m, 8H), 4.14-4.31 (m, 4H), 2.37 (t, 2H), 2.25 (s, 6H), 1.68-1.87 (m, 4H), 1.18-1.33 (m, 20H), 0.85 (t, 3H). MS (MALDI-TOF): m/z=658.43 ($M^+$). This very dark red solid product was N-dodecyl-N'-4-(dimethylamino)butyl-perylene-3,4,9,10-tetracarboxy Bisimide (labeled VAP-040) (6).

This same synthesis route can also be used to form compounds consistent with Compound II structure with appropriate reagents.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A sensor compound for detecting a target analyte, comprising:
   a sensor compound selected from the group consisting of compounds having a structure according to the formula:

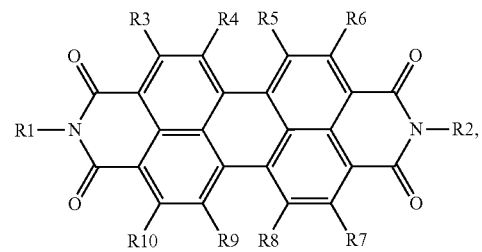

where R1 is chosen from $C_2$-$C_{20}$ substituted or unsubstituted linear aliphatic groups and branched aliphatic groups, wherein at least one hydrogen group of R1 has been substituted with a halide, where R2 comprises an alkylbenzene group, an aryl compound having an oxygen-containing side group, an aryl compound having a nitrogen-containing side group, an aryl compound having a sulfur-containing side group, or a combination thereof, and where R3-R10 are independently chosen from hydrogen, halides, carboxyl groups, hydroxyl groups, nitrile groups, $C_1$-$C_8$ alkyl groups, and combinations thereof; and combinations thereof.

2. The sensor compound of claim 1, wherein R1 is:

a $C_4$-$C_{16}$ linear or branched aliphatic group;

a linear aliphatic group; or a branched aliphatic group.

3. The sensor compound of claim 1, wherein R1 comprises an ether group, a heterocycle, an amine, an amide, or a combination thereof.

4. The sensor compound of claim 1, wherein at least one hydrogen group of R2 has been substituted with a halide.

5. The sensor compound of claim 1, wherein R2 comprises an alkylbenzene compound selected from the group consisting of

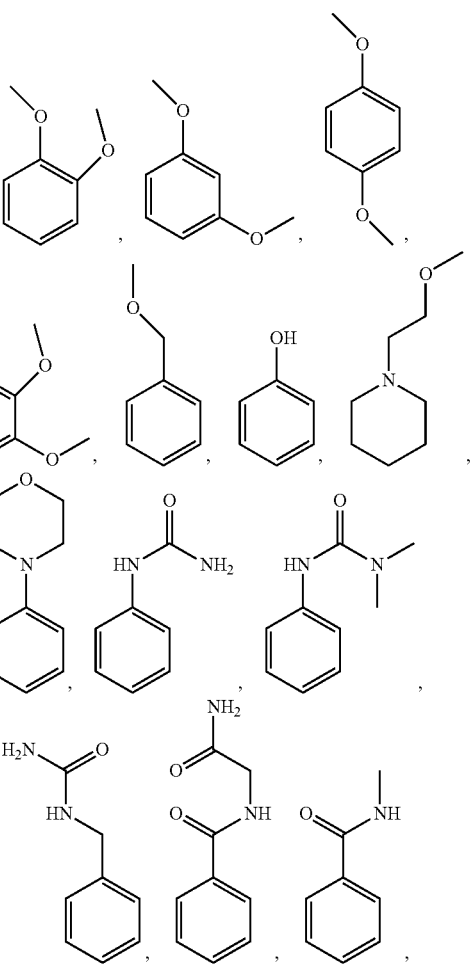

or combinations thereof.

6. The sensor compound of claim 1, wherein R2 comprises a heterocycle selected from the group consisting of and combinations thereof.

7. The sensor compound of claim 1, wherein R2 comprises an aryl compound having an oxygen-containing side group selected from the group consisting of and combinations thereof.

8. The sensor compound of claim 1, wherein R2 comprises an aryl compound having a nitrogen-containing side group selected from the group consisting of -continued

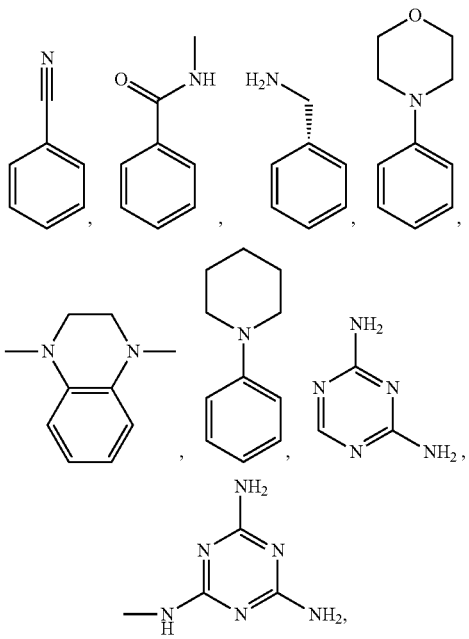

and combinations thereof.

9. The sensor compound of claim 1, wherein R2 comprises an aryl compound having a sulfur-containing side group selected from the group consisting of

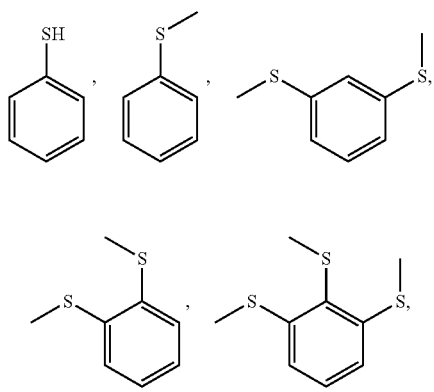

or combinations thereof.

10. The sensor compound of claim 1, wherein at least one of R3-R10 is not hydrogen.

11. The sensor compound of claim 10, wherein at least two of R3-R10 is a halide, a carboxyl group, a hydroxyl group, a nitrile group, a $C_1$-$C_8$ alkyl group, or a combination thereof.

12. A sensor device for detecting a target analyte, comprising:
   a substrate; and
   a sensor compound positioned on the substrate in a plurality of detection zones, said sensor compound having a nanostructure selected from nanofibers and nanobelts and a chemical structure according to the formula:

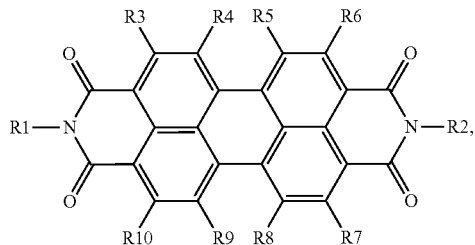

where R1 is chosen from $C_2$-$C_{20}$ linear aliphatic groups and branched aliphatic groups, where R2 comprises an alkylbenzene group, an aryl compound having an oxygen-containing side group, an aryl compound having a nitrogen-containing side group, an aryl compound having a sulfur-containing side group, or a combination thereof, and where R3-R10 are independently chosen from hydrogen, halides, carboxyl groups, hydroxyl groups, nitrile groups, $C_1$-$C_8$ alkyl groups, and combinations thereof; and combinations thereof.

13. The sensor device of claim 12, wherein at least one of the plurality of detection zones comprises a separately addressable electrode pair.

14. The sensor device of claim 12, wherein the substrate includes a plurality of holes allowing fluid flow through the substrate.

15. The sensor device of claim 12, further comprising a light source operably positioned to illuminate at least one of the plurality of detection zones, and further comprising a fluorescence detector.

16. The sensor device of claim 12, wherein at least two of the plurality of detection zones comprise different sensor compounds.

17. The sensor device of claim 16, wherein at least one of the different sensor compounds has a structure according to Formula III:

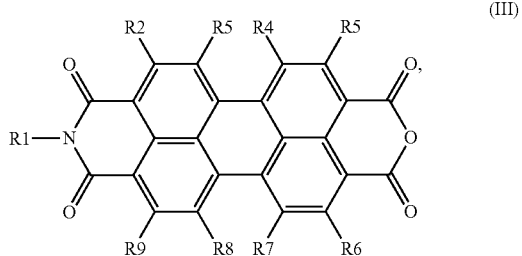

where R1 is chosen from $C_1$-$C_{20}$ linear aliphatic groups, branched aliphatic groups, cyclic groups, and aryl groups, and where R2-R9 are independently chosen from hydrogen, halides, carboxyl groups, hydroxyl groups, nitrile groups, $C_1$-$C_8$ alkyl groups, and combinations thereof.

18. The sensor device of claim 12, wherein the sensor compound forms a porous film.

19. A sensor compound for detecting a target analyte, having a structure according to the formula:

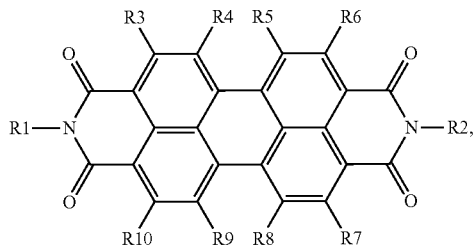

where R1 is chosen from $C_2$-$C_{20}$ linear aliphatic groups and branched aliphatic groups, where R2 comprises

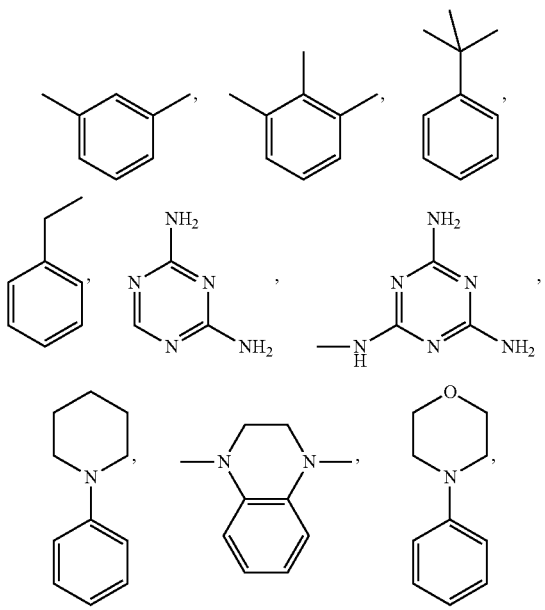

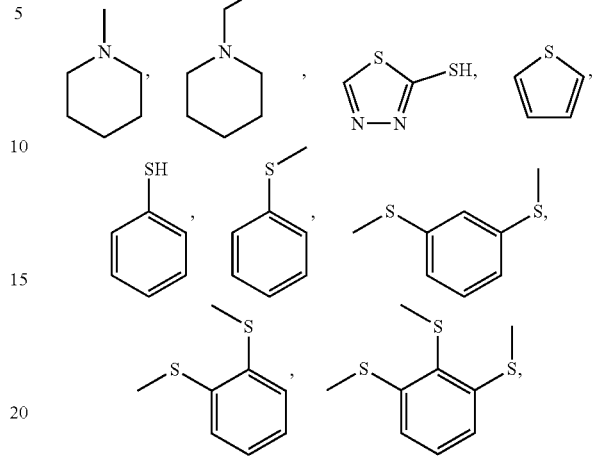

or a combination thereof, and where R3-R10 are independently chosen from hydrogen, halides, carboxyl groups, hydroxyl groups, nitrile groups, $C_1$-$C_8$ alkyl groups, and combinations thereof; and combinations thereof.

20. The sensor compound of claim 19, wherein R1 is:
a $C_4$-$C_{16}$ substituted or unsubstituted linear or branched aliphatic group;
a substituted or unsubstituted linear aliphatic group; or
a substituted or unsubstituted branched aliphatic group.

21. The sensor compound of claim 19, wherein R1 comprises an ether group, a heterocycle, an amine, an amide, or a combination thereof.

22. The sensor compound of claim 19 wherein at least one hydrogen group of R1 has been substituted with a halide.

23. The sensor compound of claim 19, wherein at least one of R3-R10 is not hydrogen.

24. The sensor compound of claim 23, wherein at least two of R3-R10 is a halide, a carboxyl group, a hydroxyl group, a nitrile group, a $C_1$-$C_8$ alkyl group, or a combination thereof.

* * * * *